United States Patent
Spence

(10) Patent No.: US 9,585,991 B2
(45) Date of Patent: Mar. 7, 2017

(54) DEVICES, SYSTEMS, AND METHODS FOR FACILITATING FLOW FROM THE HEART TO A BLOOD PUMP

(71) Applicant: SCR, INC., Louisville, KY (US)

(72) Inventor: Paul A. Spence, Louisville, KY (US)

(73) Assignee: HeartWare, Inc., Mounds View, MN (US)

( * ) Notice: Subject to any disclaimer, the term of this patent is extended or adjusted under 35 U.S.C. 154(b) by 0 days.

(21) Appl. No.: 14/055,485

(22) Filed: Oct. 16, 2013

(65) Prior Publication Data

US 2014/0107399 A1    Apr. 17, 2014

Related U.S. Application Data

(60) Provisional application No. 61/795,407, filed on Oct. 16, 2012.

(51) Int. Cl.
*A61M 1/10* (2006.01)
*A61B 17/34* (2006.01)

(52) U.S. Cl.
CPC ............ *A61M 1/10* (2013.01); *A61M 1/1008* (2014.02); *A61B 2017/3488* (2013.01)

(58) Field of Classification Search
CPC ................ A61M 1/3653; A61M 25/00; A61M 25/0067; A61M 25/0074; A61M 25/04;
(Continued)

(56) References Cited

U.S. PATENT DOCUMENTS

| 2,935,068 A | 5/1960 | Donaldson |
| 3,195,540 A | 7/1965 | Waller |

(Continued)

FOREIGN PATENT DOCUMENTS

| FR | 1514319 | 2/1968 |
| WO | WO 82/01644 | 5/1982 |

(Continued)

OTHER PUBLICATIONS

Antaki, J. F. et al., "An improved left ventricular cannula for chronic dynamic blood pump support," Artificial Organs, 19(7):671-675 (1995).

(Continued)

*Primary Examiner* — Allen Porter, Jr.
(74) *Attorney, Agent, or Firm* — Christopher & Weisberg, P.A.

(57) ABSTRACT

An apparatus includes a tubular member defining a lumen and a channel, and a support member. The tubular member has a connection portion configured to be coupled to an organ wall. An outer edge of the connection portion is configured to contact a first portion of an inner surface of the wall when the connection portion is in an expanded configuration such that an interior volume of the organ is in fluid communication with the lumen. The support member is movably disposed within the channel and is configured to minimize movement of the wall relative to the tubular member. An end portion of the support member is disposed within the channel when the support member is in a first configuration. The end portion of the support member configured to contact a second portion of the inner surface of the wall when the support member is in a second configuration.

16 Claims, 35 Drawing Sheets

(58) Field of Classification Search
CPC ........ A61M 2210/12; A61M 2210/122; A61M 2210/125; A61M 2210/127; A61M 1/1008; A61M 2025/0004
USPC .............................................. 600/16, 17, 18
See application file for complete search history.

(56) References Cited

U.S. PATENT DOCUMENTS

| | | |
|---|---|---|
| 3,818,511 A | 6/1974 | Goldberg et al. |
| 3,942,535 A | 3/1976 | Schulman |
| 4,014,317 A | 3/1977 | Bruno |
| 4,080,958 A | 3/1978 | Bregman et al. |
| 4,116,589 A | 9/1978 | Rishton |
| 4,366,819 A | 1/1983 | Kaster |
| 4,790,825 A | 12/1988 | Bernstein et al. |
| 4,994,078 A | 2/1991 | Jarvik |
| 4,995,857 A | 2/1991 | Arnold |
| 5,163,954 A | 11/1992 | Curcio et al. |
| 5,171,207 A | 12/1992 | Whalen |
| 5,171,218 A | 12/1992 | Fonger et al. |
| 5,190,528 A | 3/1993 | Fonger et al. |
| 5,287,852 A | 2/1994 | Arkinstall |
| 5,290,227 A | 3/1994 | Pasque |
| 5,290,251 A | 3/1994 | Griffith |
| 5,312,341 A | 5/1994 | Turi |
| 5,338,301 A | 8/1994 | Diaz |
| 5,344,385 A | 9/1994 | Buck et al. |
| 5,344,443 A | 9/1994 | Palma et al. |
| 5,449,342 A | 9/1995 | Hirose et al. |
| 5,545,191 A | 8/1996 | Mann et al. |
| 5,653,676 A | 8/1997 | Buck et al. |
| 5,676,670 A | 10/1997 | Kim |
| 5,695,471 A | 12/1997 | Wampler |
| 5,697,936 A | 12/1997 | Shipko et al. |
| 5,701,919 A | 12/1997 | Buck |
| 5,704,891 A | 1/1998 | Mussivand |
| 5,711,753 A | 1/1998 | Pacella et al. |
| 5,738,649 A | 4/1998 | Macoviak |
| 5,741,316 A | 4/1998 | Chen et al. |
| 5,743,845 A | 4/1998 | Runge |
| 5,840,070 A | 11/1998 | Wampler |
| 5,858,009 A | 1/1999 | Jonkman |
| 5,904,666 A | 5/1999 | DeDecker et al. |
| 5,921,971 A | 7/1999 | Agro et al. |
| 5,924,848 A | 7/1999 | Izraelev |
| 5,924,975 A | 7/1999 | Goldowsky |
| 5,938,412 A | 8/1999 | Izraelev |
| 5,941,813 A | 8/1999 | Sievers et al. |
| 5,944,745 A | 8/1999 | Rueter |
| 5,947,892 A | 9/1999 | Benkowski et al. |
| 5,948,006 A | 9/1999 | Mann |
| 5,965,089 A | 10/1999 | Jarvik et al. |
| 5,984,857 A | 11/1999 | Buck et al. |
| 6,001,056 A | 12/1999 | Jassawalla et al. |
| 6,017,355 A | 1/2000 | Hessel et al. |
| 6,116,862 A | 9/2000 | Rau et al. |
| 6,132,363 A | 10/2000 | Freed et al. |
| 6,186,999 B1 | 2/2001 | Chen |
| 6,273,861 B1 | 8/2001 | Bates et al. |
| 6,299,575 B1 | 10/2001 | Bolling |
| 6,328,699 B1 | 12/2001 | Eigler et al. |
| 6,354,299 B1 | 3/2002 | Fischell et al. |
| 6,358,266 B1 | 3/2002 | Bonutti |
| 6,406,420 B1 | 6/2002 | McCarthy et al. |
| 6,428,464 B1 | 8/2002 | Bolling |
| 6,471,633 B1 | 10/2002 | Freed |
| 6,511,412 B1 | 1/2003 | Freed et al. |
| 6,530,876 B1 | 3/2003 | Spence |
| 6,565,536 B1 | 5/2003 | Sohn |
| 6,579,223 B2 | 6/2003 | Palmer |
| 6,669,708 B1 | 12/2003 | Nissenbaum et al. |
| 6,723,039 B2 | 4/2004 | French et al. |
| 6,746,475 B1* | 6/2004 | Rivelli, Jr. ................ A61F 2/88 623/1.15 |
| 6,808,508 B1 | 10/2004 | Zafirelis et al. |
| 6,889,082 B2 | 5/2005 | Bolling et al. |
| 6,926,662 B1 | 8/2005 | Aboul-Hosn et al. |
| 6,955,175 B2 | 10/2005 | Stevens et al. |
| 6,994,094 B2 | 2/2006 | Schwartz |
| 6,994,666 B2 | 2/2006 | Shannon et al. |
| 7,037,253 B2 | 5/2006 | French et al. |
| 7,048,681 B2 | 5/2006 | Tsubouchi et al. |
| 7,056,294 B2 | 6/2006 | Khairkhahan et al. |
| 7,077,801 B2 | 7/2006 | Haverich |
| 7,169,164 B2 | 1/2007 | Borillo et al. |
| 7,214,230 B2 | 5/2007 | Brock et al. |
| 7,273,446 B2 | 9/2007 | Spence |
| 7,288,104 B2* | 10/2007 | Heil, Jr. ........................ 606/213 |
| 7,340,288 B1 | 3/2008 | Karicherla et al. |
| 7,473,239 B2 | 1/2009 | Wang et al. |
| 7,520,850 B2 | 4/2009 | Brockway |
| 7,585,290 B2 | 9/2009 | Kathrani et al. |
| 7,666,203 B2 | 2/2010 | Chanduszko et al. |
| 7,766,813 B2 | 8/2010 | Spence |
| 7,785,246 B2 | 8/2010 | Aboul-Hosn et al. |
| 7,881,807 B2 | 2/2011 | Schaer |
| 7,905,823 B2 | 3/2011 | Farnan et al. |
| 8,092,364 B2 | 1/2012 | Spence |
| 8,157,720 B2 | 4/2012 | Marseille et al. |
| 8,308,715 B2 | 11/2012 | Farnan et al. |
| 8,333,686 B2 | 12/2012 | Marseille et al. |
| 8,333,687 B2 | 12/2012 | Farnan et al. |
| 8,333,727 B2 | 12/2012 | Farnan |
| 8,343,029 B2 | 1/2013 | Farnan et al. |
| 8,394,010 B2 | 3/2013 | Farnan |
| 8,460,168 B2 | 6/2013 | Farnan |
| 8,465,410 B2 | 6/2013 | Marseille et al. |
| 8,512,012 B2 | 8/2013 | Akdis et al. |
| 8,545,379 B2 | 10/2013 | Marseille et al. |
| 8,545,380 B2 | 10/2013 | Farnan et al. |
| 8,607,800 B2 | 12/2013 | Thapliyal et al. |
| 8,784,291 B2 | 7/2014 | Farnan et al. |
| 2002/0082614 A1 | 6/2002 | Logan et al. |
| 2002/0133223 A1* | 9/2002 | Vito ........................ A61F 2/885 623/1.18 |
| 2002/0151761 A1 | 10/2002 | Viole et al. |
| 2002/0151918 A1* | 10/2002 | Lafontaine ......... A61B 17/3207 606/159 |
| 2002/0173693 A1 | 11/2002 | Landesberg |
| 2003/0055440 A1* | 3/2003 | Jones ............... A61B 17/12022 606/151 |
| 2003/0069468 A1 | 4/2003 | Bolling et al. |
| 2003/0088147 A1 | 5/2003 | Bolling et al. |
| 2003/0139643 A1 | 7/2003 | Smith et al. |
| 2003/0158573 A1* | 8/2003 | Gittings .................... A61F 2/24 606/194 |
| 2003/0176760 A1 | 9/2003 | El Oakley et al. |
| 2004/0116992 A1 | 6/2004 | Wardle et al. |
| 2004/0147803 A1 | 7/2004 | Hegde et al. |
| 2004/0210180 A1* | 10/2004 | Altman ............... A61M 1/3653 604/4.01 |
| 2004/0260384 A1* | 12/2004 | Allen ....................... A61F 2/88 623/1.12 |
| 2005/0010095 A1* | 1/2005 | Stewart ............. A61B 18/1492 600/374 |
| 2005/0020965 A1* | 1/2005 | Rioux ............... A61B 18/1477 604/21 |
| 2005/0149097 A1* | 7/2005 | Regnell ............ A61M 25/0068 606/191 |
| 2005/0154250 A1* | 7/2005 | Aboul-Hosn ......... A61M 1/101 600/16 |
| 2005/0245896 A1* | 11/2005 | Kucharczyk ........ A61M 25/003 604/522 |
| 2006/0009737 A1 | 1/2006 | Whiting et al. |
| 2007/0049787 A1 | 3/2007 | Nose et al. |
| 2007/0106315 A1 | 5/2007 | Gregoric et al. |
| 2007/0197855 A1 | 8/2007 | Richardson et al. |
| 2007/0233041 A1 | 10/2007 | Gellman |
| 2007/0239255 A1* | 10/2007 | Hines ....................... A61F 2/88 623/1.12 |
| 2008/0009891 A1 | 1/2008 | Cohn |
| 2008/0076959 A1* | 3/2008 | Farnan .................... A61M 1/12 600/16 |

(56) References Cited

U.S. PATENT DOCUMENTS

| | | | |
|---|---|---|---|
| 2008/0076960 A1* | 3/2008 | Marseille et al. | 600/16 |
| 2008/0243081 A1 | 10/2008 | Nance | |
| 2009/0023975 A1* | 1/2009 | Marseille et al. | 600/16 |
| 2009/0112050 A1* | 4/2009 | Farnan et al. | 600/16 |
| 2009/0182188 A1* | 7/2009 | Marseille et al. | 600/16 |
| 2010/0010500 A1 | 1/2010 | Beane et al. | |
| 2010/0160725 A1 | 6/2010 | Kiser et al. | |
| 2010/0185044 A1 | 7/2010 | Kassab et al. | |
| 2010/0198040 A1 | 8/2010 | Friedman et al. | |
| 2010/0249490 A1 | 9/2010 | Farnan | |
| 2010/0249491 A1* | 9/2010 | Farnan et al. | 600/16 |
| 2010/0249920 A1 | 9/2010 | Bolling et al. | |
| 2011/0054487 A1 | 3/2011 | Farnan | |
| 2011/0066170 A1 | 3/2011 | Farnan | |
| 2011/0112353 A1 | 5/2011 | Farnan et al. | |
| 2011/0112632 A1 | 5/2011 | Chau et al. | |
| 2011/0137234 A1 | 6/2011 | Farnan et al. | |
| 2011/0190697 A1* | 8/2011 | Farnan | A61M 25/0662 604/99.01 |
| 2011/0196190 A1* | 8/2011 | Farnan et al. | 600/16 |
| 2011/0196191 A1 | 8/2011 | Farnan et al. | |
| 2011/0200451 A1 | 8/2011 | Lehmann et al. | |
| 2012/0004496 A1 | 1/2012 | Farnan et al. | |
| 2012/0059213 A1 | 3/2012 | Spence | |
| 2012/0078032 A1 | 3/2012 | Spence | |
| 2012/0116317 A1 | 5/2012 | Kassab et al. | |
| 2012/0259157 A9* | 10/2012 | Spence | 600/16 |
| 2013/0060267 A1 | 3/2013 | Farnan et al. | |
| 2013/0116715 A1 | 5/2013 | Weber | |
| 2013/0150772 A1 | 6/2013 | Farnan et al. | |
| 2013/0172661 A1* | 7/2013 | Farnan | A61M 1/3653 600/16 |
| 2013/0231521 A1 | 9/2013 | Farnan | |

FOREIGN PATENT DOCUMENTS

| | | |
|---|---|---|
| WO | WO 97/42413 | 11/1997 |
| WO | WO 99/59652 | 11/1999 |
| WO | WO 01/80927 | 11/2001 |
| WO | WO 2005/037345 | 4/2005 |
| WO | WO 2007/047933 | 4/2007 |
| WO | WO 2008/027869 | 3/2008 |
| WO | WO 2009/045624 | 4/2009 |
| WO | WO 2009/055651 | 4/2009 |
| WO | WO 2012/033847 | 3/2012 |
| WO | WO 2013/022420 | 2/2013 |

OTHER PUBLICATIONS

Antaki, J. F. et al., "Development progress of the University of Pittsburgh streamliner: a mixed flow blood pump with magnetic bearings," ASAIO Journal, 46(2):194 (2000) (Abstract only).

Antaki, J. F. et al., "In vivo evaluation of the nimbus axial flow ventricular assist system: Criteria and methods," ASAIO Journal, 39:M231-M236 (1993).

Arrow International, Inc., AutoCAT™ 2WAVE™, Brochure, Arrow International, Inc. USA (2003), 4 pages.

Bachman, T. N., "Development and evaluation of the quintessential ventricular cannula," Thesis, University of Pittsburgh (2008), 71 pages.

Baird, R. J. et al., "Survey of mechanical assistance of the circulation and the present status of left-heart bypass," Canad. Med. Ass. J., 95:646-651 (1966).

Baird, R. J. et al., Le Support Mecanique Du Ventricule Gauche, L'Union Med. du Canada, Tome 93, pp. 258-268 (1964).

Brooks, S. G. et al., "The use of a latissimus dorsi myocutaneous flap to cover an axillobifemoral vascular prosthetic graft," Eur. J. Vasc. Surg., 3:367-368 (1989).

"Cannula-Tip Development for Minimal Invasive Pumps," Medizinische Universitate Wien, Center for Medical Physics and Biomedical Engineering as printed on Jan. 31, 2011.

Cavallaro, A. et al., "The effect of body weight compression on axillo-femoral by-pass patency," J. Cardiovasc. Surgery, 29:476-479 (1988).

Cochran, R. P. et al., "Ambulatory intraaortic balloon pump use as bridge to heart transplant," Ann. Thorac. Surg., 74:746-752 (2002).

Copeland, J. G. III, "Thromboembolism and bleeding: Clinical strategies," Ann. Thorac. Surg., 61:376-377 (1996).

Curtis, A. S. et al., "Novel ventricular apical cannula: in vitro evaluation using transparent, compliant ventricular casts," ASAIO Journal, 44:M691-M695 (1998).

Datascope, The CS100(TM) Intelligent Counterpulsation, Brochure (2003), 11 pages.

DeBakey, M. E., "The Artificial Heart", in The History of Surgery in Houston, Kenneth L. Mattox, ed., pp. 346-358 (1998).

Dennis, C. et al., "Clinical Use of a Cannula for Left Heart Bypass Without Thoracotomy: Experimental Protection Against Fibrillation by Left Heart Bypass," Annals of Surgery, 156(4):623-636 (1962).

Dennis, C. et al., "Reducation of the Utilization of the Heart by Left Heart Bypass," Circulation Research, Journal of the American Heart Association, 10:298-305 (1962).

Dennis, C. et al., "Left atrial cannulation without thoracotomy for total left heart bypass," Acta Chir Scand., 123:267-279 (1962).

El-Banayosy, A. et al., "Bridging to cardiac transplantation with the thoratec ventricular assist device," Thorac. Cardiovasc. Surg., 47:307-310 (1999).

Fraser, K. H. et al., "Computational fluid dynamics analysis of thrombosis potential in left ventricular assist device drainage cannulae," ASAIO Journal, 56(3):157-163 (2010).

Freed, P. S. et al., "Intraaortic balloon pumping for prolonged circulatory support," The American Journal of Cardiology, 61(8):554-557 (1988).

Greenberg, B. et al., "Effects of continuous aortic flow augmentation in patients with exacerbation of heart failure inadequately responsive to medical therapy: Results of the multicenter trial of the orgis medical cancion system for the enhanced treatment of heart failure unresponsive to medical therapy (momentum)," Circulation, 118:1241-1249 (2008).

Gristina, A. G. et al., "Biomaterial-centered sepsis and the total artificial heart," JAMA, 259:870-874 (1988).

Helman, D. N. et al., "Left ventricular assist device bridge-to-transplant network improves survival after failed cardiotomy," Ann. Thorac. Surg., 68:1187-1194 (1999).

Jaski, B. E. et al., "Diagnosis and treatment of complications in patients implanted with a TCI left ventricular assist device," Journal of Interventional Cardiology, 8(3):275-282 (1995).

Jeevanadam, V. et al., "Circulatory assistance with a permanent implantable IABP: Initial human experience," Circulation, 106(1):I-183-I-188 (2002).

Johnson, W. C. et al., "Is axillo-bilateral femoral graft an effective substitute for aortic-bilateral Iliac/femoral graft?: An analysis of ten years experience," Annals of Surgery, 186(2):123-129 (1977).

Kawahito, K. et al., "Ex vivo phase 1 evaluation of the DeBakey/NASA axial flow ventricular assist device," Artificial Organs, 20(1):47-52 (1996).

Kawai, A. et al., "Management of infections in mechanical circulatory support devices," Cardiac Surgery: State of the Art Reviews, 7(2):413-424 (1993).

Kirklin, J. K. et al., "Mechanical circulatory support: Registering a therapy in evolution," Circ. Heart Fail., 1:200-205 (2008).

Korfer, R. et al., "Temporary pulsatile ventricular assist devices and biventricular assist devices," Ann. Thorac. Surg., 68:678-683 (1999).

Kyo, S. et al., "Percutaneous Introduction of Left Atrial Cannula for Left Heart Bypass: Utility of Biplane Transesophageal Echocardiographic Guidance for Transseptal Puncture," Artificial Organs, 16(4):386-391 (1992).

Litwak, K. N. et al., "Retrospective analysis of adverse events in preclinical ventricular assist device experiments," ASAIO Journal, 54:1-4 (2008).

Macha, M. et al., "Survival for Up to Six Months in Calves Supported With an Implantable Axial Flow Ventricular Assist Device", ASAIO Journal, 43:311-315 (1997).

(56) References Cited

OTHER PUBLICATIONS

Magee, T. R. et al., "Reinforced vascular grafts: a comparative study," Eur. J. Vasc. Surg., 6:21-25 (1992).
Magovern, G. J. et al., "The biopump and postoperative circulatory support," Ann. Thorac. Surg., 55:245-249 (1993).
Manord, J. D. et al., "Implications for the vascular surgeon with prolonged (3 to 89 days) intraaortic balloon pump counterpulsation," J. Vasc. Surg., 26:511-516 (1997).
McBride, L. R. et al., "Clinical experience with 111 thoratec ventricular assist devices," Ann. Thorac. Surg., 67:1233-1239 (1999).
Meyns, B. et al., "Proof of Concept: Hemodynamic Response to Long-Term Partial Ventricular Support With the Synergy Pocket Micro-Pump," J. Am. Coll. Cardiol., 54(1):79-86 (2009).
Morales, D. L. S. et al., "Lessons learned from the first application of the DeBakey VAD child: An intracorporeal ventricular assist device for children," The Journal of Heart and Lung Transplantation, 24(3):331-337 (2005).
Mussivand, T. et al., "Progress with the heartsaver ventricular assist device," Ann. Thorac. Surg., 68:785-789 (1999).
Nanas, J. N. et al., "A valveless high stroke volume counterpulsation device restores hemodynamics in patients with congestive heart failure and intractable cardiogenic shock awaiting heart transplantation," The Journal of Thoracic and Cardiovascular Surgery, 111(1):55-61 (1996).
Nanas, J. N. et al., "Comparison of an implanted abdominal aortic counterpulsation device with the intraaortic balloon pump in a heart failure model," J. Am College Cardiology, 7(5):1028-1035 (1986).
Nanas, J. N. et al., "Effectiveness of a counterpulsation device implanted on the ascending aorta," Trans. Am. Soc. Artif. Intern. Organs, 33:203-206 (1987).
Nanas, J. N. et al., "Hemodynamic effects of a counterpulsation device implanted on the ascending aorta in severe cardiogenic shock," Trans. Am. Soc. Artif. Intern. Organs, 34:229-234 (1988).
Nanas, J. N. et al., "Preclinical evaluation of the abdominal aortic counterpulsation device," American Heart Journal, 116(4):1003-1008 (1998).
Nishimura, K. et al., "Results of Chronic Animal Experiments with a New Version of a Magnetically Suspended Centrifugal Pump", ASAIO Journal, 44:M725-M727 (1998).
Noon, G. P. et al., "Clinical experience with the micromed DeBakey ventricular assist device," Ann. Thorac. Surg., 71:S133-S138 (2001).
Nose, Y. et al., "Can we develop a nonpulsatile permanent rotary blood pump? Yes, we can," Artificial Organs, 20(6):467-474 (1996).
Ochiai, Y. et al., "In vivo hemodynamic performance of the cleveland clinic coraide blood pump in calves," Ann. Thorac. Surg., 72:747-752 (2001).
Ozawa, K. et al., "Inflow system for long-term ventricular assist device (LVAD)," In: Transactions American Society for Artificial Internal Organs, vol. XXVI, New Orleans, Louisiana, Apr. 17-19, 1980, pp. 24-28.
Park, J. K. et al., "Intraaortic balloon pump management of refractory congestive heart failure in children," Pediatric Cardiology, 14(1):19-22 (1993).
Petition to Request Inter Partes Reexamination of U.S. Pat. No. 6,530,876, filed on Dec. 19, 2011, 215 pages.

Reddy, R. C. et al., "End organ function with prolonged nonpulsatile circulatory support," ASAIO Journal, 41:M547-M551 (1995).
Rosenbaum, A. M. et al., "Intra-aortic balloon counterpulsation as a 'bridge' to cardiac transplantation. Effects in nonischemic and ischemic cardiomy opathy," Chest, 106(6):1683-1688 (1994).
Schmid, C. et al., "Influence of inflow cannula length in axial-flow pumps on neurologic adverse event rate: Results from a multi-center analysis," The Journal of Heart and Lung Transplantation, 27(3):253-260 (2008).
Slater, J. P. et al., "Low thromboembolic risk without anticoagulation using advanced-design left ventricular assist devices," Ann. Thorac Surg., 62:1321-1328 (1996).
Sunshine Heart, Inc. Prospectus, Underwriter Wilson HTM Corporate Finance Limited (2004), 116 pages.
Takami, Y. et al., "Anatomical Consideration for an Implantable Centrifugal Biventricular Assist System," Artificial Organs, 21(10):1132-1136 (1997).
Tayama, E. et al., "The DeBakey ventricular assist device: current status in 1997," Artificial Organs, 23(12):1113-1116 (1999).
Terrovitis, J. V. et al., "Superior performance of a paraaortic counterpulsation device compared to the intraaortic balloon pump," World Journal of Surgery, 27(12):1311-1316 (2003).
World Heart Corporation, World Heart, Annual Report (1998), 36 pages.
Zile, M. R. et al., "Progressive improvement in cardiac performance with continuous aortic flow augmentation (aortic flow therapy) in patients hospitalized with severe heart failure: Results of the multicenter trial of the orgis medical cancion system for the enhanced treatment fo heart failure unresponsive to medical therapy (momentum)," The Journal of Heart and Lung Transplantation, 29(1):86-92 (2010).
International Search Report for International Application No. PCT/US2001/040579, mailed Nov. 15, 2001, 4 pages.
International Preliminary Examination Report for International Application No. PCT/US2001/040579, dated Jul. 15, 2002, 7 pages.
Office Action for Australian Application No. 2011299232, issued Jan. 24, 2014, 3 pages.
International Search Report and Written Opinion for International Application No. PCT/US2011/050709, mailed Nov. 30, 2011, 13 pages.
Office Action for Chinese Application No. 201180051436.8, dated Feb. 15, 2015, 13 pages.
Office Action for U.S. Appl. No. 13/227,272, mailed Feb. 13, 2015, 18 pages.
International Search Report and Written Opinion for International Application No. PCT/US2013/065277, mailed Jan. 9, 2014, 11 pages.
International Search Report and Written Opinion for International Application No. PCT/US2014/068626, mailed Apr. 30, 2015, 12 pages.
Office Action for U.S. Appl. No. 13/227,272, mailed Dec. 2, 2015, 12 pages.
Office Action for Israel Application No. 225104, dated Mar. 27, 2016.
Supplementary Partial European Search Report mailed Sep. 21, 2016, in EP 13847192.5, 6 pages.

* cited by examiner

2590

```
Insert a tubular member into a body such that a connection
portion of the tubular member is at least partially within an
interior volume of an organ
2591
```

↓

```
Move the connection portion from a collapsed configuration to
an expanded configuration such that an outer edge of the
connection portion contacts a first portion of an inner surface of
a wall of the organ, thereby placing the interior volume of the
organ in fluid communication with the lumen and fluidically
isolating the interior volume of the organ from a volume outside
of the organ
2592
```

↓

```
Move a support member from a first configuration, in which an
end portion of the support member is disposed apart from the
inner surface of the wall, to a second configuration, in which the
end portion of the support member is in contact with a second
portion of the inner surface of the wall
2593
```

```
┌─────────────────────────────────────────────────────────┐
│ Insert a flow member, defining a first channel and a second │
│ channel, into a body such that a first end portion of the flow │
│ member is at least partially within an interior volume of an organ │
│                         2691                            │
└─────────────────────────────────────────────────────────┘
                            │
                            ▼
┌─────────────────────────────────────────────────────────┐
│ Move the first end portion from a collapsed configuration to an │
│ expanded configuration such that an outer edge of the first end │
│ portion contacts an inner surface of a wall of the organ, thereby │
│ placing the interior volume of the organ in fluid communication │
│         with the first channel and the second channel    │
│                         2692                            │
└─────────────────────────────────────────────────────────┘
                            │
                            ▼
┌─────────────────────────────────────────────────────────┐
│ Couple the second end portion of the flow member to a pump to │
│  place the first channel in fluid communication with an outlet of │
│     the pump, and to place the second channel in fluid   │
│          communication with an inlet of the pump         │
│                         2693                            │
└─────────────────────────────────────────────────────────┘
```

FIG. 45

DEVICES, SYSTEMS, AND METHODS FOR FACILITATING FLOW FROM THE HEART TO A BLOOD PUMP

CROSS-REFERENCE TO RELATED APPLICATIONS

This application claims priority to and the benefit of U.S. Provisional Patent Application Ser. No. 61/795,407 entitled, "Devices, Systems, and Methods to Optimize Flow From the Heart to a Blood Pump," filed Oct. 16, 2012 the disclosure of which is incorporated herein by reference in its entirety.

BACKGROUND

Embodiments described herein relate generally to apparatus and methods for optimizing flow of a bodily fluid, and more particularly, devices, systems, and methods to facilitate blood flow from the heart to a blood pump.

The use of devices to assist the function of an ailing heart is increasing. In some instances, a ventricular assist device (VAD) can be used to partially or completely replace the function of the heart. For example, in some instances, a left ventricular assist device (LVAD) can be used to assist a heart of a patient by placing an inlet flow cannula in fluid communication with the left ventricle of the heart and an outlet flow cannula in fluid communication with a portion of the aorta. The LVAD can include a pumping mechanism that can pump, transfer, draw, push, or otherwise produce a flow of blood between the inlet flow cannula and the outlet flow cannula, thereby assisting heart. The chamber of the left ventricle can be relatively large to act as a suitable source for blood pump inflow and the wall of the left ventricle is relatively thick to support the inlet flow cannula. Known methods for coupling an inlet flow cannula to the left ventricle, however, often require major surgery, which can damage the heart or surrounding tissue and/or can result in death of the patient. Such known procedures can also be relatively expensive due to long surgical times and/or the complexity and risk of the surgery. Furthermore, in some instances, the drawing of blood through the inlet flow cannula can produce a negative pressure within the left ventricle that can cause a wall of the left ventricle to collapse, thereby obstructing the inlet flow cannula and/or other veins.

In some instances, an inlet flow cannula can be placed in or at a desired location within, for example, the left atrium which can reduce the complexity, severity, risk, and/or cost of placing an assist device. In some such instances, the inlet flow cannula is advanced through the superior vena cava (SVC) and is coupled to the septum between the right atrium and the left atrium. In other instances, the inlet flow cannula can be coupled to the dome of the left atrium. Placing the inlet flow cannula in fluid communication with the left atrium, however, can be complicated by the anatomy of the heart. For example, the walls of the left atrium are very thin (e.g., between 1 and 2 mm in thickness) and the interior of the left atrium can be at a relatively low pressure, due to the function of the heart, which can increase the likelihood of tissue collapsing into the left atrium. Such a collapse of tissue can obstruct the inlet flow cannula and/or can result in undesirable kinking of veins in fluid communication with the left atrium. Thus, the inflow rates to the blood pump using such methods can be limited, which can result in poor efficiency of the pump and can result in clot formation.

Thus, a need exists for devices, systems, and methods to improve flow of blood from the heart to a blood pump.

SUMMARY

Devices, systems, and methods to optimize flow from the heart to a blood pump are described herein. In some embodiments, an apparatus includes a tubular member that defines a lumen therethrough and a channel, and a support member. The tubular member has a connection portion that is configured to be coupled to a wall of an organ. The connection portion is configured to move between a collapsed configuration and an expanded configuration. An outer edge of the connection portion is configured to contact a first portion of an inner surface of the wall when the connection portion is in its expanded configuration such that an interior volume of the organ is in fluid communication with the lumen and is fluidically isolated from a volume outside of the organ. The support member is movably disposed within the channel and is configured to minimize movement of the wall relative to the tubular member. The support member is configured to move between a first configuration and a second configuration. An end portion of the support member is disposed within the channel when the support member is in the first configuration. The end portion of the support member configured to contact a second portion of the inner surface of the wall when the support member is in its second configuration.

BRIEF DESCRIPTION OF THE DRAWINGS

FIG. 44 is a flow chart illustrating a method of coupling an inlet flow cannula assembly to a wall of an organ according to an embodiment.

FIG. 45 is a flow chart illustrating a method of coupling a flow member to a wall of an organ according to an embodiment.

DETAILED DESCRIPTION

Figure 1:
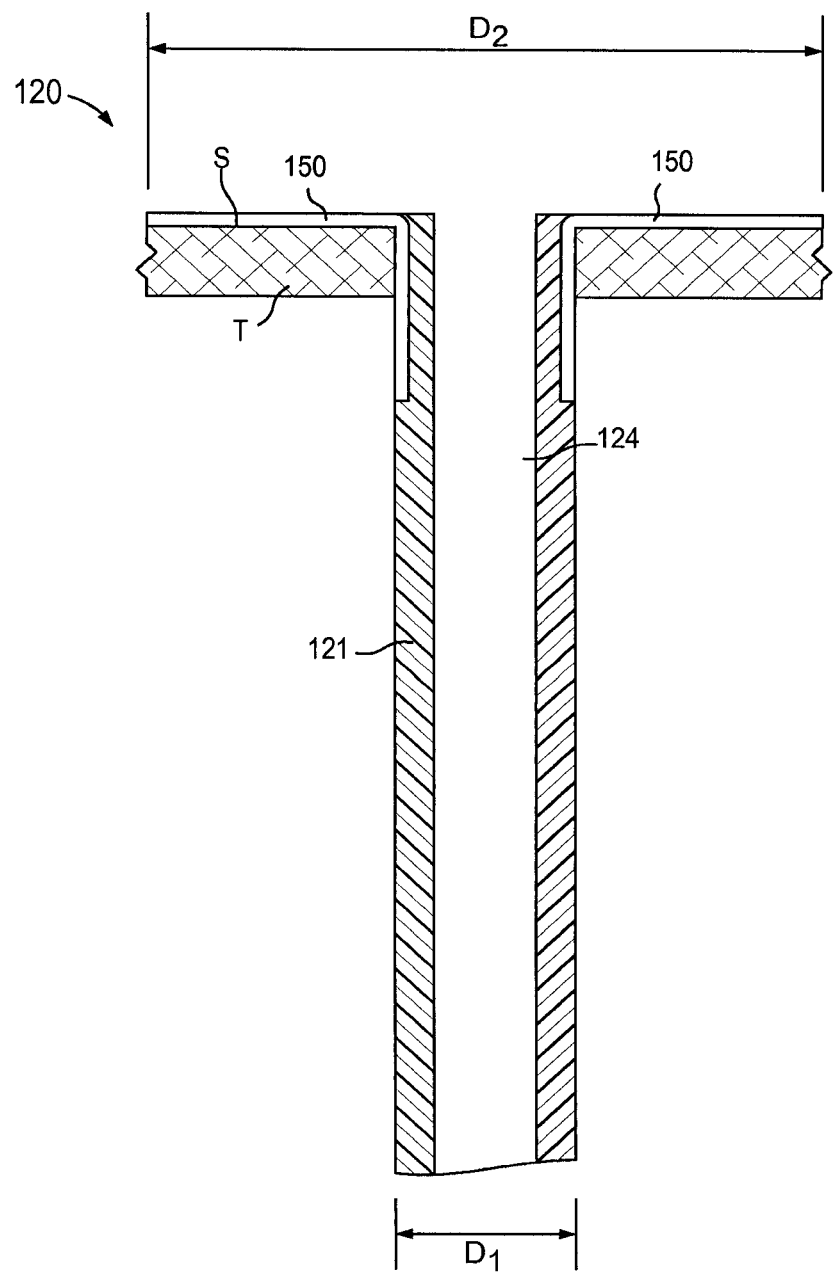
FIG. 1 is a schematic illustration of a portion of an inlet flow cannula assembly according to an embodiment.

In some embodiments, an apparatus includes a tubular member that defines a lumen therethrough, and a support member coupled to the tubular member. The tubular member has a connection portion that is configured to be coupled to a wall of an organ to place an interior volume of the organ in fluid communication with the tubular member. The support member is configured to be transitioned between a collapsed configuration and an expanded configuration such that, when in the expanded configuration, a size of the support member is at least three times greater than a diameter of the tubular member. The support member is config- ured to minimize movement and/or deformation of the wall of the organ relative to the tubular member when in the expanded configuration.

In some embodiments, an apparatus includes a tubular member that defines a lumen therethrough, and a support member coupled to the tubular member. The tubular member has a connection portion that is configured to transition from a collapsed configuration to an expanded configuration. The connection portion is such that, when in its expanded configuration, at least an outer edge of the connection portion is in contact with a first portion of an inner surface of a wall of an organ to place an interior volume of the organ in fluid communication with the lumen. The support member is configured to transition between a collapsed configuration and an expanded configuration to minimize movement and/ or deformation of the wall relative to the tubular member. The support member is such that, when in its expanded configuration, the support member is in contact with a second portion of the inner surface of the wall. The connection portion and the support member collectively maintain continuous contact between the outer edge of the connection portion and the first portion of the inner surface of the wall.

In some embodiments, an apparatus includes a tubular member that defines a lumen therethrough and a channel, and a support member coupled to the tubular member. The tubular member has a connection portion that is configured to transition from a collapsed configuration to an expanded configuration. The connection portion is such that, when in its expanded configuration, at least an outer edge of the connection portion is in contact with a first portion of an inner surface of a wall of an organ to place an interior volume of the organ in fluid communication with the lumen. The support member is movably disposed within the channel and is configured to transition between a first configuration and a second configuration to minimize movement and/or deformation of the wall relative to the tubular member. The support member includes an end portion that is disposed within the channel when the support member is in the first configuration. The end portion is configured to contact a second portion of the inner surface of the wall when the support member is in its second configuration.

In some embodiments, a method includes inserting a tubular member into a body such that a connection portion of the tubular member is at least partially within an interior volume of an organ. The connection portion is moved from a collapsed configuration to an expanded configuration such that an outer edge of the connection portion contacts a first portion of an inner surface of a wall of the organ, thereby placing the interior volume of the organ in fluid communication with the lumen while fluidically isolating the interior volume of the organ from a volume outside of the organ. A support member is moved from a first configuration to a second configuration. An end portion of the support member is disposed apart from the inner surface of the wall when the support member is in the first configuration. The end portion of the support member is in contact with a second portion of the inner surface of the wall when the support member is in the second configuration.

In some embodiments, the method optionally includes moving the support member within a channel defined by the tubular member from a first position to a second position to limit movement of the wall relative to the tubular member.

In some embodiments, a method includes inserting a flow member, defining a first channel and a second channel, into a body such that a first end portion of the flow member is at least partially within an interior volume of an organ. The first end portion is moved from a collapsed configuration to an expanded configuration such that an outer edge of the first end portion contacts an inner surface of a wall of the organ, thereby placing the interior volume of the organ in fluid communication with the first channel and the second channel. The second end portion of the flow member is coupled to a pump to place the first channel in fluid communication with an outlet of the pump, and to place the second channel in fluid communication with an inlet of the pump. In some embodiments, the method includes actuating the pump such that a first flow of a fluid flows from the interior volume of the organ to the pump via the second channel, and a second flow of the fluid flows from the pump to the interior volume of the organ via the first channel.

In some embodiments, an apparatus includes a flow member defining a first channel and a second channel. The flow member including a first end portion and a second end portion. The first end portion is configured to move from a collapsed configuration to an expanded configuration. An outer edge of the first end portion is configured to contact an inner surface of a wall of an organ when the first end portion is in its expanded configuration such that an interior volume of the organ is in fluid communication with the first channel and the second channel. The second end portion of the flow member is configured to be coupled to a pump such that the first channel is in fluid communication with an outlet of the pump and the second channel is in fluid communication with an inlet of the pump.

As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof.

As used herein, the words "proximal" and "distal" refer to direction closer to and away from, respectively, an operator of a medical device. Thus, for example, the end of the device contacting the patient's body would be the distal end of the device, while the end opposite the distal end would be the proximal end of the device. Moreover, a portion of an anatomical structure can be considered as a reference to describe a position closer to or away from the portion of the anatomical structure. For example, an end of the superior vena cava that is closest to the heart would be the proximal end of the superior vena cava, while the end opposite the proximal end would be the distal end.

As used herein, the term "set" can refer to multiple features or a singular feature with multiple parts. For example, when referring to a set of walls, the set of walls can be considered as one wall with multiple portions, or the set of walls can be considered as multiple, distinct walls. Thus, a monolithically constructed item can include a set of walls. Such a set of walls may include multiple portions that are either continuous or discontinuous from each other. A set of walls can also be fabricated from multiple items that are produced separately and are later joined together via any suitable method.

As used herein, the terms "about" and "approximately" generally mean plus or minus 10% of the value stated. For example, about 0.5 would include 0.45 and 0.55, about 10 would include 9 to 11, about 1000 would include 900 to 1100.

As used herein, the term "substantially" when used in connection with "cylindrical," "linear," and/or other geometric relationships is intended to convey that the structure so defined is nominally cylindrical, linear or the like. As one example, a portion of a support member that is described as being "substantially linear" is intended to convey that, although linearity of the portion is desirable, some non-linearity can occur in a "substantially linear" portion. Such non-linearity can result from manufacturing tolerances, or other practical considerations (such as, for example, the pressure or force applied to the support member). Thus, a geometric construction modified by the term "substantially" includes such geometric properties within a tolerance of plus or minus 5% of the stated geometric construction. For example, a "substantially linear" portion is a portion that defines an axis or center line that is within plus or minus 5% of being linear.

As used herein, the term "parallel" generally describes a relationship between two geometric constructions (e.g., two lines, two planes, a line and a plane or the like) in which the two geometric constructions are substantially non-intersecting as they extend substantially to infinity. For example, as used herein, a line is said to be parallel to another line when the lines do not intersect as they extend to infinity. Similarly, when a planar surface (i.e., a two-dimensional surface) is said to be parallel to a line, every point along the line is spaced apart from the nearest portion of the surface by a substantially equal distance. Two geometric constructions are described herein as being "parallel" or "substantially parallel" to each other when they are nominally parallel to each other, such as for example, when they are parallel to each other within a tolerance. Such tolerances can include, for example, manufacturing tolerances, measurement tolerances, surface variation tolerances, or the like.

As used herein, the term "stiffness" relates to an object's resistance to deflection, deformation, and/or displacement by an applied force. For example, a wire or support member with greater stiffness is more resistant to deflection, deformation, and/or displacement when exposed to a force than a wire or support member with lower stiffness. Similarly stated, a support member with higher stiffness can be characterized as being more rigid than a support member with lower stiffness. In some embodiments, the stiffness of an object can be characterized by the object's linear stiffness. Linear stiffness can be characterized in terms of the amount of force applied to the object and the resulting distance through which a first portion of the object deflects, deforms, and/or displaces with respect to a second portion of the object. When characterizing the linear stiffness of an object, the deflected distance may be measured as the deflection of a portion of the object different from the portion of the object to which the force is directly applied. Said another way, in some objects, the point of deflection is distinct from the point where force is applied.

Stiffness is an extensive property of the object being described, and thus is dependent upon the material from which the object is formed and certain physical characteristics of the object (e.g., shape and boundary conditions). For example, the stiffness of an object can be increased or decreased by selectively including in the object a material having a desired modulus of elasticity. The modulus of elasticity is an intensive property of the constituent material and describes an object's tendency to elastically (i.e., non-permanently) deform in response to an applied force. A material having a high modulus of elasticity will not deflect as much as a material having a low modulus of elasticity in the presence of an equally applied force. Thus, the stiffness of the object can be increased, for example, by introducing into the object and/or constructing the object of a material having a high modulus of elasticity. In another example, the stiffness of the object can be increased or decreased by changing the flexural modulus of a material of which the object is constructed. Flexural modulus is used to describe the ratio of the applied stress on an object in flexure to the corresponding strain in the outermost portions of the object. The flexural modulus, rather than the modulus of elasticity, is used to characterize certain materials, for example plastics, that do not have material properties that are substantially linear over a range of conditions. An object with a first flexural modulus is less elastic and has a greater strain on the outermost portions of the object than an object with a second flexural modulus lower than the first flexural modulus. Thus, the stiffness of an object can be increased by including in the object a material having a high flexural modulus.

The stiffness of an object can also be increased or decreased by changing a physical characteristic of the object, such as the shape or cross-sectional area of the object. For example, an object having a length and a cross-sectional area may have a greater stiffness than an object having an identical length but a smaller cross-sectional area. Thus, the stiffness of the object can be increased by increasing and/or changing the shape of the cross-sectional area of the object.

The embodiments described herein are structures configured to be disposed within a portion of the body of a patient. As such, the embodiments can be formed or constructed of one or more biocompatible materials. Examples of suitable biocompatible materials include metals, glasses, ceramics, or polymers. Examples of suitable metals include pharmaceutical grade stainless steel, gold, titanium, nickel, iron, platinum, tin, chromium, copper, and alloys thereof. The polymer may be biodegradable or non-biodegradable. Examples of suitable biodegradable polymers include polylactides, polyglycolides, polylactide-co-glycolides (PLGA), polyanhydrides, polyorthoesters, polyetheresters, polycaprolactones, polyesteramides, poly(butyric acid), poly(valeric acid), polyurethanes and copolymers and blends thereof. Examples of non-biodegradable polymers include nylons, polyesters, polycarbonates, polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, blends and copolymers thereof. Moreover, any of the embodiments described here can be formed from a material that can, for example, facilitate ingrowth of bodily tissue about a portion of the structure. Thus, the embodiments, can be formed from, for example, a base material and coated with a material configured to facilitate ingrowth of bodily tissue such as, for example, polyesters (polyethylene terephthalate (PET) or Dacron®), silicone, and/or the like. Similarly, the embodiments described herein can include any suitable surface finish that facilitates ingrowth of bodily tissue. For example, any of the embodiments described herein can have an outer surface that can be rough, pitted, scored, scratched, etc.

The embodiments and methods described herein can be used to facilitate the coupling of a flow device to a target tissue and, once coupled, provide support to the target tissue to minimize movement of at least a portion of the target tissue relative to the device. Any of the cannula assemblies and/or methods associated therewith described herein, can be used as an inflow cannula for a ventricular assist device system (referred to herein as a "VAD"), and can be at least partially implanted into a portion of the body of a patient to assist the function of the heart. Similarly, any of the embodiments and/or methods described herein can be used to support a wall of the heart to limit and/or prevent a collapse or partial collapse of the wall that could otherwise lead to the obstruction of an inlet cannula of the VAD and/or of vascular openings defined by the wall of the heart. For example, any of the embodiments and/or methods described herein can be used with or in any of the assist devices described below (e.g., the VAD 300) or in U.S. Pat. No. 6,530,876 entitled, "Supplemental Heart Pump Methods and Systems for Supplementing Blood Through the Heart," issued Mar. 11, 2003 and/or those described in U.S. Patent Publication No. 2012/0259157 entitled, "Cannula Systems and Methods," filed Oct. 11, 2012, the disclosures of which are incorporated herein by reference in their entireties.

FIG. 1 is a schematic illustration of a cannula assembly 120 coupled to a target tissue T, according to an embodiment. The target tissue T can be any suitable bodily tissue such as, for example, a wall or other structure of the heart, a wall of a vascular structure, and/or the like. For example, in some instances, the target tissue T can be a wall of a left atrium of a heart. The wall of the left atrium can define at least a portion of an interior volume I such that an exterior surface of the wall is fluidically isolated from an interior surface of the wall.

The cannula assembly 120 includes a tubular member 121 and a support member 150. The tubular member 121 can be, for example, a cannula or catheter that defines a lumen 124. The lumen 124 extends substantially through a distal surface and a proximal surface of the tubular member 121 such that, when the cannula assembly 120 is coupled to the target tissue T, the lumen 124 is placed in fluid communication with the interior volume I defined by the target tissue T (e.g., an interior volume of an organ and/or vascular structure). The tubular member 121 can be any suitable shape, size, or configuration. For example, the tubular member 121 can be substantially cylindrical, substantially polygonal (e.g., square, rectangular, pentagonal, octagonal, etc.), and/or a combination thereof. In some embodiments, the tubular member 121 can be substantially cylindrical and can define an outer diameter $D_1$, as shown in FIG. 1. As described in further detail herein, in some embodiments, the tubular member 121 can be transitioned from a first configuration (e.g., a collapsed configuration) to a second configuration (e.g., an expanded configuration) to couple the cannula assembly 120 to the target tissue T.

An end portion of the tubular member 121 is configured to be coupled to a pump (not shown in FIG. 1), and thus, in some embodiments, the cannula assembly 120 can function as an inflow cannula. Similarly stated, in use, an end portion of the tubular member 121 can be coupled to a pump, thus placing the pump in fluid communication with the interior volume I defined by the target tissue T via the lumen 124. In this manner, the cannula assembly 120 can be used to facilitate the placement of a ventricular assist device system (referred to herein as a "VAD") that can be at least partially implanted into a portion of the body of a patient to assist the function of the heart.

The support member 150 of the cannula assembly 120 is coupled to the tubular member 121. In some embodiments, the support member 150 can be monolithically formed with the tubular member 121. In other embodiments, the support member 150 can be disposed within a portion of the tubular member 121 (e.g., within the lumen 124). In still other embodiments, the support member 150 can substantially circumscribe (e.g., can be wrapped about) a portion of the tubular member 121. The support member 150 can be any suitable shape, size, or configuration. For example, in some embodiments, the support member 150 can be a wire or the like that can be formed from any suitable material such as, for example, nickel-titanium alloy (Nitinol®), stainless steel, plastic, composite, and/or any other biocompatible material. As described in further detail herein, the support member 150 can be transitioned from a first configuration (e.g., a collapsed configuration) to a second configuration (e.g., an expanded configuration) to be placed in contact with a surface S of the target tissue T, thereby limiting movement of the target tissue T relative to the tubular member 121.

As described above, the cannula assembly 120 is configured to be coupled to a target tissue T. In some embodiments, the tubular member 121 can include a connection portion and/or the like (not shown in FIG. 1) that can couple the cannula assembly 120 to the target tissue T. In some embodiments, the connection portion can include one or more retention members that are configured to engage the target tissue T to couple the cannula assembly 120 to the target tissue T. For example, in some instances, the target tissue T can be incised and the cannula assembly 120 can be advanced relative to the target tissue T to insert at least a distal end portion of the cannula assembly 120 through the incision into the target tissue T. More specifically, the support member 150 can be in its first configuration to allow the distal end portion of the cannula assembly 120 to be advanced through the incision formed in the target tissue T. Once the distal end portion of the cannula assembly 120 is inserted through the incision defined by the target tissue T, the tubular member 121 can be coupled to the target tissue. In this manner, the connection portion and/or the tubular member 121 can be placed into contact with a surface S or any other suitable portion of the target tissue T. In some embodiments, a surface of the tubular member 121 can be maintained in continuous contact with the surface S of the target tissue T, thereby reducing the likelihood of clot formation.

In some embodiments, the support member 150 can be transitioned to its second configuration (as shown in FIG. 1) after the tubular member 121 is coupled to the target tissue T. For example, in some embodiments, the transitioning of the tubular member 121 from its first configuration to its second configuration can urge the support member 150 to transition from its first configuration to its second configuration at substantially the same time. In other embodiments, the support member 150 is transitioned from its first configuration to its second configuration independently from the coupling of the tubular member 121 to the target tissue T.

In some embodiments, when in its second configuration, at least a portion of the support member 150 can be placed in continuous contact with the surface S of the target tissue T. Similarly stated, in some embodiments, substantially an entire surface of the support member 150 that is adjacent to the target tissue T is in contact therewith. For example, as shown in FIG. 1, the surface of the support member 150 that is against (or facing) the inner surface S of the target tissue T is in contact with the inner surface S of the target tissue T without areas of the support member 150 being spaced apart from the inner surface S. This arrangement can limit the formation of clots in those embodiments in which the target tissue T includes blood (e.g., the heart). More particularly, by limiting the portion of the support member 150 that is suspended within the interior volume I of the organ, clot formation can be reduced. In some embodiments, for example, the support member 150 can be a wire or the like that can form, for example, a spiral (e.g., a substantially planar spiral) or helix (e.g., substantially nonplanar) that is configured to be in continuous contact with the surface S. In other embodiments, the support member 150 can be a mesh or the like that is configured to be in continuous contact with the surface S.

By maintaining the support structure 150 and the tubular member 121 in continuous contact with the surface S, the likelihood of clot formation is reduced. The arrangement of the support member 150 and the tubular member 121 can also reduce eddy currents near the surface S of the target tissue T that would otherwise limit flow of blood to portions of the surface S and thereby increase the risk of clot formation. In addition, any portion of the tubular member 121 and/or the support member 150 can include an outer surface and/or surface finish configured to reduce clot formation and/or increase tissue ingrowth. For example, in some embodiments, at least a portion of the tubular member 121 and/or the support member 151 can be substantially circumscribed by a fabric and/or outer surface such as Dacron®, polyester, polytetrafluoroethylene (PTFE), silicon, polypropylene, and/or the like. In some embodiments, at least a portion of the tubular member 121 and/or the support member 150 can be coated by a biological material such as human tissue cells and/or animal tissue cells. In some embodiments, the outer surface of at least a portion of the tubular member 121 and/or the support member 150 can include a rough texture configured to encourage tissue ingrowth. Thus, bodily tissue can form about at least a portion of the tubular member 121 and/or the support member 150 which can reduce the likelihood of clot formation.

Although the support member 150 is shown as being in continuous contact with the inner surface of the target tissue T, in other embodiments, portions of the support member 150 can be spaced apart from the surface of the target tissue T. For example, in some embodiments, the support member 150 can be configured such that at least 90% of a surface of the support member 150 is in contact with the surface S; at least 80% of a surface of the support member 150 is in contact with the surface S; at least 70% of a surface of the support member 150 is in contact with the surface S; at least 60% of a surface of the support member 150 is in contact with the surface S; or at least 50% of a surface of the support member 150 is in contact with the surface S. In some embodiments, the cannula assembly can include a fabric interface or member (not shown in FIG. 1) to promote contact and/or tissue ingrowth between the support member 150 and the inner surface S of the target tissue T.

When in its second (or expanded) configuration, the support member 150 can have a size (e.g., an overall diameter and/or footprint) $D_2$ that is larger than the outer diameter $D_1$ of the tubular member 121. Similarly stated, the support member 150 can have the size $D_2$ that is defined by a radial distance between one side of the support member 150 to an opposite side of the support member 150. For example, in some embodiments, the support member 150 can form a helix that has a size $D_2$ that is associated with a diameter of the helix formed by the support member 150 (e.g., twice the distance in a radial direction from a longitudinal centerline defined by the helix and a point along an outer surface of the helix formed by the support member 150, that is to say twice the radius of the helix).

In some embodiments, the size $D_2$ of the support member 150 when in its second configuration can be about three times greater than the outer diameter $D_1$ of the tubular member 121. In this manner, the support member 150 can limit movement and/or deformation of portions of the tissue T that surround the lumen 124, thus limiting or preventing such portions from collapsing or being suctioned into the lumen 124 during use. Similarly stated, the ratio between the size $D_2$ of the support member 150 and the outer diameter $D_1$ can facilitate maintain the shape and/or size of the target tissue during use of the cannula assembly 120. More particularly, the support member 150 is configured to increase a surface area of the cannula assembly 120 that is in contact with the surface S of the target tissue T when in its second configuration. Moreover, the support member 150 can exert a force on the surface S of the target tissue T such that deflection of any portion of the support member 150 and/or the tubular member 121 away from the surface S is limited and/or substantially eliminated. Thus, the support member 150 can stabilize, support, and/or otherwise limit movement of the target tissue T relative to the tubular member 121 which can prevent, for example, a collapse and/or partial collapse of the target tissue T that can otherwise lead to obstruction of the lumen 124 defined by the tubular member 121 and/or of vascular openings defined by the target tissue T. In other words, the support member 150 can support the target tissue T to prevent a suction event in which a portion of the target tissue T obstructs the lumen 124

In other embodiments, the size $D_2$ of the support member 150 when in its second configuration can be greater than about three times the size of the outer diameter $D_1$. In yet other embodiments, the size $D_2$ of the support member 150 when in its second configuration can be about 1.1 times the size of the outer diameter $D_1$, about 1.2 times the size of the outer diameter $D_1$, about 1.3 times the size of the outer diameter $D_1$, about 1.4 times the size of the outer diameter $D_1$, about 1.5 times the size of the outer diameter $D_1$, about two times the size of the outer diameter $D_1$, about 2.5 times the size of the outer diameter D1, and/or the like.

Figure 2:
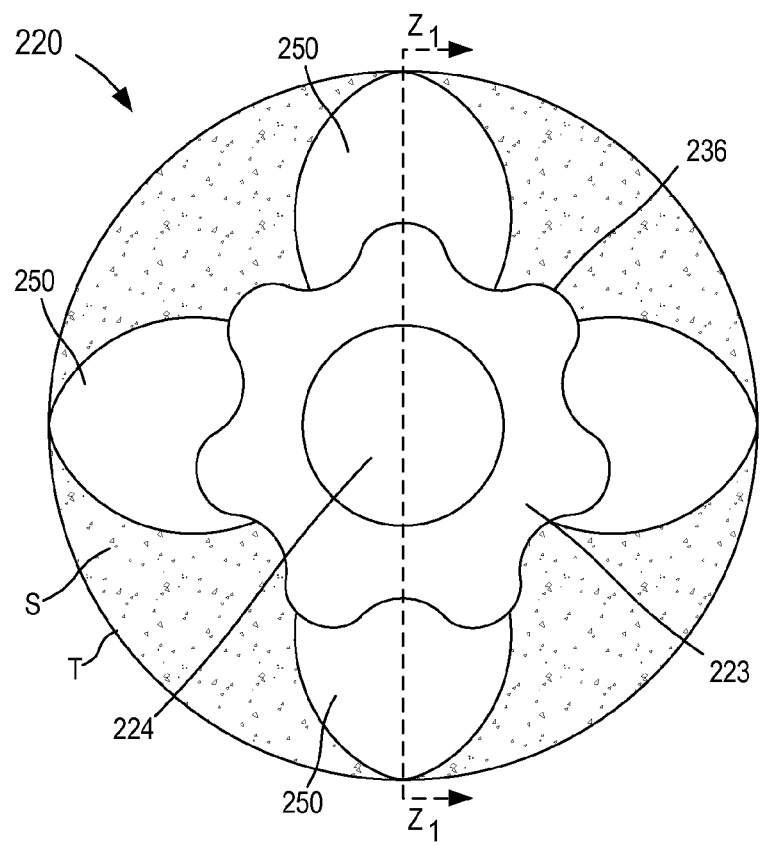
FIG. 2 is a top view illustration of a portion of an inlet flow cannula assembly coupled to a target tissue according to an embodiment.
Figure 3:
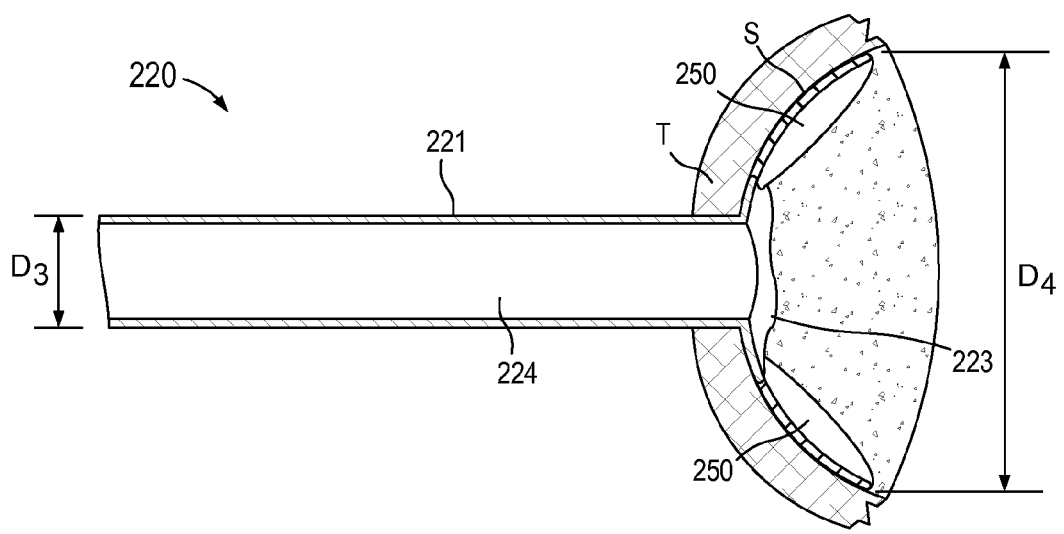
FIG. 3 is a cross-sectional illustration of a portion of the inlet flow cannula assembly of FIG. 2 coupled to the target tissue taken along the line $Z_1$-$Z_1$.

In some embodiments, a cannula assembly can include a connection or "anchoring" portion and a support member. For example, FIGS. 2 and 3 are schematic illustrations of a cannula assembly 220 coupled to a target tissue T, according to an embodiment. The target tissue T can be any suitable bodily tissue such as, for example, a wall or other structure of the heart, a wall of a vascular structure, and/or the like. For example, in some instances, the target tissue T can be a wall of a left atrium of a heart. The wall of the left atrium can define at least a portion of an interior volume such that an exterior surface of the wall is fluidically isolated from an interior surface of the wall.

The cannula assembly 220 includes a tubular member 221 and a support member 250. The tubular member 221 can be, for example, a cannula or catheter that defines a lumen 224. The lumen 224 extends substantially through a distal surface and a proximal surface of the tubular member 221 such that, when the cannula assembly 220 is coupled to the target tissue T, the lumen 224 is placed in fluid communication with an interior volume (not shown in FIG. 2) defined by the target tissue T (e.g., an interior volume of an organ and/or vascular structure). The tubular member 221 can be any suitable shape, size, or configuration. For example, the tubular member 221 can be substantially cylindrical, substantially polygonal (e.g., square, rectangular, pentagonal, octagonal, etc.), and/or a combination thereof. In some embodiments, the tubular member 221 can be substantially cylindrical and can define an outer diameter $D_3$ (see e.g., FIG. 3).

The tubular member 221 can be transitioned from a first configuration (e.g., a collapsed configuration) to a second configuration (e.g., an expanded configuration, as shown in FIGS. 2 and 3) to couple the cannula assembly 220 to the target tissue T. For example, as shown in FIGS. 2 and 3, the tubular member 221 includes a distal end portion 223 that extends outward when the tubular member 221 is in its second configuration. In this manner, at least an outer edge 236 of the distal end portion 223 (also referred to herein as a "connection portion") can be placed in contact with a first portion of a surface S of the target tissue. Although not shown in FIGS. 2 and 3, the distal end portion 223 can include one or more retention members and/or the like that are configured to engage a portion of the target tissue T such that at least the outer edge 236 of the distal end portion 223 is maintained in continuous contact with the first portion of the surface S, as described above with reference to FIG. 1. By maintaining continuous contact with the target tissue, the formation of clots adjacent the lumen 224 can be limited.

The support member 250 of the cannula assembly 220 is coupled to the tubular member 221 and is configured to be transitioned from a first configuration (e.g., a collapsed configuration) to a second configuration (e.g., an expanded configuration) to be placed in contact with the surface S of the target tissue T. In this manner, as described herein, the support member can stabilize the target tissue, maintain the shape of the target tissue and/or limit movement of the target tissue relative to the tubular member 221. Similarly stated, the support member 250 can facilitate flow of a fluid (e.g., blood) from the organ (e.g., the heart) via the lumen 224 by maintaining the position and/or shape of the organ (e.g., preventing a portion of the target tissue T from being sucked into the lumen 224).

In some embodiments, the support member 250 can be monolithically formed with the tubular member 221. In other embodiments, the support member 250 can be constructed separately from the tubular member 221. For example, the support member 250 can be disposed within a portion of the tubular member 221 (e.g., within the lumen 224 or a channel (not shown in FIGS. 2 and 3)). In still other embodiments, the support member 250 can substantially circumscribe a portion of the tubular member 221. The support member 250 can be any suitable shape, size, or configuration. For example, as shown in FIG. 2, the support member 250 can include a set of lobes or petals that can be, for example, unfolded to transition the support member 250 from the first configuration to the second configuration. Although shown in FIGS. 2 and 3 as including a set of four lobes, in other embodiments, the support member 250 can include any number of lobes of any suitable shape, size, or configuration. For example, in some embodiments, a support member can include two or three lobes that can be arranged in any suitable orientation relative to the tubular member 221. In other embodiments, a support member can include more than four lobes (e.g., five, six, seven, eight, nine, ten, etc.).

Moreover, while the lobes are shown as having a substantially uniform shape and size, in other embodiments, a support member can include a set of lobes of varying shape and/or size. For example in some embodiments, the support member 250 can include a first petal having a first shape and a second petal having a second shape different from the first shape. Such different shapes and/or sizes can allow the support member 250 to be tailored to accommodate a particular portion of the anatomy. For example, in some embodiments, the cannula assembly 220 can be coupled to a left atrium and the support member 250 can include first petal configured to contact a first portion of the atrial wall and a second petal configured to contact a second portion of the atrial wall adjacent the inlet from a pulmonary vein. In such embodiments, the second petal can have a size and/or shape configured to avoid obstruction of the pulmonary vein.

As described above with reference to the tubular member 221, when in its second configuration, the lobes of the support member 250 can be placed in continuous contact with the surface S of the target tissue T. When in its second configuration, the lobes of the support member 250 can have a size (e.g., a diameter) $D_4$ that is larger that the outer diameter $D_3$ of the tubular member 221. Therefore, the support member 250 is configured to increase a surface area of the cannula assembly 220 that is in continuous contact with the surface S of the target tissue T when in its second configuration. Moreover, the support member 250 can exert a force on the surface S of the target tissue T such that deflection of any portion of the support member 250 and/or the tubular member 221 away from the surface S is limited and/or eliminated. For example, in use a surface of each lobe of the support member 250 can be in continuous contact with the surface S of the target tissue T (e.g., substantially the entire surface of each lobe) and can exert a substantially uniform force that maintains the surface of each lobe in contact with the surface S. The arrangement of the distal end portion 223 of the tubular member 221 and the support member 250 is such that the force exerted by the support member 250 on the surface S maintains at least the outer edge 236 of the distal end portion 223 of tubular member 221 in contact with the surface S. By maintaining the support structure 250 and at least the outer edge 236 of the tubular member 221 in continuous contact with the surface S, the likelihood of clot formation is reduced. Furthermore, the arrangement of the support member 250 and the tubular member 221 can reduce eddy currents or other regions of flow stagnation near the surface S of the target tissue T that would otherwise limit flow of blood to portions of the surface S and thereby increase the risk of clot formation. In addition, any portion of the tubular member 221 and/or the support member 250 can include an outer surface and/or surface finish configured to reduce clot formation and/or increase tissue ingrowth, as described herein.

Thus, the support member 250 can stabilize, support, and/or otherwise limit movement of the target tissue T relative to the tubular member 221, which can prevent, for example, a collapse and/or partial collapse of the target tissue T that can otherwise lead to obstruction of the lumen 224 defined by the tubular member 221 and/or of vascular openings defined by the target tissue T. In instances where the cannula assembly 220 is used in conjunction with a ventricular assist device, the support member can expand the left atrium, resist collapse and distortion of the atrium, and, as a result, facilitate more inflow from the pulmonary veins. Thus, VAD systems that employ the cannula assembly 220 (or any of the other cannula assemblies described herein) can produce a higher flow rate of blood from the heart to the circulation system with a reduced amount of suction through the inlet flow cannula.

Figure 4:
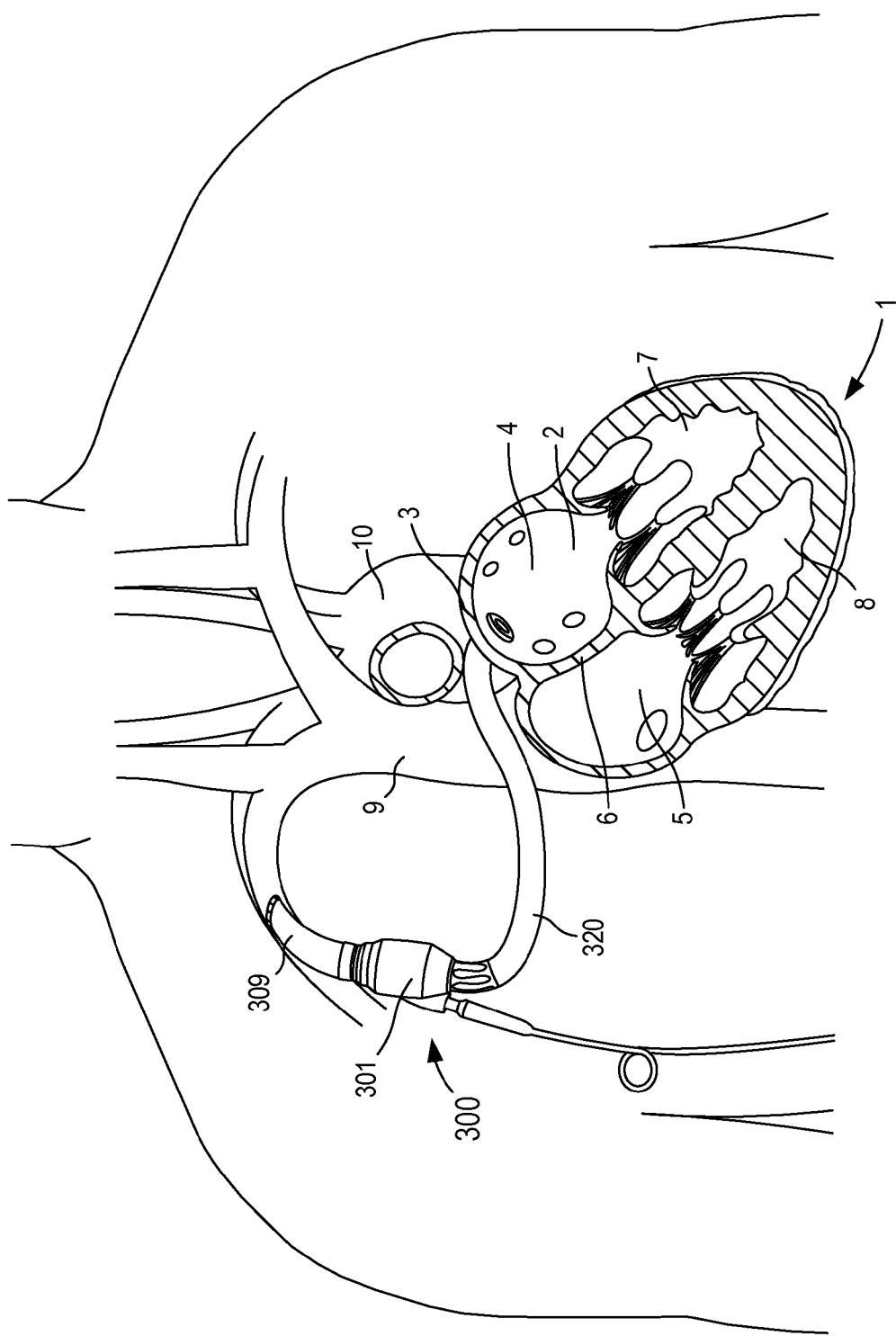
FIG. 4 is an illustration of an assist device in place within a portion of a body of a patient according to an embodiment.

FIG. 4 illustrates a VAD 300 that is in fluid communication with a heart 1, and that can include any of the inflow cannula assemblies described herein. For reference and as shown in FIG. 4, the heart 1 includes and/or otherwise defines a left atrium 2, a right atrium 5, a left ventricle 7 and a right ventricle 8. The left atrium 2 and the right atrium 5 are separated by a septum 6. The left atrium 2 includes a wall 3 that defines a dome of the left atrium 2. The heart 1 is in fluid communication with the superior vena cava 9 (which provides blood flow into the right atrium 5) and the aorta 10 (which receives blood flow from the left ventricle 7). The heart 1 is described herein for reference and is not meant to be an exhaustive description of the heart 1. Therefore, the simplified discussion of the heart 1 is provided for context as it pertains to the embodiments described herein.

The VAD 300 includes a pump 301, an outlet flow cannula 309, and an inlet flow cannula 320. In some instances, the VAD 300 can be placed in fluid communication with the heart 1 during a surgical procedure. That is to say, the inlet flow cannula 320 (or any of the cannula assemblies described herein) is introduced via a thorocotomy or other surgical procedure. In other embodiments, the inlet flow cannula 320 can be introduced via a non-surgical or "interventional" approach. For example, in some embodiments, the inlet flow cannula 320 (or any of the cannula assemblies described herein) is introduced into the left atrium 2 via a vein or artery such as the jugular vein, pulmonary vein, femoral artery, radial artery, superior vena cava, aorta, etc. (see e.g., the VAD system 400 shown in FIG. 5).

The pump 301 included in the VAD 300 can be any suitable pump. For example, the pump 301 can be, for example, a high flow impeller pump and/or the like. In other embodiments, the pump 301 can be any suitable pulsatile pump. The outlet flow cannula 309 can be, for example, a graft (e.g., a Dacron® graft and/or any other suitable graft or graft material) that is physically and fluidically coupled to the pump outlet and also to the right subclavian artery or other suitable point in the circulatory system (e.g., via suturing or the like).

The inlet flow cannula 320 is physically and fluidically coupled between the pump inlet and the left atrium 2. More specifically, as shown in FIG. 4, the inlet flow cannula 320 is physically coupled to the wall 3 of the left atrium 2 that forms or otherwise defines at least a portion of the atrium dome. In this manner, oxygenated blood is drawn though the inlet flow cannula 320, into the pump 301, and through the outlet flow cannula 309, thereby aiding in the circulation of blood through the body. The inlet flow cannula 320 can be similar to and/or can include any features of any of the cannula assemblies shown and described herein. For example, although not shown in FIG. 4, in some embodiments, the inlet flow cannula 320 can include a support member configured to limit movement of the atrial wall (e.g., the wall 3) relative to the cannula assembly 320.

Figure 5:
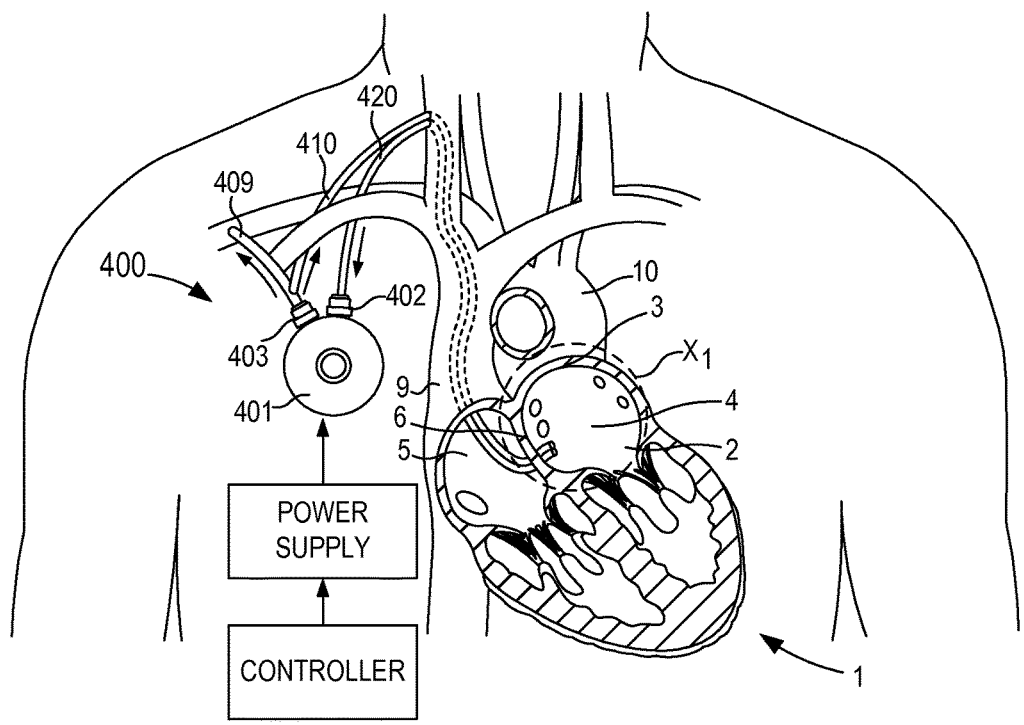
FIG. 5 is an illustration of an assist device in place within a portion of a body of a patient according to an embodiment.
Figure 6:
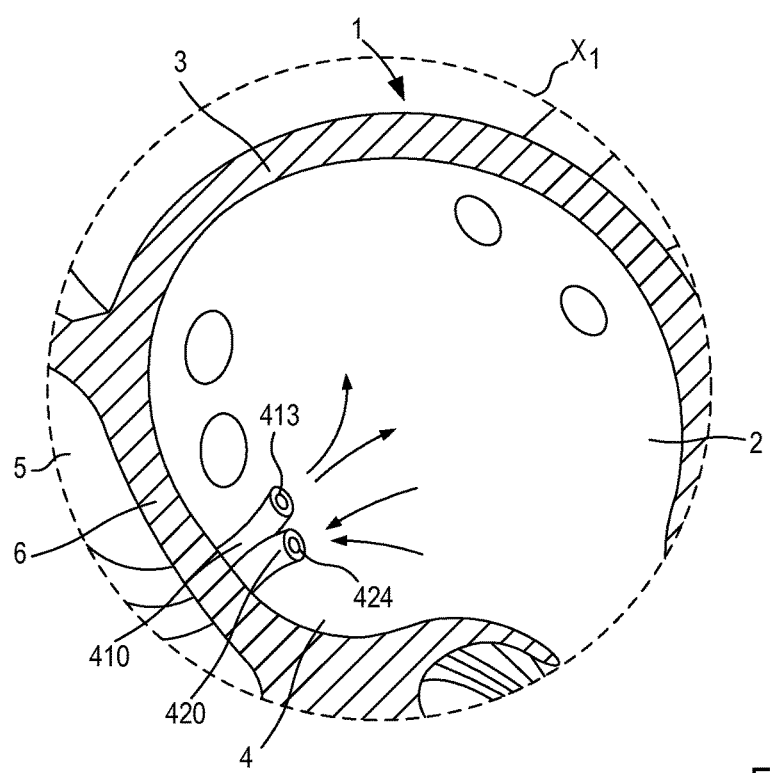
FIG. 6 is an enlarged view of a portion of the assist device and the body identified by the region $X_1$ in FIG. 5.

Although the cannula assemblies 120 and 220 are shown as having a support member (e.g., support member 150 and support member 250, respectively) that contact a wall of the target tissue, in other embodiments, a cannula assembly can include any suitable mechanism for maintaining the stability of the target tissue (e.g., the atrial wall). For example, in some embodiments, a cannula assembly can include a support member that provides a flow of fluid into the interior volume of the organ to exert a force on the wall to maintain the stability thereof. Similarly stated, in some embodiments, a cannula assembly can be configured to provide a flow recirculation into the interior volume of the target organ to maintain the structural stability of the organ. For example, FIGS. 5 and 6 illustrate a VAD 400 that is in fluid communication with the heart 1, according to an embodiment. The VAD 400 includes a pump 401, an outlet flow cannula 409, a recirculation cannula 410, and an inlet flow cannula 420. In some instances, the VAD 400 can be placed in fluid communication with, for example, the left atrium 2 during an at least partially interventional procedure. That is to say, at least a portion of inlet flow cannula 420 and at least a portion of the recirculation cannula 410 can be introduced to the left atrium 2 via, for example, the jugular vein, as shown in FIG. 5.

More specifically, in some instances, the jugular vein can be cannulated in the neck with a needle and a guide wire can be passed through the needle and introduced in the vein. In some instances, an incision can be made in the skin and a series of dilators can be passed over the guide wire to define a path between the skin and the vein. The inlet flow cannula 420 and/or the recirculation cannula 410 can then be passed through the path to be inserted into the jugular vein. In some embodiments, the inlet flow cannula 420 and/or the recirculation cannula 410 can be disposed, for example, within an introducer (e.g., a cannula). Thus, inlet flow cannula 420 and the recirculation cannula 410 can pass through the superior vena cava 9, the right atrium 5, and the septum 6 to be partially disposed in the left atrium 2. In other instances, the inlet flow cannula 420 and the recirculation cannula 410 can be introduced to the left atrium 2 via any other vascular structure such as the subclavian vein and/or any other auxiliary vein in a similar manner as described above. In some embodiments, the VAD 400 can be completely implanted in the body. In other embodiments, at least a portion of the VAD 400 can be disposed outside of the body.

The pump 401 (and any of the pumps described herein) can be any suitable pump that can be configured to pump at relatively high flow rates (e.g., a flow rate of at least 3 L/min, 4 L/min, or 5 L/min), thereby increasing the efficiency of the VAD 400. In some embodiments, the pump 401 can be configured to receive electrical power and/or an electrical charge from a power source (see e.g., FIG. 5). In some embodiments, the pump 401 can receive electrical power and/or an electrical recharge via percutaneous energy transfer. The pump 401 includes an inlet port 402 that is physically and fluidically coupled to the inlet flow cannula 420 and an outlet port 403 that is physically and fluidically coupled to the outlet flow cannula 409 and the recirculation cannula 410. The inlet flow cannula 420 defines a flow path through which blood can flow from the left atrium 2 to the pump 401 (e.g., the pump 401 draws blood from the left atrium 2 by producing a negative pressure differential between the left atrium 2 and the pump 401). The outlet flow cannula 409 can be coupled to the right subclavian artery or other suitable point in the circulatory system (e.g., via suturing or the like) to place the outlet port 403 of the pump 401 in fluid communication with the circulatory system.

The recirculation cannula 410 is physically and fluidically coupled to the outlet flow cannula 409 and/or the pump outlet 403, and is configured to be introduced to the left atrium 2 as described above. More specifically, the recirculation cannula 410 can define a flow path through which blood can flow from the pump 401 back to the left atrium 2. Thus, in use the recirculation cannula can operate in a manner similar to mitral regurgitation. For example, as shown in FIG. 6, the inlet flow cannula 420 can define a lumen 424 that receives a flow of blood from the left atrium 2 to be delivered to the pump 401 and the recirculation cannula 410 can define a lumen 413 that receives a flow of blood from the pump 401 to be delivered to the left atrium 2. The recirculated flow of blood back to the left atrium 2 can, for example, reduce the risk of a suction event as a result of the negative pressure differential between the pump 401 (e.g., via the inlet flow cannula 420) and the left atrium 2. Moreover, as a negative pressure within the left atrium 3 increases as the result of a suction event, the negative pressure can draw an increased volume of blood through the recirculation cannula 410, which can offset and/or reverse the suction event. Thus, the risk of a collapse of the atrial wall and subsequent obstruction of the inlet flow cannula 420 and/or the risk of kinking of the inflow at the pulmonary veins is reduced.

As described above, the recirculation of blood via the recirculation cannula 410 can increase the pressure in the left atrium 2 which can increase, for example, tension in the atrial chamber. Furthermore, the total inflow to the left atrium 2 can be increased (e.g., the sum of flow from the pulmonary veins and the recirculated flow from the pump 401). The increase in the inflow expands the left atrium 2, resists collapse and distortion of the atrium 2, and, as a result, encourages more inflow from the pulmonary veins. Similarly stated, momentum of the inflow to the left atrium 2 can result in higher flow rates through the pulmonary veins and the left atrium 2. Thus, the VAD 400 can produce a higher flow rate of blood from the heart to the pump 401 when recirculating a flow of blood from the pump 401 back to the left atrium 2. Moreover, the impact of cyclic flow reductions to the left atrium 2 that occur in association with changes in position of the patient, changes in respiration, dehydration, and/or other forms of overall heart function depression is reduced as the overall flow rates to the left atrium 2 are increased, further reducing the likelihood of a suction event. Thus, this arrangement and methods of use thereof provide for a fluidic stabilization of the atrium.

In some instances, the use of the recirculation cannula to fluidically support and/or maintain the atrium can produce a favorable fluid flow characteristic within the heart that improves the overall circulation efficiency. For example, in some embodiments, the supply of recirculation flow can enhance the suction into the tubular member 421 such that even though a portion of the pump flow is being recirculated back to the heart (i.e., via the recirculation cannula 410), the overall flow via the outflow cannula 409 is greater than if no recirculation flow had been present. Similarly stated, in some embodiments, the siphoning of a portion of the outflow produces an overall efficiency increase such that the net outflow (via cannula 409) is increased.

In some instances, the flow of blood from the pump 401 to the left atrium 2 via the recirculation cannula 410 can be modified or changed. For example, in some instances, the amount of recirculation flow can be adjusted to reduce waste energy and optimize flow to the patient based on information received from one or more sensors, pump controllers, and/or the like. By way of example, if a suction event occurred due to collapse of the atrium 2 in a region around the lumen 424 of the inflow cannula 420, a change in vibration inside the pump 401 or an associated change in pump motor speed and/or energy consumption can occur. In response to such changes in pump performance, a pump controller (see e.g., FIG. 5) can cause the pump 401 to increase the recirculation flow, thereby increasing the pressure in the left atrium 2 that can facilitate the atrial wall returning to a non-collapsed configuration. Thus, the rate of the recirculation flow associated with the suction event can be determined and, in some instances, the recirculation flow rate can be increased to prevent atrial suction events. In some instances, a pump controller or the like can be configured to adjust the amount and/or the balance of inflow and re-circulated flow in substantially real-time to provide the optimum net increase in flow to the patient, while reducing the risk of suction episodes and optimizing energy consumption.

In some embodiments, the VAD 400 can include one or more sensors (not shown), for example, in the pump 401, the outlet flow cannula 409, the recirculation cannula 410, and/or the inlet flow cannula 420. For example, in some embodiments, the VAD 400 can include one or more pressure sensors and/or flow sensors. In some embodiments, a pressure sensor can be placed inside the left atrium 2 associated with or independent of the inlet flow cannula 420 and/or the recirculation cannula 410. Thus, a low pressure in the left atrium 2 or in the inlet flow cannula 420 (measured near the left atrium) can be sensed and a signal can be sent to, for example, a pump controller to increase the recirculation flow and/or to reduce overall pump flow.

In some embodiments, the size, orientation, and/or relative position of the recirculation cannula 410 and the inlet flow cannula 420 can be configured to produce, for example, a dynamic flow field that is conducive to stabilizing the atrial wall. For example, while shown in FIG. 6 as being disposed adjacent to one another, in other embodiments, a distal end portion of the inlet flow cannula 420 can be in a first position relative to the left atrium 2 and a distal end portion of the recirculation cannula 410 can be in a second position relative to the left atrium 2. Similarly, in some embodiments, the diameter of the inlet flow cannula 420 (and/or the lumen 424) and that of the recirculation cannula 410 (and/or the lumen 413) can be different. For example, in some embodiments, the lumen 413 defined by the recirculation cannula 410 can have a diameter that is smaller than a diameter of the lumen 424 defined by the inlet flow cannula 420. Thus, the size, shape, orientation, configuration, etc. of the inlet flow cannula 420 relative to the recirculation cannula 410 (or vice versa) can be changed and/or configured to increase the inlet flow of blood from the heart 1 to the pump 401 and reduce the likelihood of a suction event or collapsing of the atrium.

Although the inlet flow cannula 420 and the recirculation cannula 410 are shown in FIGS. 5 and 6 as being separate from one another, in other embodiments, any portion of the inlet flow cannula 420 and the recirculation cannula 410 can share a common structure. Similarly stated, in some embodiments a cannula assembly can include a flow member that defines both an inflow lumen (or channel) and a recirculation lumen (or channel). In some embodiments, for example, at least a portion of the recirculation cannula 410 can be disposed in the lumen 424 defined by the inlet flow cannula 420, as described in further detail herein.

Furthermore, although the recirculation cannula 410 is shown in FIG. 5 as being coupled to the outlet flow cannula 409, in other embodiments, the recirculation cannula 410 can be physically and fluidically coupled to any suitable outflow portion of the VAD 400.

Although the inlet flow cannula 420 and the recirculation cannula 410 are shown in FIG. 6 as defining a single lumen 424 and 413, respectively, in other embodiments, the inlet flow cannula 420 and/or the recirculation cannula 410 can each define multiple lumens.

Although the recirculation cannula 410 and the inlet flow cannula 420 are shown as being inserted into the jugular vein and then the superior vena cava 9 (e.g., via an interventional approach), in some instances, the recirculation cannula 410 and the inlet flow cannula 420 can be inserted directly into the superior vena cava 9. For example, FIG. 7 illustrates the VAD 400 with the recirculation cannula 410 and the inlet flow cannula 420 being inserted directly into the superior vena cava 9.

Figure 7:
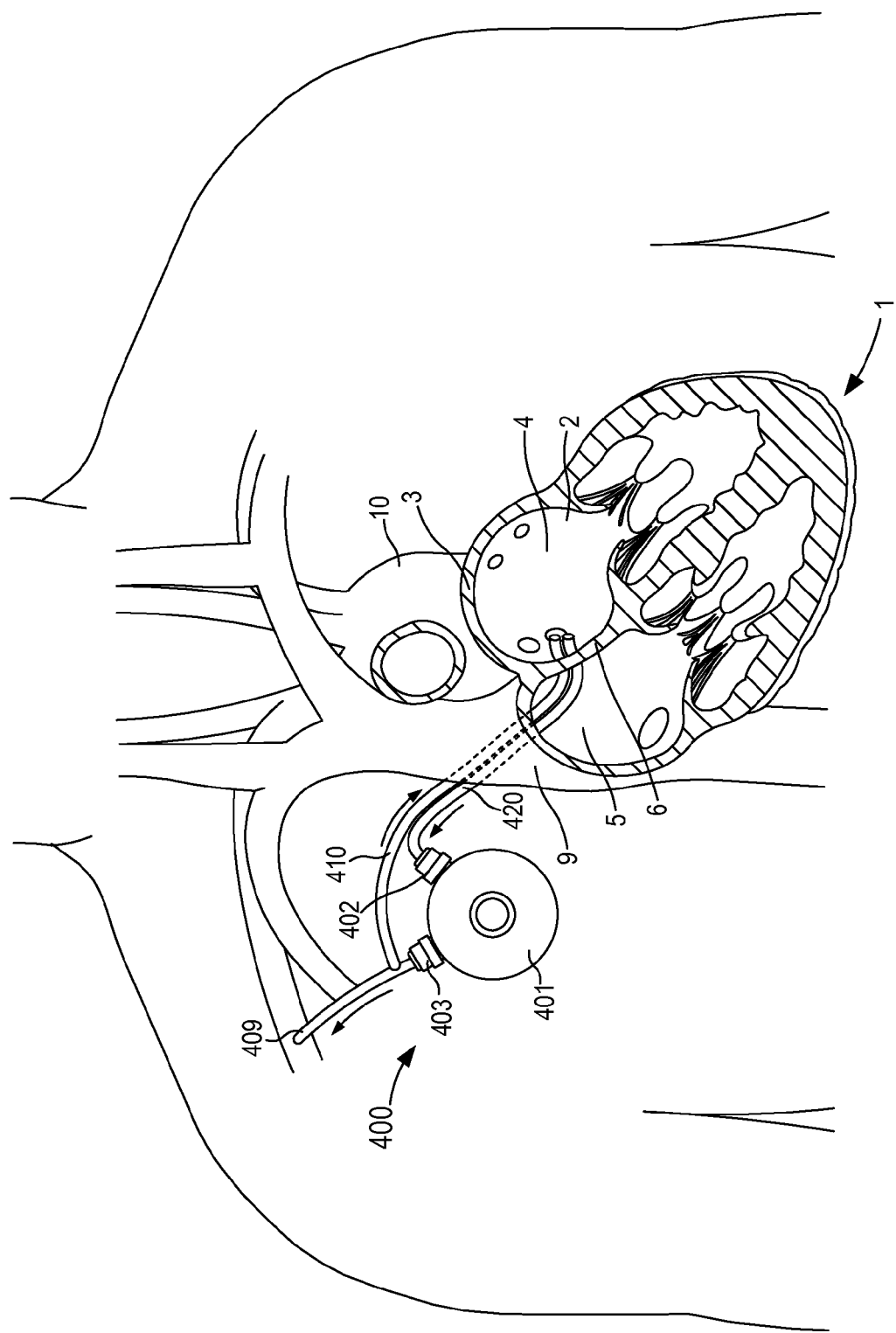
FIGS. 7-9 are illustrations of an assist device in place within a portion of a body of a patient, each according to an embodiment.
Figure 8:
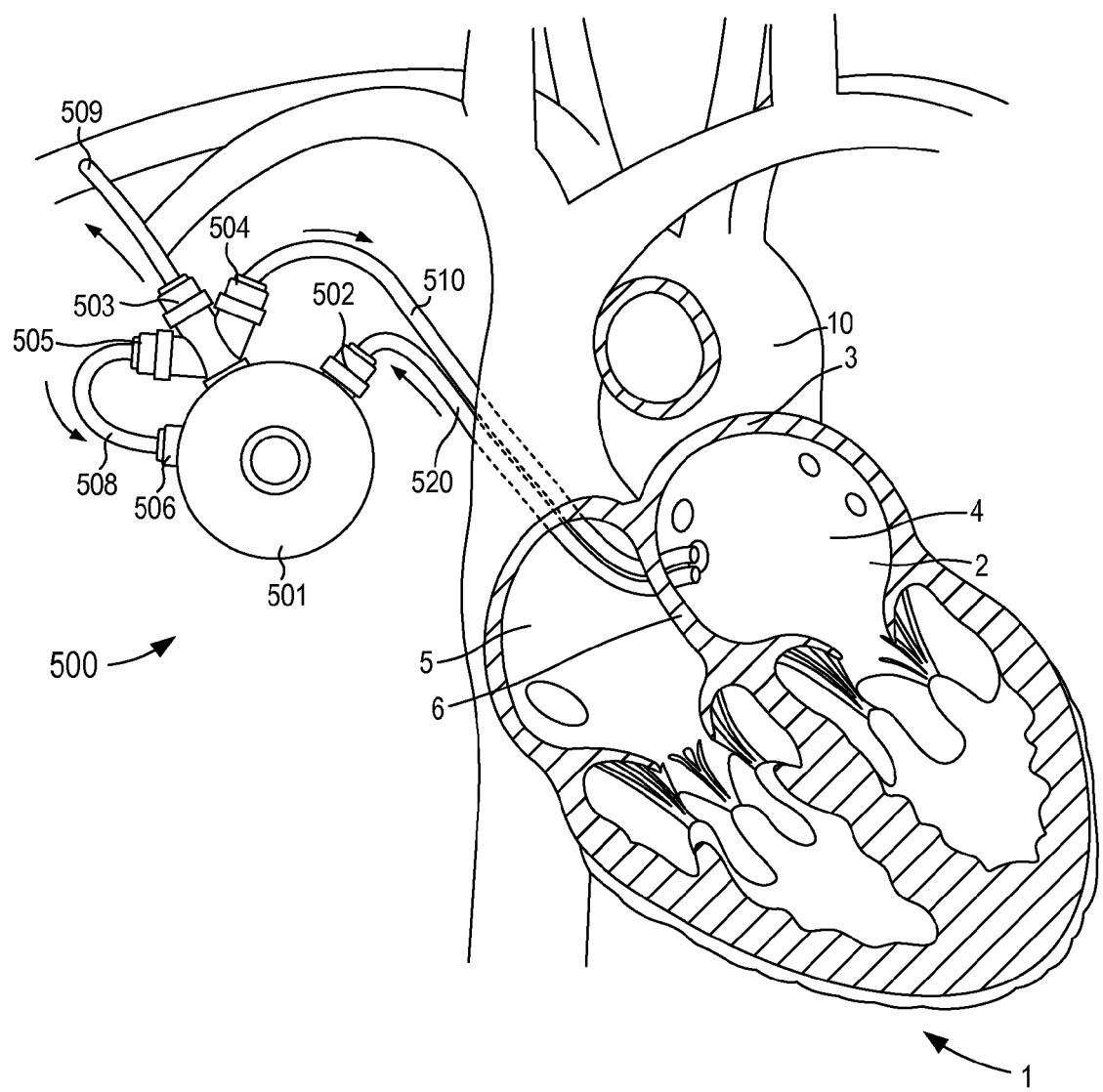

Although the VAD 400 is shown in FIGS. 5-7 as including a recirculation system in a particular configuration, in some embodiments, a VAD can include a recirculation system in any suitable configuration. For example, FIG. 8 is an illustration of a VAD 500 in fluid communication with the heart 1. The VAD 500 includes a pump 501, an outlet flow cannula 509, a first recirculation cannula 508, a second recirculation cannula 510, and an inlet flow cannula 520. The VAD 500 can be configured to function substantially similar to the VAD 400 described above with reference to FIGS. 5-7. Moreover, the outlet flow cannula 509, the second recirculation cannula 510, and the inlet flow cannula 520 can be similar in form and function as the outlet flow cannula 409, the recirculation cannula 410, and the inlet flow cannula 420, respectively, described above with reference to the VAD 400. Thus, the outlet flow cannula 509, the second recirculation cannula 510, and the inlet flow cannula 520 are not described in further detail herein.

The pump 501 can be any suitable pump that can be configured to pump at relatively high flow rates, such as those described above with reference to the pump 301 of the VAD 300 and/or the pump 401 of the VAD 400. The pump 501 includes an inlet port 502, a first outlet port 503, a second outlet port 504, a third outlet port 505, and a pump recirculation port 506. The inlet port 502 is physically and fluidically coupled to the inlet flow cannula 520. In this manner, the inlet flow cannula 520 can receive an inlet flow of blood from the left atrium 2 and deliver the flow of blood to the pump 501, as described above with reference to the inlet flow cannula 420 of FIGS. 5-7. The first outlet port 503 is physically and fluidically coupled to the outlet flow cannula 509 such that a flow of blood can be delivered, via the outlet flow cannula 509, from the pump 501 to the circulatory system, as described above. The second outlet port 504 is physically and fluidically coupled to the second recirculation cannula 510. In this manner, the second recirculation cannula 510 can receive an outlet flow of blood from the pump and deliver the flow of blood to the left atrium 2, as described above with reference to the recirculation cannula 410 of FIGS. 5-7. The third outlet port 505 is physically and fluidically coupled to the first recirculation cannula 508. The first recirculation cannula 508 is also physically and fluidically coupled to the pump recirculation port 506. Thus, the first recirculation cannula 508 can receive an outlet flow of blood from the pump 501 and deliver the outlet flow of blood to the pump recirculation port 506. In such embodiments, the recirculation of the outlet flow to the pump 501 can clean an interior region of the pump 501, thereby reducing the likelihood of clot development in the interior region of the pump 501. In this manner, the VAD 500 can assist the flow of blood from the heart 1 to the circulation system of the patient in a manner similar to that described above with reference to the VAD 400 of FIGS. 5-7.

Figure 9:
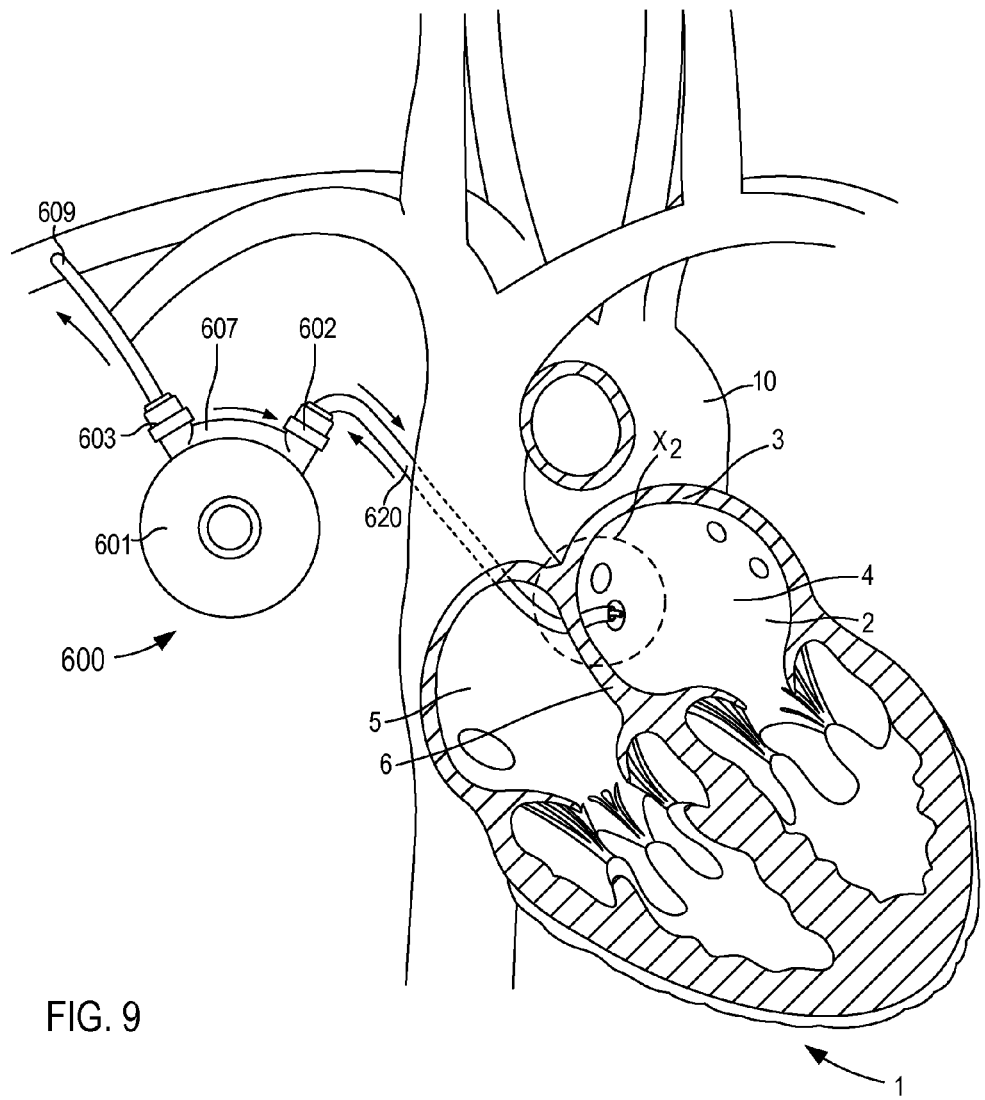
Figure 10:
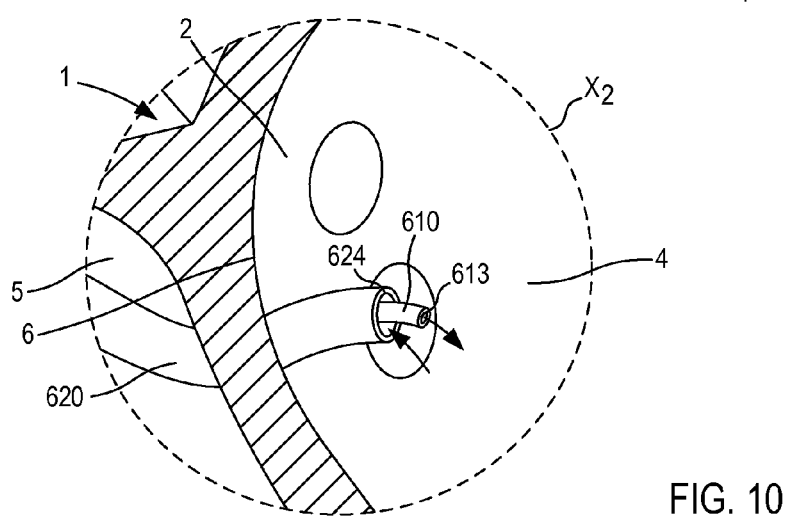
FIG. 10 is an enlarged view of a portion of the assist device and the body identified by the region $X_2$ in FIG. 9.

Although the pump 501 is shown in FIG. 8 as including an outlet port that is coupled to the recirculation cannula, in other embodiments, a VAD can include a pump with an integrated recirculation system. For example, FIGS. 9 and 10 are illustrations of a VAD 600 in fluid communication with the heart 1. The VAD 600 includes a pump 601, an outlet flow cannula 609, a recirculation cannula 610, and an inlet flow cannula 620. The VAD 600 can be configured to function substantially similar to the VAD 400 described above with reference to FIGS. 5-7. The arrangement of the recirculation cannula 610 and the inlet flow cannula 620 can differ from the arrangement of the recirculation cannula 410 and the inlet flow cannula 420, however, in that at least a portion of the recirculation cannula 610 is disposed within a lumen 624 defined by the inlet flow cannula 620. Thus, a diameter of the lumen 624 defined by the inlet flow cannula 620 can be sufficiently large to receive the recirculation cannula 610 and an inlet flow of blood from the left atrium 2. As described above with reference to the VAD 400 and elsewhere herein, the inlet flow cannula 620 and the recirculation cannula 610 can be arranged in any suitable orientation. For example, as shown in FIG. 10, a distal end portion of the recirculation cannula 610 can extend beyond a distal end portion of the inlet flow cannula 620 such that a flow of recirculated blood can flow from the pump 601 to the left atrium 2 via a lumen 613 defined by the recirculation cannula 610. In this manner, the outlet flow cannula 609, the recirculation cannula 610, and the inlet flow cannula 620 can function similarly to the outlet flow cannula 409, the recirculation cannula 410, and the inlet flow cannula 420, respectively, described above with reference to the VAD 400 and are therefore not described in further detail herein.

The pump 601 can be any suitable pump that can be configured to pump at relatively high flow rates, such as those described above with reference to the pump 301 of the VAD 300 and/or 401 of the VAD 400. The pump 601 includes an inlet port 602, an outlet port 603, and a recirculation channel 607. The inlet port 602 is physically and fluidically coupled to the inlet flow cannula 620. Although not shown in FIG. 9, in some embodiments, the inlet port 602 can be, for example, a dual port configuration that is physically and fluidically coupled to the inlet flow cannula 620 and the recirculation cannula 610, as described in further detail herein. The outlet port 603 is physically and fluidically coupled to the outlet flow cannula 609 such that a flow of blood can be delivered, via the outlet flow cannula 609, from the pump 601 to the circulatory system, as described above. The recirculation channel 607 can be integrated into the pump 601 and can define a flow path between an outlet flow of the pump and a portion of the inlet port 602 physically and fluidically coupled to the recirculation cannula 610. Thus, the recirculation cannula 610 can receive an outlet flow of blood from the pump 601 and deliver the flow of blood to the left atrium 2, as described above with reference to the recirculation cannula 410 of FIGS. 5-7. Furthermore, the arrangement of the recirculation cannula 610 and the inlet flow cannula 620 can be such that the inlet flow of blood from the left atrium 2 is distinct from the recirculation flow of blood to the left atrium 2. In other embodiments, a portion of the recirculation cannula 610 and a portion of the inlet flow cannula 620 can have a common structure such that at least of portion of the inlet flow of blood from the left atrium 2 is in fluid communication with the recirculation flow of blood to the left atrium 2. In some instances, placing the inlet flow in fluid communication with the recirculation flow can, for example, regulate the flow rate of the inlet flow and/or the recirculation flow and/or can balance a pressure differential between the left atrium 2 and the pump 601. In this manner, the VAD 600 can assist the flow of blood from the heart 1 to the circulation system of the patient in a manner similar to that described above with reference to the VAD 400 of FIGS. 5-7. Moreover, in some instances, the integration of the recirculation channel 607 can facilitate placement of the pump 601 in the body.

Figure 11:
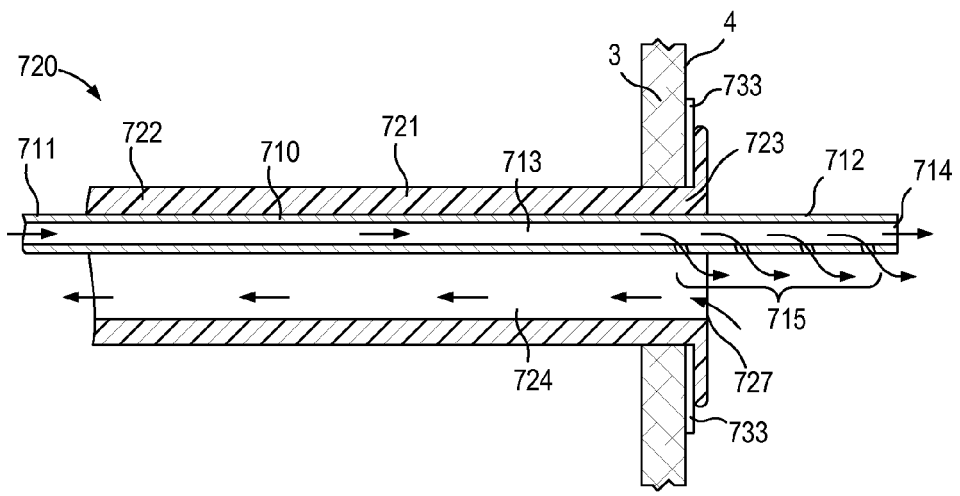
FIGS. 11-15 are cross-sectional illustrations of a portion of an inlet flow cannula assembly, each according to an embodiment.

In some embodiments, a cannula assembly configured to fluidically stabilize an organ (e.g., the heart) can have any suitable configuration. For example, a cannula assembly can define a recirculation channel having one or more outlets configured to produce a dynamic flow field and/or pressure distribution to maintain the structural stability of the organ. Said another way, the recirculation channel and outlets can be configured to produce a recirculation flow that minimizes deformation, movement and/or collapsing of a portion of the organ. For example, FIG. 11 is a cross-sectional illustration of a portion of an inlet flow cannula assembly 720 according to an embodiment. The inlet flow cannula assembly 720 (also referred to herein as "cannula assembly") can be used, for example, in any of the assist devices described herein. As such, the cannula assembly 720 can be inserted into the body and coupled to a wall 3 of the left atrium of the heart (not shown in FIG. 11), as described in further detail herein. The cannula assembly 720 includes a tubular member 721 and a recirculation member 710. The tubular member 721 can be any suitable shape, size, or configuration. For example, in some embodiments, the tubular member 721 can be substantially cylindrical and can be formed from any suitable biocompatible material such as, for example, nickel-titanium alloy (Nitinol®), stainless steel, silicone, polyester, PTFE, polypropylene, and/or the like. arranged, for example, as cannula or catheter. The tubular member 721 has a proximal end portion 722 and a distal end portion 723, and defines a lumen 724 therethrough that can be placed in fluid communication with an interior region of the left atrium when the tubular member 721 is coupled to the wall 3. The proximal end portion 722 can be coupled to, for example, an inlet flow port of a pump included in an assist device such as those described above.

The tubular member 721 can be transitioned from a first configuration (e.g., a collapsed configuration, not shown in FIG. 11) to a second configuration (e.g., an expanded configuration, shown in FIG. 11) to couple the cannula assembly 720 to the wall 3. For example, the distal end portion 723 of the tubular member 721 can form a substantially flared end when in the second configuration. In some embodiments, the flared distal end portion 723 can be coupled to the wall 3 via sutures or the like. In other embodiments, the flared distal end portion 723 can include one or more retention members that can engage the wall 3 (e.g., and exert a force thereon) to couple the tubular member 721 to the wall 3. In some embodiments, the retention members can be configured to maintain a surface of the tubular member 721 in continuous contact with an inner surface 4 of the wall 3, as described in further detail herein.

As shown in FIG. 11, the distal end portion 723 of the tubular member 721 includes and/or is otherwise coupled to a fabric 733 or the like that can be maintained in contact with the inner surface 4 of the wall to encourage tissue ingrowth. In this manner, wall 3 of the left atrium can heal and/or grow about the retention members of tubular member 721 to avoid clot formation. As shown, the fabric 733 can extend beyond an outer edge (e.g., a margin) of the distal end portion 723 of the tubular member 721. In some embodiments, the fabric 733 and the outer edge of the distal end portion can form and/or define a step and/or discontinuity that can define a boundary for the ingrowth of the tissue. As described above, the fabric 733 can be formed from any suitable material such as, for example, a polyester or PTFE. In some embodiments, the fabric 733 can be formed from and/or coated with biologic materials such as animal or human pericardium or treated animal or human intestinal tissues. In some embodiments, the fabric 733 can have a textured or roughened surface that can facilitate the ingrowth of the tissue.

As shown, the recirculation member 710 is at least partially disposed within the lumen 724 defined by the tubular member 721. The recirculation member 710 includes a proximal end portion 711 and a distal end portion 712, and defines a lumen 713 therethrough. In some embodiments, the recirculation member 710 can be coupled to the tubular member 721. In other embodiments, the recirculation member 710 can be monolithically formed with the tubular member 721. Similarly stated, in some embodiments, the tubular member 721 can define two distinct lumens or channels (e.g., the lumen 713 and the lumen 724). In some embodiments, the recirculation member 710 can be disposed in the lumen 724 defined by the tubular member 721 such that an outer surface of the recirculation member 710 is in contact with an inner surface of the tubular member 720

(i.e., adjacent to a wall defining the lumen 724). In other embodiments, the recirculation member 710 can be, for example, suspended substantially in the center of the lumen 724 (e.g., via a support structure or the like not shown in FIG. 11). Moreover, the recirculation member 710 can have any suitable thickness.

The proximal end portion 711 of the recirculation member 710 can be coupled to, for example, a recirculation port of a pump of an assist device such as those described above. The distal end portion 712 of the recirculation member 710 can be configured to extend through an opening 727 defined by the distal end portion 723 of the tubular member 721. For example, as shown in FIG. 11, the distal end portion 712 of the recirculation member 710 extends beyond the distal end portion 723 of the tubular member 721, when the tubular member 721 is coupled to the wall 3. Similarly stated, the distal end portion 712 of the recirculation member 710 can extend beyond the inner surface 4 of the wall 3 when the tubular member 721 is coupled thereto. The distal end portion 712 of the recirculation member 710 defines an opening 714 at the distal end and a set of openings 715 arranged along the circumference of the recirculation member 710.

As described above with reference to the VAD 400 in FIGS. 5 and 6, the lumen 724 of the tubular member 721 is in fluid communication with, for example, the left atrium and defines a flow path through which blood can flow from the left atrium to, for example, a pump of an assist device. Similarly, the lumen 713 of the recirculation member 710 is in fluid communication with, for example, the left atrium and defines a flow path through with blood can flow from the pump to the left atrium (i.e., a recirculation flow). In this manner, the recirculation flow can, for example, reduce a negative pressure differential between the pump and the left atrium as well as increase a total volume of inflow into the left atrium that can limit a collapsing of the wall 3 which could lead to an obstruction of the lumen 724 and/or of any vascular structure in fluid communication with the left atrium, as described in detail above with reference to the VAD 400 of FIGS. 5-7.

In some embodiments, the arrangement of the distal opening 714 and the circumferential openings 715 can be modified, for example, to achieve a desired flow characteristic into and out of the left atrium, as described in detail above. For example, in some embodiments, the circumferential openings 715 can be arranged to produce a dynamic flow field that is conducive to stabilizing the atrial wall. More particularly, the location of the openings 715 on the recirculation member 710 can be such that a sufficient and/or spatially uniform pressure can be produced within the atrium. In other embodiments, one or more of the circumferential openings 715 can be positioned to directed a portion of the recirculation flow towards a portion of the cannula assembly 720 (e.g., the outer wall of the recirculation member 710, the distal end portion 723 of the tubular member 721) to reduce the likelihood of clot formation on such portions (e.g., by "washing" of the portion or preventing stagnation near such portion). Although the circumferential openings 715 are shown as being substantially normal to the lumen 713 of the recirculation member 710, in other embodiments, one or more of the circumferential openings can be angled. Similarly stated, in some embodiments a center line of at least one of the circumferential openings 715 can be at an acute angle to a center line of the lumen 713.

Figure 12:
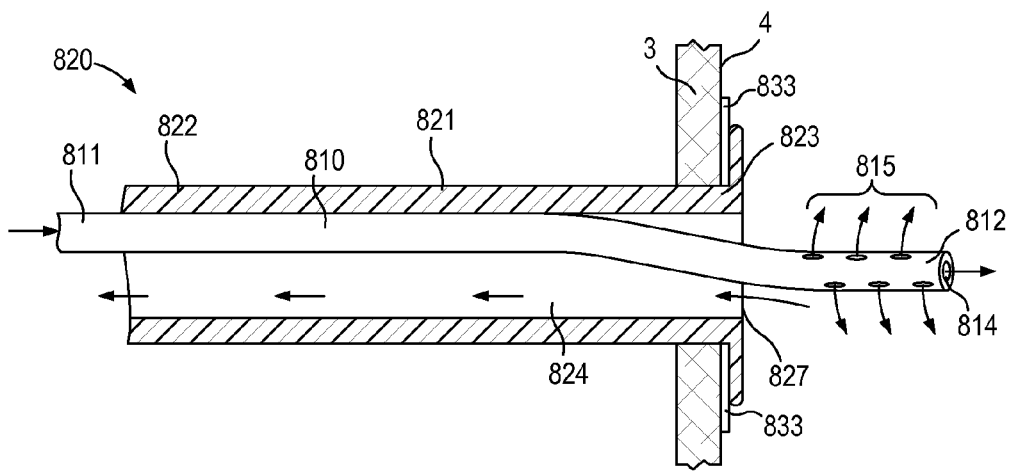

Although the recirculation member 710 is shown in FIG. 11 as being substantially linear and substantially parallel to the tubular member 720, in other embodiments, a cannula assembly can include a recirculation member that is substantially nonlinear and/or that is not parallel to a tubular member. For example, FIG. 12 is a cross-sectional illustration of an inlet flow cannula assembly 820 according to an embodiment. The inlet flow cannula assembly 820 (also referred to herein as "cannula assembly") can be used, for example, in any of the assist devices described above. As such, the cannula assembly 820 can be inserted into the body and coupled to a wall 3 of the left atrium of the heart (not shown in FIG. 12), as described above with reference to the cannula assembly 720.

The inlet flow cannula assembly 820 (also referred to herein as "cannula assembly") includes a tubular member 821 and a recirculation member 810. The tubular member 821 can be substantially similar in form and function as the tubular member 721 included in the cannula assembly 720 of FIG. 11. For example, the tubular member 821 has a proximal end portion 822 and a distal end portion 823, and defines a lumen 824 therethrough. The proximal end portion 822 of the tubular member 821 is configured to be physically and fluidically coupled to an inlet port of a pump included in an assist device such as, for example, those described herein. The tubular member 822 can be transitioned between a first configuration and a second configuration to place a surface of the distal end portion 823 in contact with an inner surface 4 of the wall 3 to couple the cannula assembly 820 to and/or within the atrium. More particularly, the distal end portion 823 includes and/or is otherwise coupled to a fabric 833 that is placed in contact with the inner surface 4 of the wall 3 when the tubular member 821 is in the second configuration. In some embodiments, the fabric 833 can be configured to facilitate tissue ingrowth such that the wall 3 of the left atrium can heal about at least a portion of the tubular member 821, as described above.

As shown in FIG. 12, the recirculation member 810 is at least partially disposed within the lumen 824 defined by the tubular member 821. The recirculation member 810 includes a proximal end portion 811 and a distal end portion 812, and defines a lumen 813 therethrough. The recirculation member 810 can be substantially similar to the recirculation member 710 described above. For example, the proximal end portion 811 of the recirculation member 810 can be physically and fluidically coupled to a recirculation port included in the pump. The distal end portion 812 can be configured to extend through an opening 827 defined by the tubular member 821. For example, as shown in FIG. 12, the distal end portion 812 of the recirculation member 810 extends beyond the distal end portion 823 of the tubular member 821, when the tubular member 821 is coupled to the wall 3. Moreover, the distal end portion 812 of the recirculation member 810 defines an opening 814 at the distal end and a set of openings 815 arranged along the circumference of the recirculation member 810, as described above with reference to the recirculation member 710.

The recirculation member 810 differs from the recirculation member 710, however, in that the recirculation member 810 includes a portion that is substantially non-coaxial with the proximal end portion 811 and/or the distal end portion 812. Said another way, the arrangement of the recirculation member 810 can be such that at least a part of the proximal end portion 811 is adjacent to an inner surface of the tubular member 810 and at least a part of the distal end portion 812 diverges away from the inner surface (i.e., in not adjacent to the inner surface), as shown in FIG. 12. For example, in some embodiments, the distal end portion 812 of the recirculation member 810 can diverge away from the inner surface such that a longitudinal centerline defined by the distal end portion 812 of the recirculation member 810 is substantially coaxial with a longitudinal centerline defined by the tubular member 821. In some instances, the arrangement of the distal end portion 812 of the recirculation member 810 relative to the distal end portion 823 of the tubular member 821 can, for example, improve a set of fluid flow characteristics within the left atrium and/or the tubular member 821. For example, in some instances, the arrangement of the distal end portion 812 of the recirculation member 810 can produce a fluid flow pattern that can reduce and/or prevent a suction event, as described above.

Figure 13:
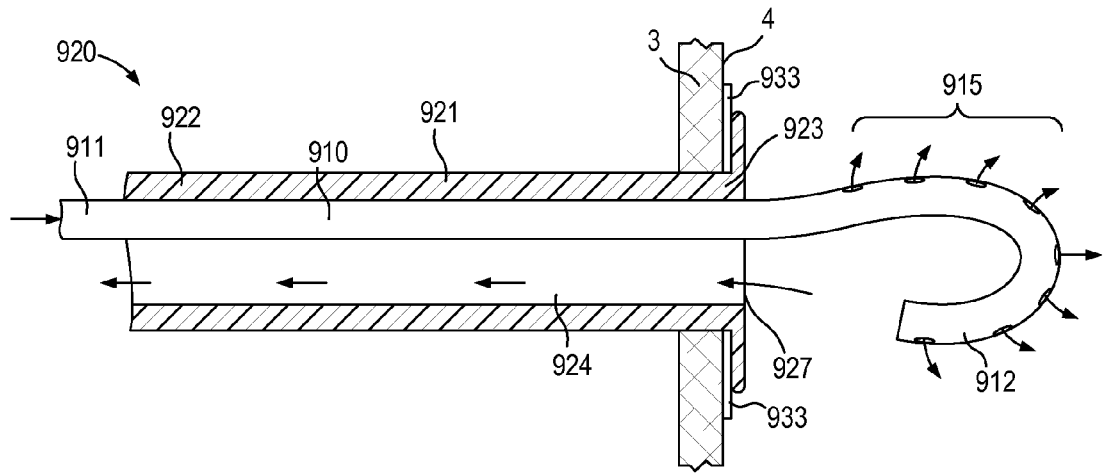

Although the set of openings 715 and 815 of the recirculation members 710 and 810, respectively, are shown and described as being disposed in a radial arrangement about a longitudinal centerline of the distal end portions 712 and 812, respectively, in other embodiments, a recirculation member can be arranged such that a set of openings defined by a distal end portion are not arranged about a common axis. For example, FIG. 13 is a cross-sectional illustration of an inlet flow cannula assembly 920 according to an embodiment. The inlet flow cannula assembly 920 (also referred to herein as "cannula assembly") can be used, for example, in any of the assist devices described above. As such, the cannula assembly 920 can be inserted into the body and coupled to a wall 3 of the left atrium of the heart (not shown in FIG. 13), as described above with reference to the cannula assembly 720.

The inlet flow cannula assembly 920 (also referred to herein as "cannula assembly") includes a tubular member 921 and a recirculation member 910. The tubular member 921 has a proximal end portion 922 and a distal end portion 923, and defines a lumen 924 therethrough. The proximal end portion 922 of the tubular member 921 can be physically and fluidically coupled to an inlet port of a pump included in an assist device, as described above. The distal end portion 923 includes and/or is otherwise coupled to a fabric 933 that is placed in contact with an inner surface 4 of a wall 3 of an organ such as, for example, the left atrium of the heart. The fabric 933 can be configured to facilitate tissue ingrowth such that the wall 3 of the left atrium can heal about at least a portion of the tubular member 921, as described above. In some embodiments, the tubular member 921 can be substantially similar in form and function as the tubular member 721 included in the cannula assembly 720 of FIG. 11. Therefore, the tubular member 921 is not described in further detail herein.

As shown in FIG. 13, the recirculation member 910 is at least partially disposed within the lumen 924 defined by the tubular member 921. The recirculation member 910 includes a proximal end portion 911 and a distal end portion 912, and defines a lumen 913 therethrough. The recirculation member 910 can be substantially similar, at least in part, to the recirculation member 710 described above. For example, the proximal end portion 911 of the recirculation member 910 can be physically and fluidically coupled to a recirculation port included in the pump. The distal end portion 912 can be configured to extend through an opening 927 defined by the tubular member 921 such that the distal end portion 912 of the recirculation member 910 is disposed beyond the distal end portion 923 of the tubular member 921, when the tubular member 921 is coupled to the wall 3. Moreover, the distal end portion 912 of the recirculation member 910 defines a set of openings 915 arranged along the circumference of the recirculation member 910, as described above with reference to the recirculation member 710.

The recirculation member 910 can differ from the recirculation members 710 and 810, however, in that the distal end portion 912 of the recirculation member 910 is substantially nonlinear. Said another way, the arrangement of the recirculation member 910 can be such that at least a part of the distal end portion 912 is curvilinear forming, for example, a hook shape and/or the like. As shown in FIG. 13, the set of openings 915 can be arranged substantially along an outer surface of the distal end portion 912. In this manner, the set of openings 915 can direct a flow of recirculated fluid from the pump (not shown in FIG. 13) to, for example, the left atrium in a substantially fanned orientation. Said another way, the arrangement of the set of openings 915 along the outer surface of the distal end portion 912 can be such that a flow of recirculated fluid exits each opening in a substantially different direction to be dispersed in a substantially curvilinear pattern. In some instances, the arrangement of the set of openings 915 defined by the distal end portion 912 of the recirculation member 910 can improve the fluid flow characteristics within the left atrium and/or the tubular member 921. For example, in some instances, the arrangement of the distal end portion 912 of the recirculation member 910 can produce a fluid flow pattern that can reduce and/or prevent a suction event, collapsing and/or deformation of the atrial, as described above. Although not shown in FIG. 13, in some embodiments, the recirculation member 910 can define an opening at a distal end surface as described above with reference to the recirculation members 710 and 810.

Figure 14:
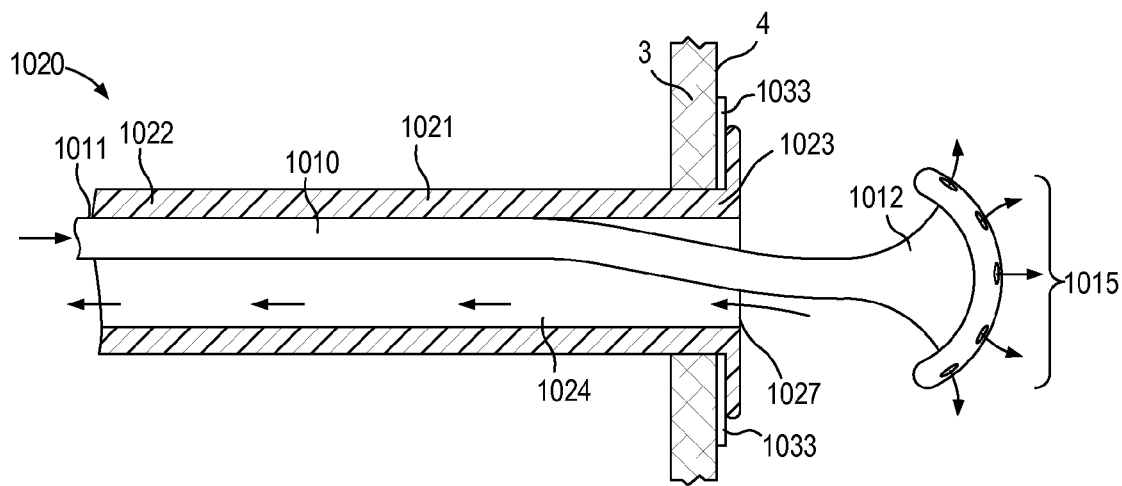

In some embodiments, any of the aspects described above with reference to the recirculation members 710, 810 and/or 910 can be combined. For example, FIG. 14 is a cross-sectional illustration of an inlet flow cannula assembly 1020 according to an embodiment. The inlet flow cannula assembly 1020 (also referred to herein as "cannula assembly") can be used, for example, in any of the assist devices described above. As such, the cannula assembly 1020 can be inserted into the body and coupled to a wall 3 of the left atrium of the heart (not shown in FIG. 14), as described above with reference to the cannula assembly 720.

The inlet flow cannula assembly 1020 (also referred to herein as "cannula assembly") includes a tubular member 1021 and a recirculation member 1010. The tubular member 1021 has a proximal end portion 1022 and a distal end portion 1023, and defines a lumen 1024 therethrough. The distal end portion 1023 includes and/or is otherwise coupled to a fabric 1033 that is placed in contact with an inner surface 4 of a wall 3 of an organ such as, for example, the left atrium of the heart, as described above. In some embodiments, the tubular member 1021 can be substantially similar in form and function as the tubular member 721 included in the cannula assembly 720 of FIG. 11. Therefore, the tubular member 1021 is not described in further detail herein.

As shown in FIG. 14, the recirculation member 1010 is at least partially disposed within the lumen 1024 defined by the tubular member 1021. The recirculation member 1010 includes a proximal end portion 1011 and a distal end portion 1012, and defines a lumen 1013 therethrough. The recirculation member 1010 can be substantially similar, at least in part, to the recirculation members 710, 810, and/or 910 described above. For example, the proximal end portion 1011 of the recirculation member 1010 can be physically and fluidically coupled to a recirculation port included in the pump (not shown in FIG. 14). The distal end portion 1012 can be configured to extend through an opening 1027 defined by the tubular member 1021 such that the distal end portion 1012 of the recirculation member 1010 is disposed beyond the distal end portion 1023 of the tubular member 1021, when the tubular member 1021 is coupled to the wall 3. Moreover, the distal end portion 1012 of the recirculation member 1010 defines a set of openings 1015 arranged along the circumference of the recirculation member 1010, as described above with reference to the recirculation member 710.

As described above with reference to the recirculation member 810, the recirculation member 1010 includes a portion that is substantially non-coaxial with the proximal end portion 1011 and/or the distal end portion 1012. Said another way, the arrangement of the recirculation member 1010 can be such that at least a part of the proximal end portion 1011 is adjacent to an inner surface of the tubular member 1010 and at least a part of the distal end portion 1012 diverges away from the inner surface (i.e., in not adjacent to the inner surface), as shown in FIG. 14. Moreover, as described above with reference to the recirculation member 910, the distal end portion 1012 of the recirculation member 1010 is substantially nonlinear. Said another way, the arrangement of the recirculation member 1010 can be such that at least a part of the distal end portion 1012 is curvilinear forming, for example, a fanned-shape and/or the like. As shown in FIG. 14, the set of openings 1015 can be arranged substantially along an outer surface of the distal end portion 1012. In this manner, the set of openings 1015 can direct a flow of recirculated fluid from the pump (not shown in FIG. 13) to, for example, the left atrium in a substantially fanned orientation, as described above. In some instances, the arrangement of the recirculation member 1010 can improve the fluid flow characteristics within the left atrium and/or the tubular member 1021. For example, in some instances, the arrangement of the distal end portion 1012 of the recirculation member 1010 can produce a fluid flow pattern that can reduce and/or prevent a suction event, collapsing and/or deformation of the atrial, as described above as described herein.

Figure 15:
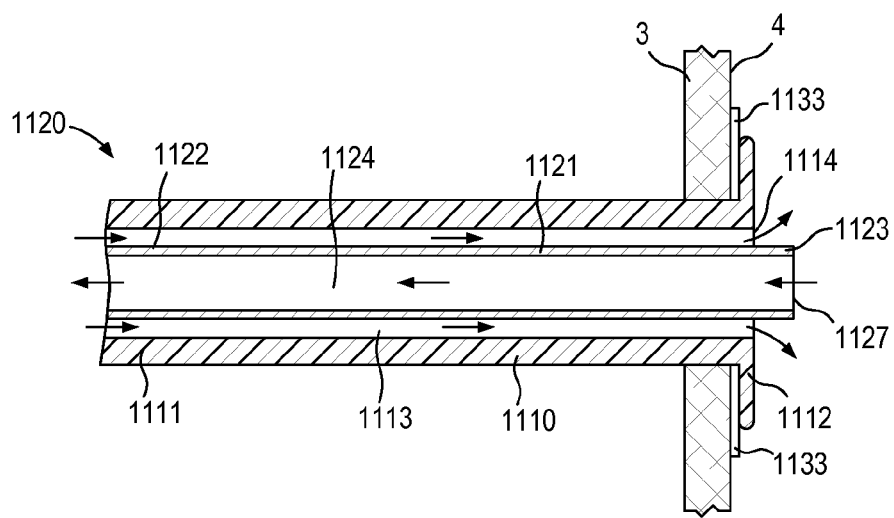

Although the recirculation members 710, 810, 910, and 1010 are shown and described as being disposed within the tubular member 721, 821, 921, and 1021, in other embodiments, a cannula assembly can be arranged such that at least a portion of a tubular member is disposed within a recirculation member. For example, FIG. 15 is a cross-sectional illustration of an inlet flow cannula assembly 1120 according to an embodiment. The inlet flow cannula assembly 1120 (also referred to herein as "cannula assembly") can be used, for example, in any of the assist devices described above. As such, the cannula assembly 1120 can be inserted into the body and coupled to a wall 3 of the left atrium of the heart (not shown in FIG. 15), as described above with reference to the cannula assembly 720.

The inlet flow cannula assembly 1120 (also referred to herein as "cannula assembly") includes a tubular member 1121 and a recirculation member 1110. The recirculation member 1110 has a proximal end portion 1111 and a distal end portion 1112, and defines a lumen 1113 therethrough. The distal end portion 1112 includes and/or is otherwise coupled to a fabric 1133 that is placed in contact with an inner surface 4 of a wall 3 of an organ such as, for example, the left atrium of the heart, as described above. In some embodiments, the recirculation member 1110 can be substantially similar in form as the tubular member 721 included in the cannula assembly 720 of FIG. 11, yet can function to define a fluid flow path (e.g., within the lumen 1113) within which a fluid (e.g., blood) can flow from a pump of an assist device to, for example, the left atrium.

Therefore, aspects of the recirculation member 1110 are not described in further detail herein.

As shown in FIG. 15, the tubular member 1121 is at least partially disposed within the lumen 1113 defined by the recirculation member 1110. The tubular member 1121 includes a proximal end portion 1122 and a distal end portion 1123, and defines a lumen 1124 therethrough. The tubular member 1121 can be substantially similar in function as the tubular member 721 described above. For example, the proximal end portion 1122 of the tubular member 1121 can be physically and fluidically coupled to an inlet port included in the pump. The distal end portion 1123 can be configured to extend through an opening 1114 defined by the recirculation member 1110 to dispose the distal end portion 1123 of the tubular member 1121 beyond the distal end portion 1112 of the recirculation member 1110, when the recirculation member 1110 is coupled to the wall 3. Moreover, the distal end portion 1123 of the tubular member 1121 defines an opening 1127 that can receive an inflow of fluid, as described above. In some instances, the arrangement of the recirculation member 1110 and the tubular member 1121 can improve the fluid flow characteristics within the left atrium, the recirculation member 1110, and/or the tubular member 1121. For example, in some instances, by disposing the tubular member 1121 (e.g., an inlet flow member) within the recirculation member 1110 (e.g., an outlet flow member) the cannula assembly 1120 can produce a fluid flow pattern that can reduce and/or prevent a suction event, collapsing and/or deformation of the atrial, as described above as described above. Similarly, in some instances, the arrangement of the tubular member 1121 and the recirculation member 1110 can increase a total flow rate or volume into, for example, the left atrium and/or into the pump of an assist device, as described above.

Figure 16:
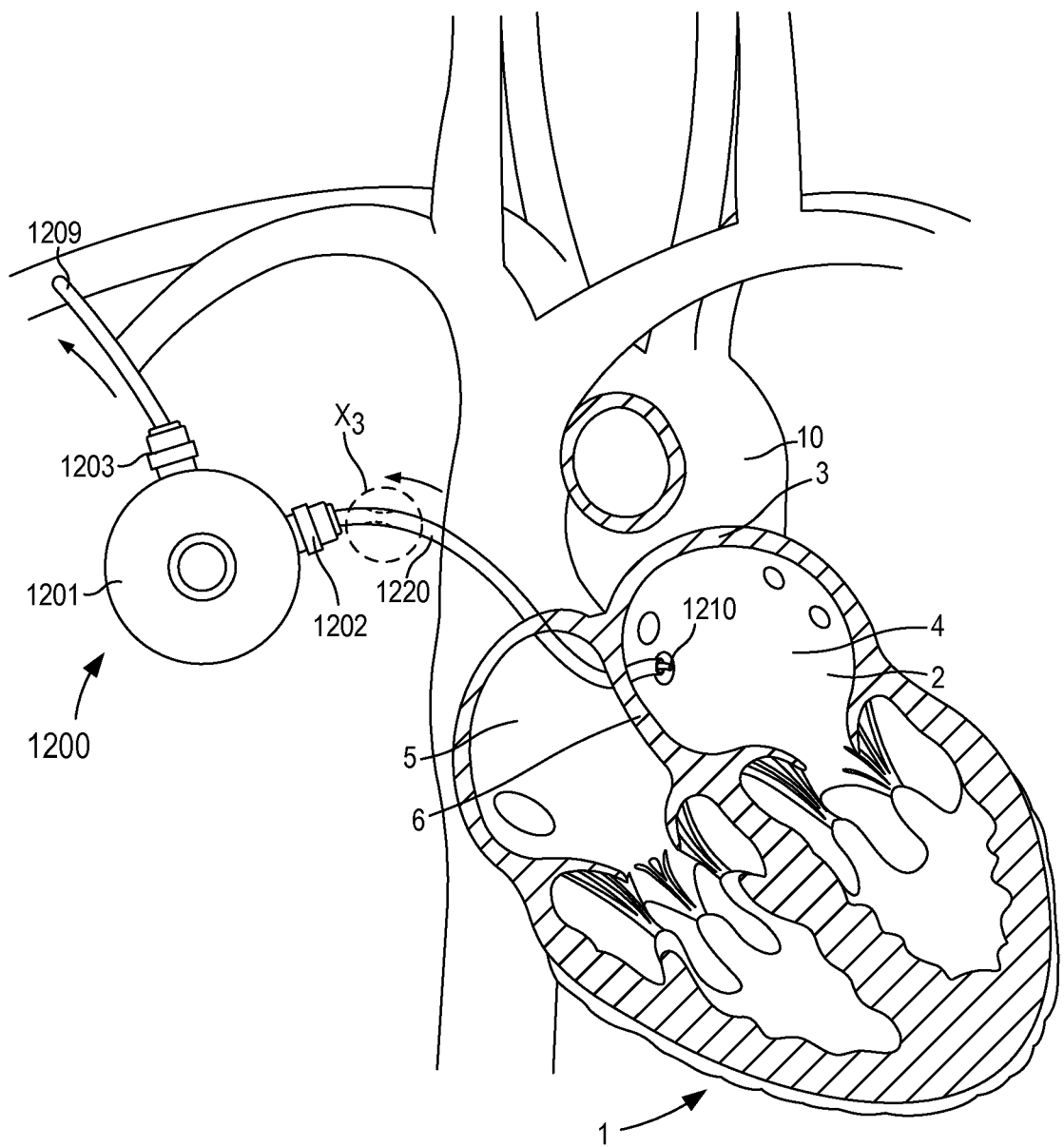
FIG. 16 is an illustration of an assist device in place within a portion of a body of a patient according to an embodiment.
Figure 17:
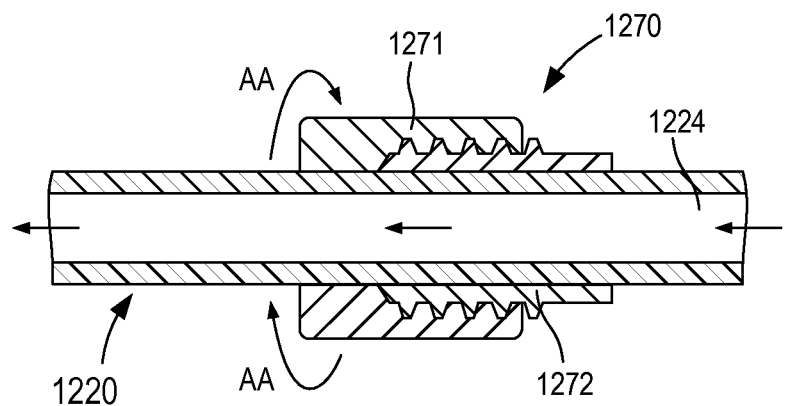
FIGS. 17 and 18 are enlarged cross-sectional illustrations of a portion of the assist device, identified by the region $X_3$ in FIG. 16, including a flow control mechanism in a first configuration and a second configuration, respectively, according to an embodiment.
Figure 18:
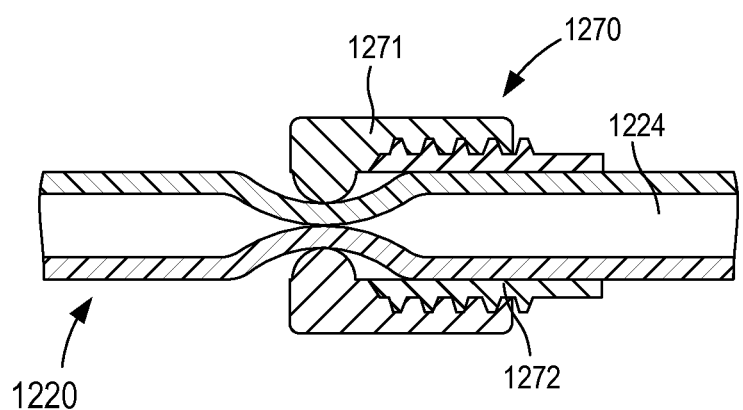

Any of the cannula assemblies described above can be used with a flow regulation mechanism or system to control a flow of blood from, for example, the left atrium to a pump of an assist device and/or from the pump of the assist device to the left atrium (e.g., via a recirculation member). A flow regulator can be any suitable mechanism that can be transitioned between a series of configurations to change a fluid flow characteristic through a lumen. For example, FIGS. 16-18 are illustrations of at least a portion of a VAD 1200 in fluid communication with the heart 1, according to an embodiment. The VAD 1200 includes a pump 1201, an outlet flow cannula 1209, a recirculation cannula 1210 (also referred to herein as a "recirculation member"), an inlet flow cannula 1220 (also referred to herein as a "cannula assembly"), and a flow regulator system 1270. The VAD 1200 can be configured to function substantially similar to the VAD 600 described above with reference to FIGS. 9 and 10. For example, the pump 1201 can include an inlet port 1202 and an outlet port 1203. The inlet port 1202 is physically and fluidically coupled to the inlet flow cannula 1220 such that blood can flow from the left atrium 2 to the pump 1201. Although not shown in FIG. 16, in some embodiments, the inlet port 1202 can be, for example, a dual port configuration that is physically and fluidically coupled to the inlet flow cannula 1220 and the recirculation cannula 1210. As such, the recirculation cannula 1210 can receive an outlet flow of blood from the pump 1201 and deliver the flow of blood to the left atrium 2, as described above with reference to the recirculation cannula 1210 of FIGS. 9 and 10. The outlet port 1203 is physically and fluidically coupled to the outlet flow cannula 1209 such that a flow of blood can be delivered, via the outlet flow cannula 1209, from the pump 1201 to the circulatory system, as described above.

As shown in FIGS. 17 and 18, the flow regulator system 1270 (also referred to herein as "flow regulator") can engage at least a portion of the recirculation cannula 1210 and/or at least a portion of the inlet flow cannula 1220 to regulate a flow of fluid therethrough. For example, as shown in FIGS. 17 and 18, in some embodiments, the flow regulator 1270 can be disposed about a portion of the inlet flow cannula 1220 and can be transitioned from a first configuration (FIG. 17) to a second configuration (FIG. 18) to regulate a flow of fluid (e.g., blood) through a lumen 1224 defined by the inlet flow cannula 1220. More particularly, the flow regulator 1270 includes a first member 1271 and a second member 1272 that can be moved relative to one another to restrict the lumen 1224 defined by the inlet flow cannula 1220. In some embodiments, the inlet flow cannula 1220 can be formed from a relatively flexible material that can be configured to bend, constrict, deflect, and/or otherwise deform when exposed to, for example, an external force.

In some instances, the first member 1271 can be rotated (e.g., by a motor, servo-motor, and/or the like not shown in FIGS. 17 and 18) relative to the second member 1272 to transition the flow regulator 1270 from the first configuration to the second configuration, as indicated by the arrow AA in FIG. 17. As a result, a portion of the first member 1271 can be placed in contact with an outer surface of the inlet flow cannula 1220 and can be configured to exert a force on the inlet flow cannula 1220 that is sufficient to deform at least portion of the inlet flow cannula 1220 such that the lumen 1224 becomes at least partially constricted. Similarly stated, the flow regulator 1270 can be configured to exert a force on the inlet flow cannula 1220 when in its second configuration to reduce an inner diameter of the inlet flow cannula 1220 associated with the lumen 1224. Thus, by constricting the inlet flow cannula 1220, a fluid flow rate therethrough can be reduced. Although shown in FIGS. 17 and 18 as being disposed about the inlet flow cannula 1220, in some embodiments, the flow regulator 1270 can be disposed about the recirculation cannula 1210, the inlet flow cannula 1220, and/or the outlet flow cannula 1209 or a combination thereof to reduce a flow rate through the recirculation cannula 1210, the inlet flow cannula 1220, and/or the outlet flow cannula 1209, respectively.

Figure 19:
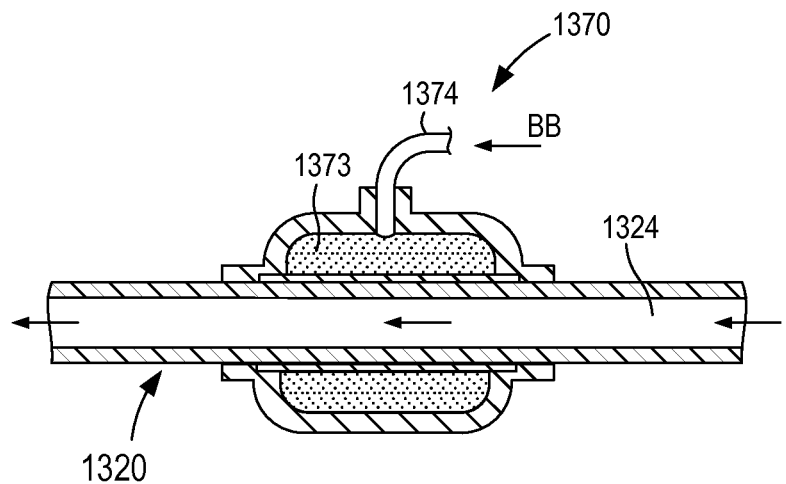
FIGS. 19 and 20 are enlarged cross-sectional illustrations of the portion of the assist device, identified by the region $X_3$ in FIG. 16, including a flow control mechanism in a first configuration and a second configuration, respectively, according to an embodiment.
Figure 20:
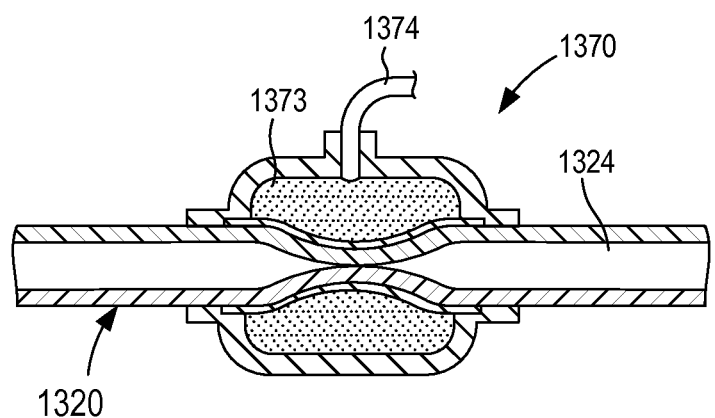

Although the flow regulator 1270 is shown in FIGS. 17 and 18 as being, for example, a screw-type regulator that can be rotated to regulate a flow through the inlet flow cannula 1220, in other embodiments, a VAD can include any suitable flow regulator. For example, FIGS. 19 and 20 are cross-sectional views of a flow regulator 1370 coupled to an inlet flow cannula 1320, according to an embodiment. The inlet flow cannula 1320 can be substantially similar to the inlet flow cannula 1320 described above. In this manner, the inlet flow cannula 1320 can be formed from a relatively flexible material such that, when exposed to an external force, a portion of the inlet flow cannula 1320 can deform, as described above. In some embodiments, the flow regulator 1320 can be formed from a material that is relatively inflexible (i.e., a material with a hardness that is larger than a hardness of the material forming the inlet flow cannula 1320) such that the flow regulator 1370 resists deformation when exposed to an external force. The flow regulator 1320 defines an inner volume 1373 in fluid communication with a port 1374. Moreover, as shown in FIGS. 19 and 20, the flow regulator 1320 is disposed about the inlet flow cannula 1320 such that a portion of the inlet flow cannula 1320 passes through the inner volume 1373.

In some instances, the port 1374 can receive a fluid (e.g., a fluid can be injected into the port 1374 by a motor, servo-motor, piston, and/or the like) such as saline or hydraulic oil, as indicated by the arrow BB in FIG. 19. The injection of the fluid can increase the inner volume 1373 to transition the flow regulator from a first configuration (FIG. 19) to a second configuration (FIG. 20). With the flow regulator 1370 being formed from a material with a greater hardness, the increase of the inner volume 1373 can deform a portion of the inlet flow cannula 1320 that is disposed within the inner volume 1373 such that a lumen 1324 defined by the inlet flow cannula 1320 is restricted. Thus, the flow regulator 1370 can be transitioned to its second configuration to control and/or regulate a flow of fluid through the inlet flow cannula 1320. Although shown in FIGS. 17 and 18 as being disposed about the inlet flow cannula 1220, in some embodiments, the flow regulator 1270 can be disposed about the recirculation cannula 1210, the inlet flow cannula 1220, and/or the outlet flow cannula 1209 or a combination thereof to reduce a flow rate through the recirculation cannula 1210, the inlet flow cannula 1220, and/or the outlet flow cannula 1209, respectively.

In some embodiments, a flow regulator can be controlled, for example, by a computer device and/or the like that can be configured to execute a set of instructions associated with controlling the flow regulator. For example, in some embodiments, information can be gathered to assist in the regulation of total pump flow and the amount of flow in the inflow and the recycled segments of the inflow cannula. Blood flow, pressure measurements, and/or blood oxygen saturation can be determined by one or more sensors in locations including, for example, inside the heart, an inlet flow cannula, a recirculation cannula, a pump, an outflow graft, and/or any other suitable location. In some instances, the pump motor speed, temperature, electrical current use, and/or the like can be used to provide information associated with, for example, a flow rate through a portion of the VAD and/or a portion of the heart (e.g., the left atrium). In some instances, a suction event can be determined based on, for example, a variation in pump motor speed and/or one or more vibration sensors. This information can be used to adjust the total pump flow and the amount of flow in each cannula (e.g., outlet flow, inlet flow, and/or recirculation). In other instances, any other pump parameters can be measured to determine the functioning of a portion of the VAD.

In some instances, a computer device, processor and/or the like included in the VAD can receive data that is associated with a suction event and can be configured to send a signal to one or more portions of the VAD to prevent and/or otherwise limit a suction event. For example, a suction occurrence can be determined based on low pressure in the inflow system or atrium, vibration in the pump, low flow in the inflow segment of the cannula, decreased energy consumption by the pump, variable pump motor speed signaling chatter, a drop in pump revolutions or other indicators. In response to determining an occurrence of a suction event, the computer device and/or the like can send a signal to one or more portions of the VAD to, for example, reducing overall pump flow. In some embodiments, the recycle flow can be relatively increased and the inflow to the pump can be relatively decreased, for example, via one or more flow regulators such as those described above. In other embodiments, resistors and/or the like can be incorporated into the pump and/or the connections of the cannula to the pump. In some embodiments, the computer device and/or the like can be configured to control more than one pump, as described above.

In some embodiments, the computer device can be configured to periodically determine a threshold or the like associated with the occurrence of a suction event by reducing pump flow. When suction occurs, the flow or the distribution of flow can be adjusted to provide, for example, a margin of safety and/or a suitable safety factor. In some embodiments, the computer device can determine the threshold in accordance to a predetermined time interval. For example, the computer device can be configured to determine the through several times per hour (e.g., 3 times per hour, 4 times per hour, 5 times per hour, 10 times per hour, 20 times per hour, etc.) to provide adjustments in flow rate and/or the like in response to a change in a patient's condition.

Although the cannula assemblies included in the embodiments described above in FIGS. 5-20 include a recirculation member that can be configured to support and/or otherwise limit movement, deformation and/or collapse of the wall of the left atrium relative to, for example, an inlet flow cannula, in other embodiments, a cannula assembly can include a support member that can be placed in contact with an inner surface of the atrial wall to support and/or limit movement of the wall relative to an inlet flow cannula. Similarly stated, in some embodiments, a cannula assembly can include a fluidic mechanism for stabilizing the structure of an organ (e.g., FIGS. 5-20), a mechanical mechanism for stabilizing the structure of an organ (e.g., FIGS. 1-3), or any combination thereof. Thus, in some embodiments, the support member can be a mechanical member and/or the like (e.g., a substantially solid support member rather than fluidic support).

For example, FIGS. 21-28 illustrate a portion of an inlet flow cannula assembly 1420, according to an embodiment. The inlet flow cannula assembly 1420 (also referred to herein as "cannula assembly") can be included in any of the VADs described herein. As such, the cannula assembly 1420 can be placed in contact with a wall 3 of a left atrium 2 of a heart 1 to place the left atrium 2 in fluid communication with, for example, a pump included in the device, as described in further detail herein.

The cannula assembly 1420 includes a tubular member 1421, an obturator 1448, a cap 1447, and a support member 1450 (see e.g., FIGS. 25-28). The tubular member 1421 includes a proximal end portion 1422 and a distal end portion 1423 and defines a lumen 1424 therethrough. The proximal end portion 1422 can be configured to be physically and fluidically coupled to an inlet port and/or the like of a pump included in a VAD (not shown in FIGS. 21-28). As described in further detail herein, the distal end portion 1423 of the tubular member 1421 can be transitioned between a first configuration, a second configuration, a third configuration, and a fourth configuration to couple the tubular member 1421 and thus, the cannula assembly 1420 to the wall 3 of the left atrium 2. Moreover, the distal end portion 1423 of the tubular member 1421 defines an opening 1427 that, when the distal end portion 1423 is in the fourth configuration (e.g., coupled to the wall 3), the opening 1427 places the lumen 1424 defined by the tubular member 1421 in fluid communication with an inner volume defined at least in part by the wall 3, as described in further detail herein.

Figure 21:
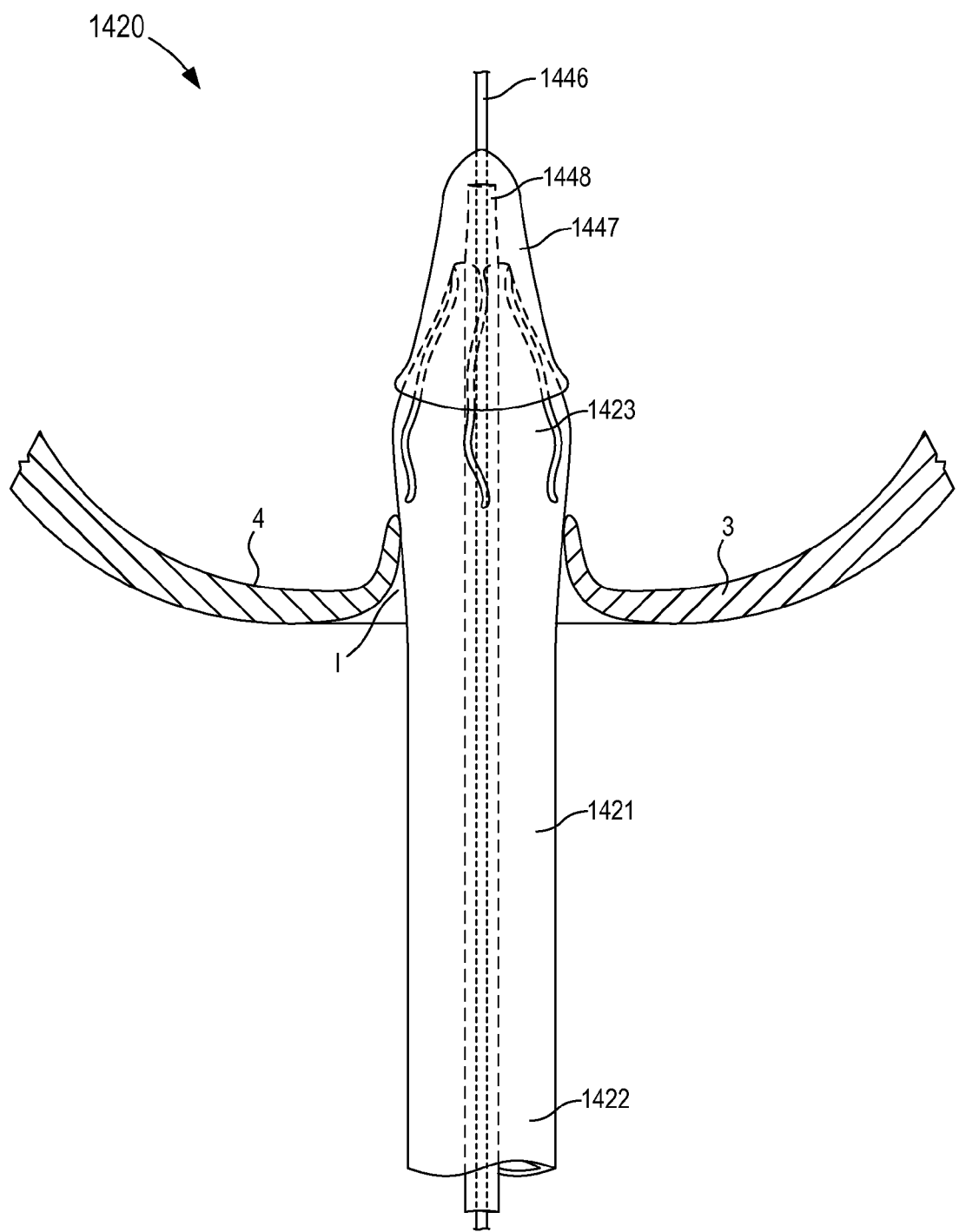
FIGS. 21-24 are illustrations of various stages of coupling a portion of an inlet flow cannula assembly to a wall of an atrium of a heart and being transitioned from a first configuration in FIG. 21 to a second configuration in FIGS. 23 and 24, according to an embodiment.
Figure 22:
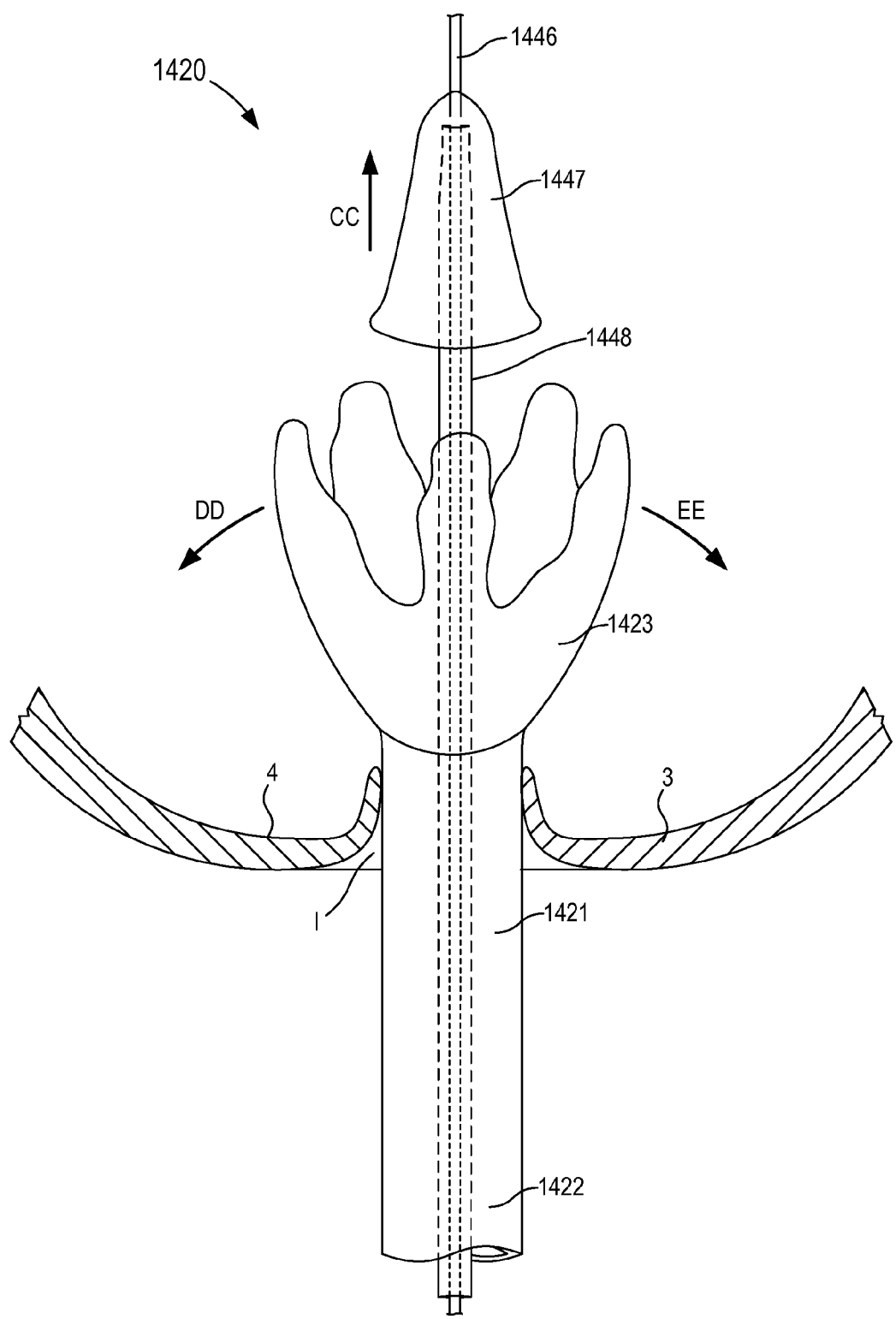

As shown in FIG. 21, the distal end portion 1423 of the tubular member 1421 can be moved along a guide wire 1446 to be inserted into an incision I made in the left atrial wall 3 of the heart. In some embodiments, the tubular member 1421 can be disposed within an introducer 1418 (see e.g., FIG. 25) while moved along the guide wire 1446. In other embodiments, the tubular member 1421 need not be disposed within the introducer 1418. The distal end portion 1423 can be maintained in the first configuration by disposing at least a portion of the distal end portion 1423 in the cap 1447 or other suitable structure. Once a desired part of the distal end portion 1423 is inserted through the incision I in the atrial wall 3, the cap 1447 and/or the tubular member 1421 can be moved relative to one another, thereby separating the cap 1447 from the distal end portion 1423 of the tubular member 1421, as indicated by the arrows CC, DD, and EE in FIG. 22.

Figure 23:
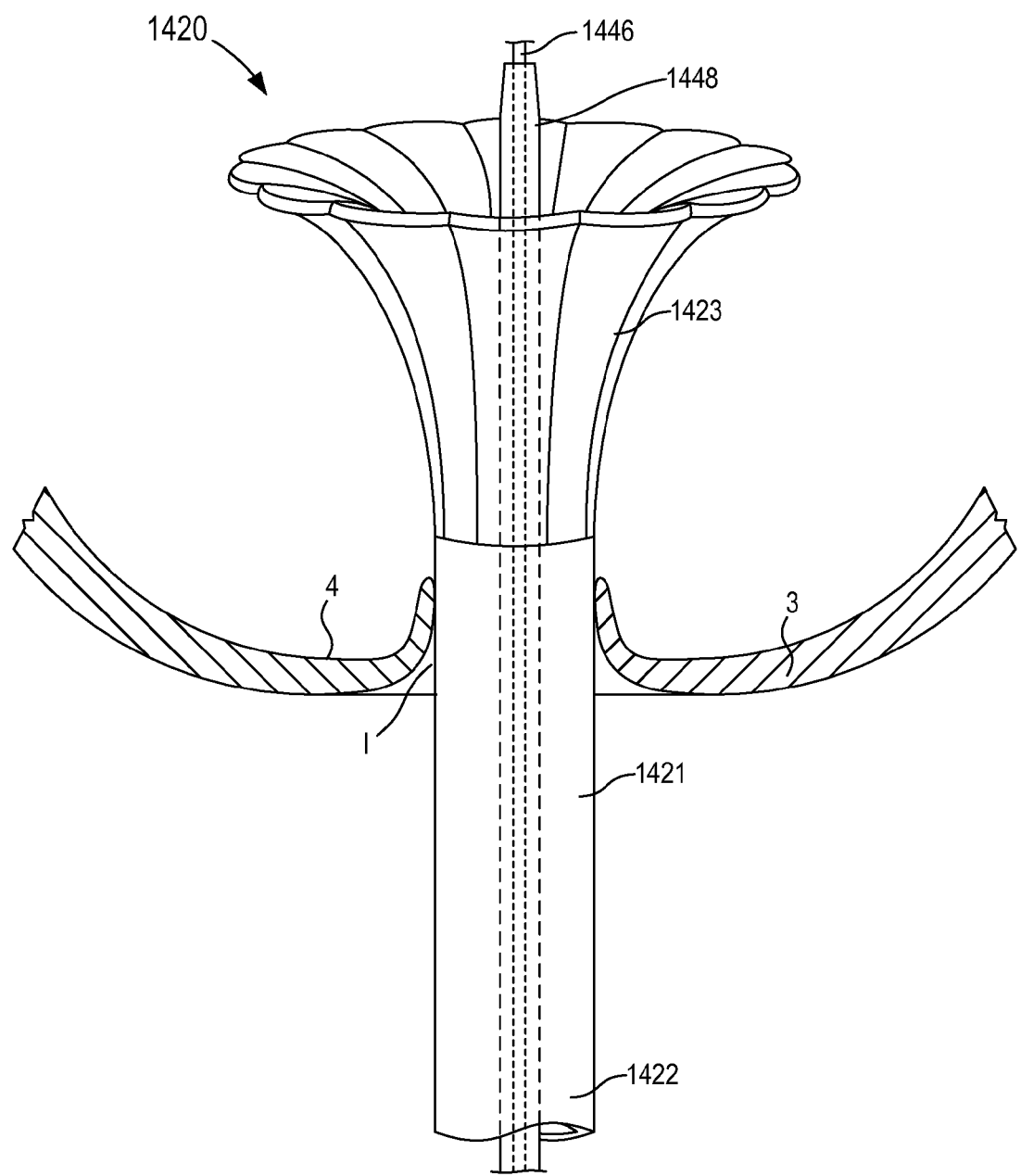

More specifically, the distal end portion 1423 (also referred to as the "connection portion" of the assembly) can include a perimeter that can be, for example, arranged in a non-linear (e.g., zig-zag) manner. In some embodiments, the distal end portion 1423 can include a wire or the like that can be substantially similarly shaped and disposed at or near the perimeter to provide structure that can allow the distal end portion 1423 to unfold. The configuration of the perimeter and/or of the wire can, for example, facilitate the folding and/or stability of the distal end portion 1423. In other embodiments, the distal end portion 1423 can be substantially circular and/or can include relatively small non-linear segments to effectively be substantially circular. In this manner, the distal end portion 1423 of the tubular member 1421 is allowed to unfold and/or otherwise transition from the first configuration to the second configuration (e.g., an expanded or open configuration), as shown in FIG. 23. Furthermore, once in the second configuration, the cap 1447 can be retracted through the lumen 1424 of the tubular member 1421 and removed from the patient.

Figure 24:
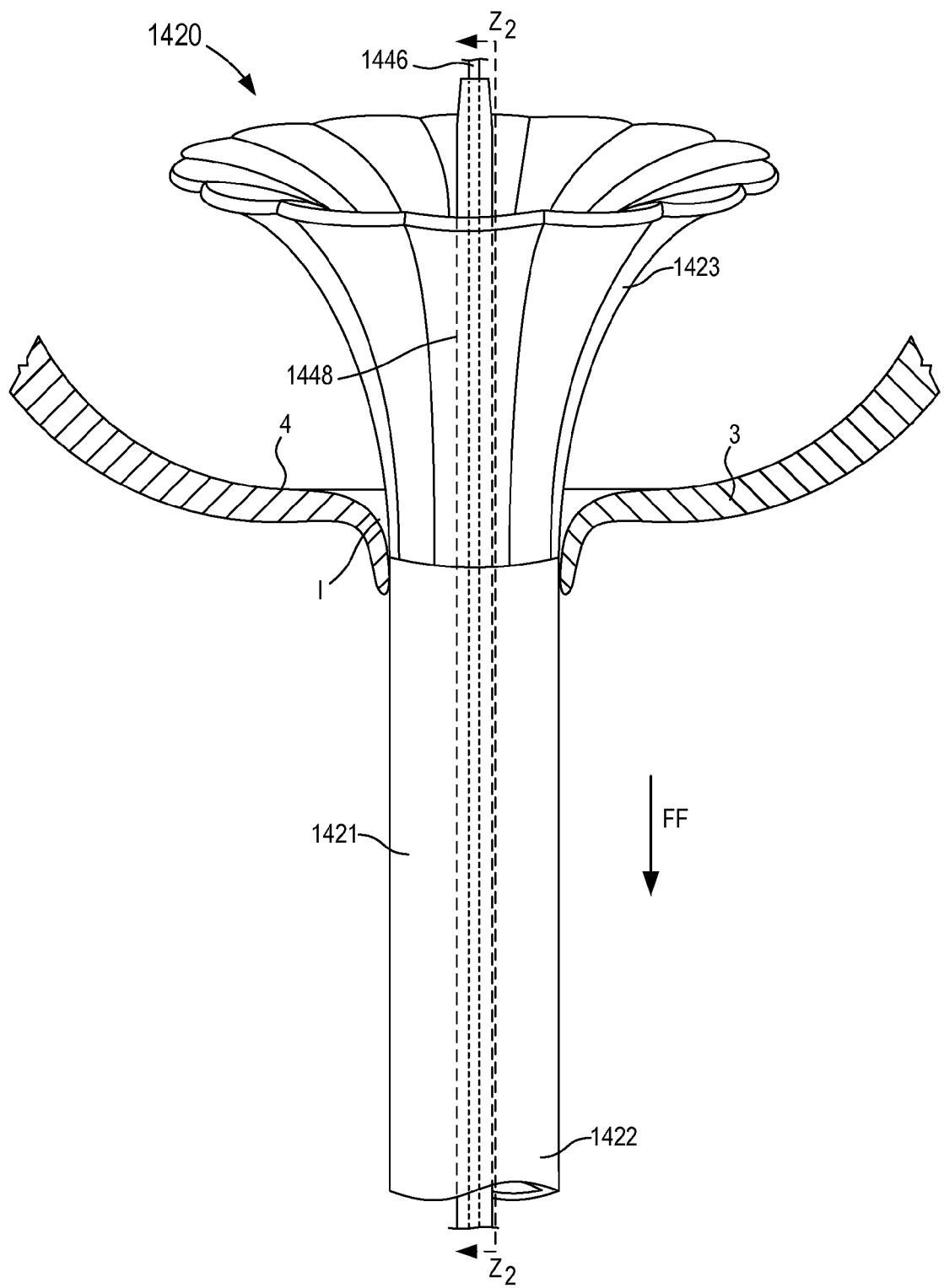

With the distal end portion 1423 in the second configuration, the tubular member 1421 can be retracted to move in a direction toward the atrial wall 3, as indicated by the arrow FF in FIG. 24. In some instances, the insertion of the tubular member 1421 can deform and/or otherwise move a portion of the atrial wall 3. In such instances, the movement of the tubular member 1421 (e.g., in the proximal direction) can move at least a portion of the atrial wall 3 in the proximal position that can, for example, return the atrial wall 3 to an undeformed and/or unmoved position and/or configuration, as shown in FIG. 24.

In some embodiments, prior to the distal end portion 1423 of the tubular member 1421 being placed in contact with an inner surface 4 of the wall 3, the support member 1450 can be moved in the distal direction to be disposed within the left atrium. The support member 1450 can be any suitable structure configured to provide, for example, mechanical support to at least a portion of the wall 3. For example, in some embodiments, the support member 1450 can be a wire, a mesh, a spring, a fabric, a sheet, a stent, a strut, a lobe, and/or any other suitable support structure. The support member 1450 can be formed from any suitable material such as, for example, metal (e.g., Nitinol®, stainless steel, etc.), biocompatible polymer (e.g., those described above), and/or the like. In some embodiments, the support member 1450 can include a covering or the like that can improve strength or biocompatibility such as, for example, polyester (e.g., Dacron®), Teflon®, Gore-Tex®, PTFE, and/or the like. In other embodiments, the support member 1450 can include a covering or the like that can be, for example, a fabric or the like that can facilitate tissue ingrowth and/or the like. In some embodiments, an outer surface of the support member 1450 can be roughened or textured to encourage tissue coverage. The support member 1450 can be configured to, for example, increase a surface area of the cannula assembly 1420 in contact with an inner surface 4 of the wall 3 such that movement of the wall 3 relative to the tubular member 1421 is limited, as described in further detail herein.

The arrangement of the support member 1450 can be such that as it inserted into the left atrium (i.e., beyond the wall 3), the cannula assembly 1420 limits and/or prevents undesirable contact of the support member 1420 with an inner surface 4 of the wall 3 (e.g., piercing, scraping, scarring, etc.). Moreover, an end portion of the support member 1450 can include a loop, hoop, rounded corner, etc. that can limit and/or prevent damage to the inner surface 4 of the wall 3. In some instances, the advancement and/or placement of the support member 1450 can be performed with an echocardiograph, a magnetic resonance image (MRI) scan, a computer tomography (CT) scan, and/or the like. Furthermore, the size and/or shape of the support member 1450 can be associated with and/or configured to conform to the anatomy of the inside of the left atrium, as described in further detail herein.

Figure 25:
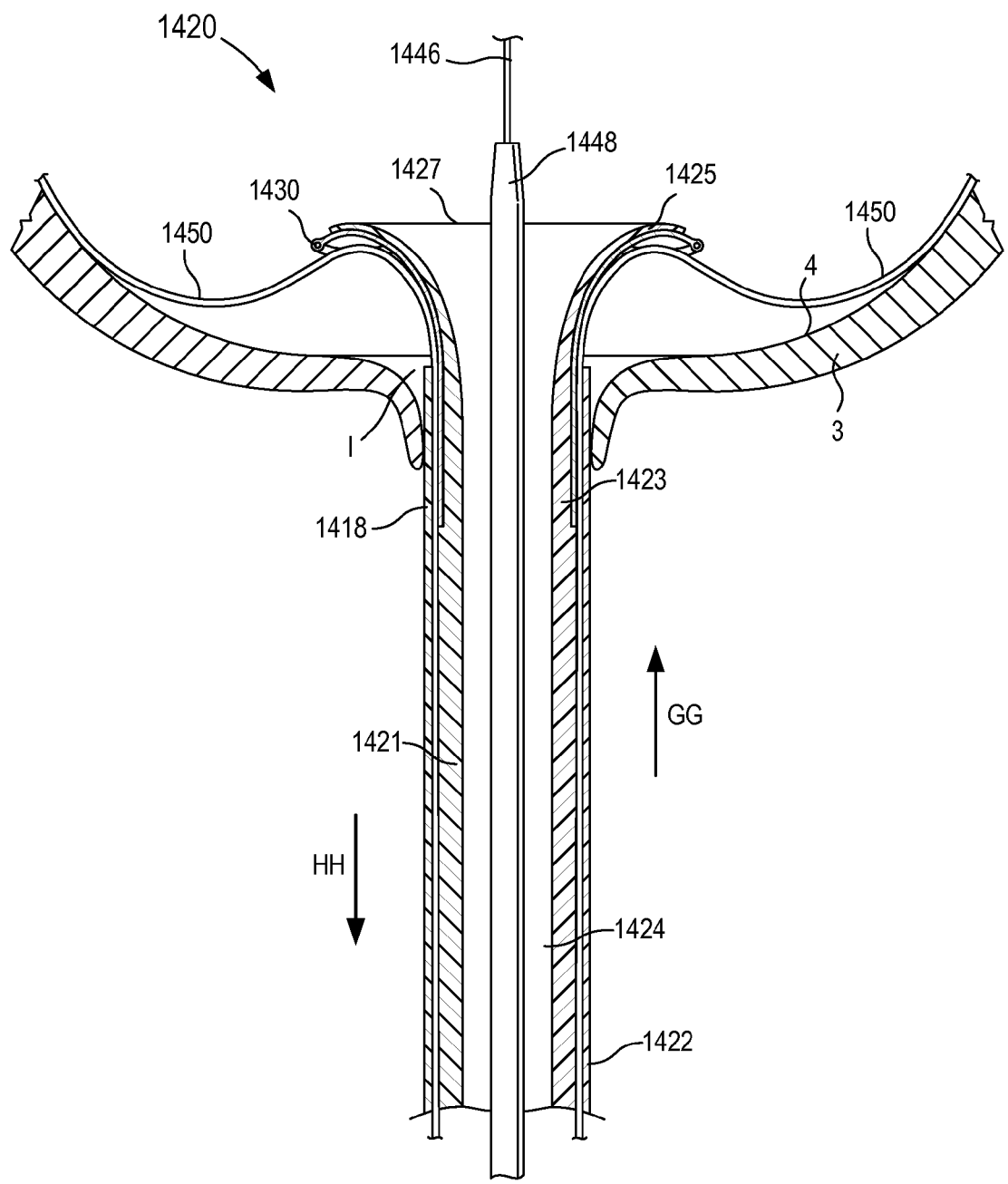
FIG. 25 is a cross-sectional illustration of the portion of the inlet flow cannula assembly of FIG. 21 taken along the line $Z_2$-$Z_2$ in FIG. 24, being transitioned from the second configuration to a third configuration.

In some embodiments, the support member 1450 can be advanced within the introducer 1418, as indicated by the arrow GG in FIG. 25. In other embodiments, the support member 1450 can be included in and/or operably coupled to the tubular member 1421 and advanced within a portion of the tubular member 1421 (e.g., within a channel defined by the tubular member 1421) and/or along an outer surface of the tubular member 1421. For example, in some embodiments, at least a portion of the support member 1450 can be advanced though the lumen 1424 of the tubular member 1421. In other embodiments, the tubular member 1421 can define one or more channel or the like (not shown in FIGS. 21-28) through which the support member 1450 can be advanced. In some such embodiments, the one or more channel can be, for example, a helical channel about a longitudinal centerline of the lumen 1424 (not shown) and fluidically isolated from the lumen 1424.

Although the support member 1450 is shown as changing positions relative to the tubular member 1421, in other embodiments, the support member can be included in and/or coupled to the distal end portion 1423 of the tubular member 1421. In such embodiments, the support member 1450 and can be configured to transition from a first, collapsed configuration to a second, expanded configuration. Similarly stated, the support member 1450 can be fixed, coupled, and/or otherwise included in the distal end portion 1423 of the tubular member 1421 and thus, not advanced in the GG direction relative to the tubular member 1421.

Figure 26:
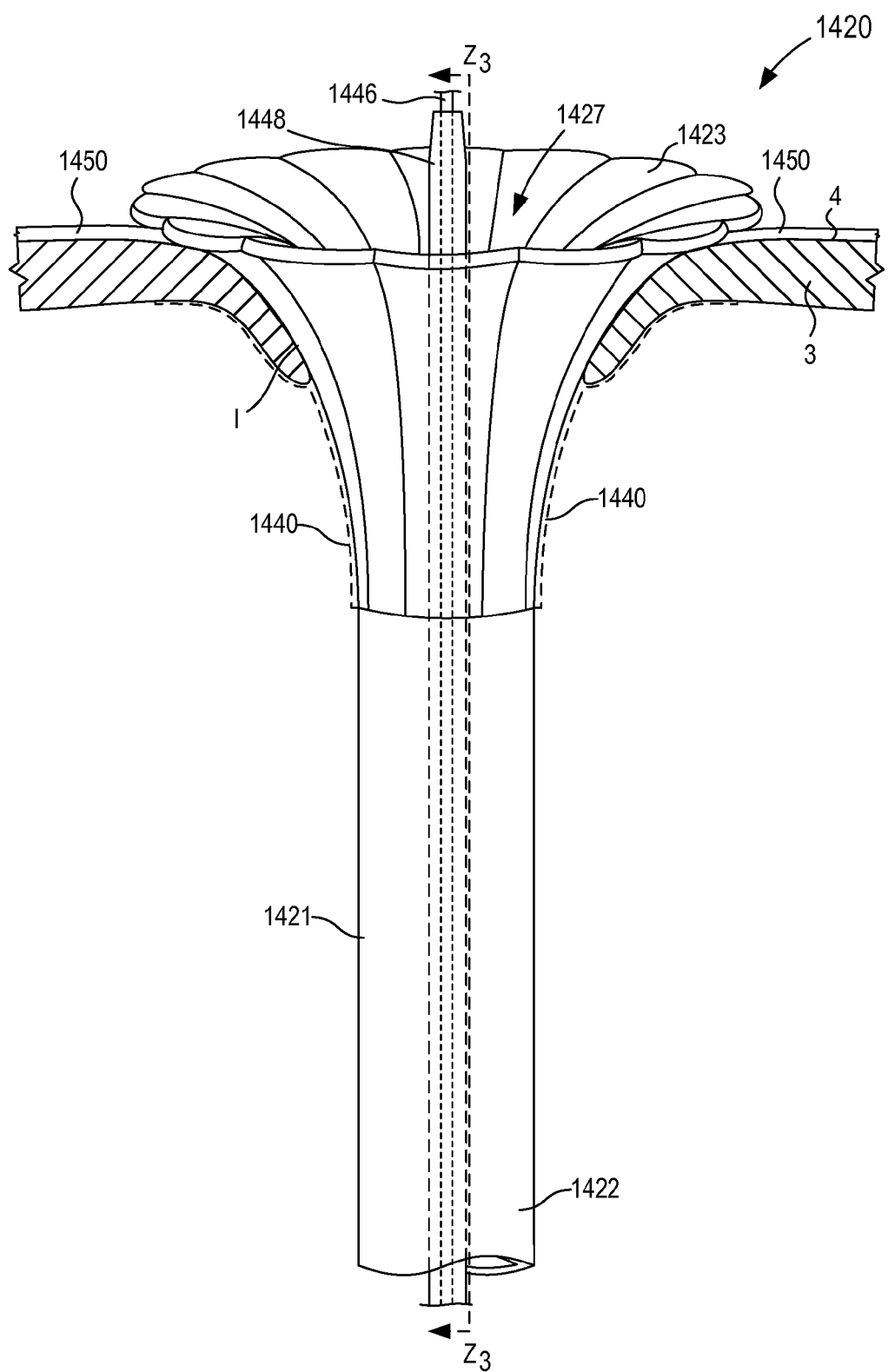
FIG. 26 is an illustration of the portion of the inlet flow cannula assembly of FIG. 21 in a third configuration.
Figure 27:
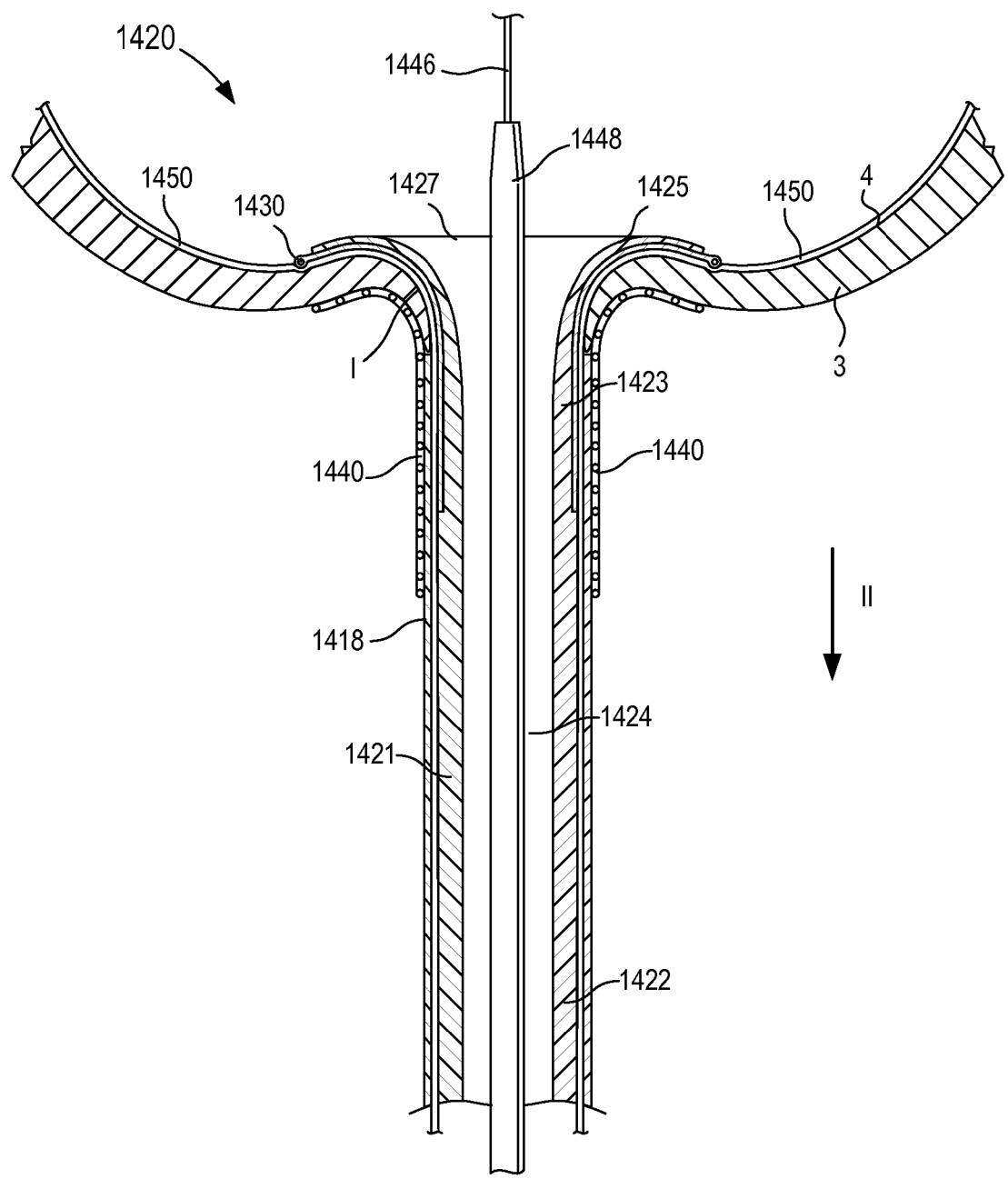
FIG. 27 is a cross-sectional illustration of the portion of the inlet flow cannula assembly of FIG. 21 taken along the line $Z_3$-$Z_3$ in FIG. 26, in the third configuration.

Once a desired portion of the support member 1450 is advanced into the left atrium, the cannula assembly 1420 can be moved in the distal direction toward the inner surface 4 of the wall 3, as indicated by the arrow HH in FIG. 25. Although the support member 1450 is shown as being disposed between the tubular member 1421 and the inner surface 4 of the wall 3, in other embodiments, the support member 1450 can extend from an outer perimeter (or margin) of the distal end portion 1423 of the tubular member 1421. As shown in FIGS. 26 and 27, the cannula member 1420 can be moved in the distal direction to place the support member 1450 and the distal end portion 1423 of the tubular member 1421 in contact with the inner surface 4 of the wall 3, thereby transitioning the cannula assembly 1420 from the second configuration to the third configuration. Although not shown in FIGS. 26 and 27, in some embodiments, the support member 1450 can include one or more anchors and/or the like that retain the support member 1450 in continuous contact with the inner surface 4, thereby reducing the likelihood of clot formation along the support member 1450.

As shown in FIGS. 26 and 27, the tubular member 1421 includes an inner retention member 1430 configured to engage the inner surface 4 and/or the support member 1450, and an outer retention member 1440 configured to engage an outer surface of the wall 3. The retention members 1430 and 1440 can be any suitable configuration. In some embodiments, the retention members 1430 and 1440 can be formed from a shape memory material such as Nitinol® or the like. In some embodiments, the retention members 1430 and 1440 can be bias members that can have a deformed configuration and an undeformed configuration. In such embodiments, the retention members 1430 and 1440 can be deformed such that the retention members 1430 and 1440 exert a force that resists the deformation (e.g., exert a force to return to the undeformed configuration). More specifically, as shown in FIG. 27, the inner retention member 1430 can be at least partially deformed when in contact with the inner surface 4 of the wall 3 and the outer retention member 1440 can be at least partially deformed when in contact with the outer surface of the wall 3. In this manner, the inner retention member 1430 and the outer retention member 1440 can exert a force that is substantially equal but in opposite directions. Thus, the inner retention member 1430 and the outer retention member 1440 collectively exert a compression force on the wall 3 of the left atrium that can be sufficiently large to couple the tubular member 1421 thereto. In some embodiments, the obturator 1448 can be transitioned from a collapsed configuration (as shown in FIG. 27) to an expanded configuration (not shown in FIGS. 21-28) to move at least the inner retention member 1430 towards the inner surface 4 of the wall 3. For example, in some embodiments, the obturator 1448 can be a balloon catheter or the like that can be inflated to move the obturator 1448 from its first configuration to its second configuration.

In some embodiments, the retention members 1430 and 1440 can include a set of anchors or the like that can retain the retention members 1430 and 1440 in continuous contact with the wall 3. In some embodiments, an inner surface of the retention members 1430 and/or 1440 can include, for example, an adhesive or the like that can couple the retention members 1430 to the wall 3. In other embodiments, the retention members 1430 and 1440 can be sutured to the wall 3. Thus, the retention members 1430 and 1440 can be retained in continuous contact with the wall 3, thereby reducing the likelihood of clot formation. Furthermore, the retention members 1430 and 1440 can aid in preventing the entry of fluid leak/air entry, and can ensure that the margin (e.g., an outer edge) of the distal end portion 1423 of the tubular member 1421 is securely pressed against the atrial wall 3. In some embodiments, the retention members 1430 and 1440 can be covered by a fabric and/or can include a surface finish to encourage healing into the heart tissue, as described in detail above. Although not shown, in some embodiments, once the retention members 1430 and 1440 are coupled to the wall 3, the obturator 1448 can be transitioned from its expanded configuration to its collapsed configuration.

Figure 28:
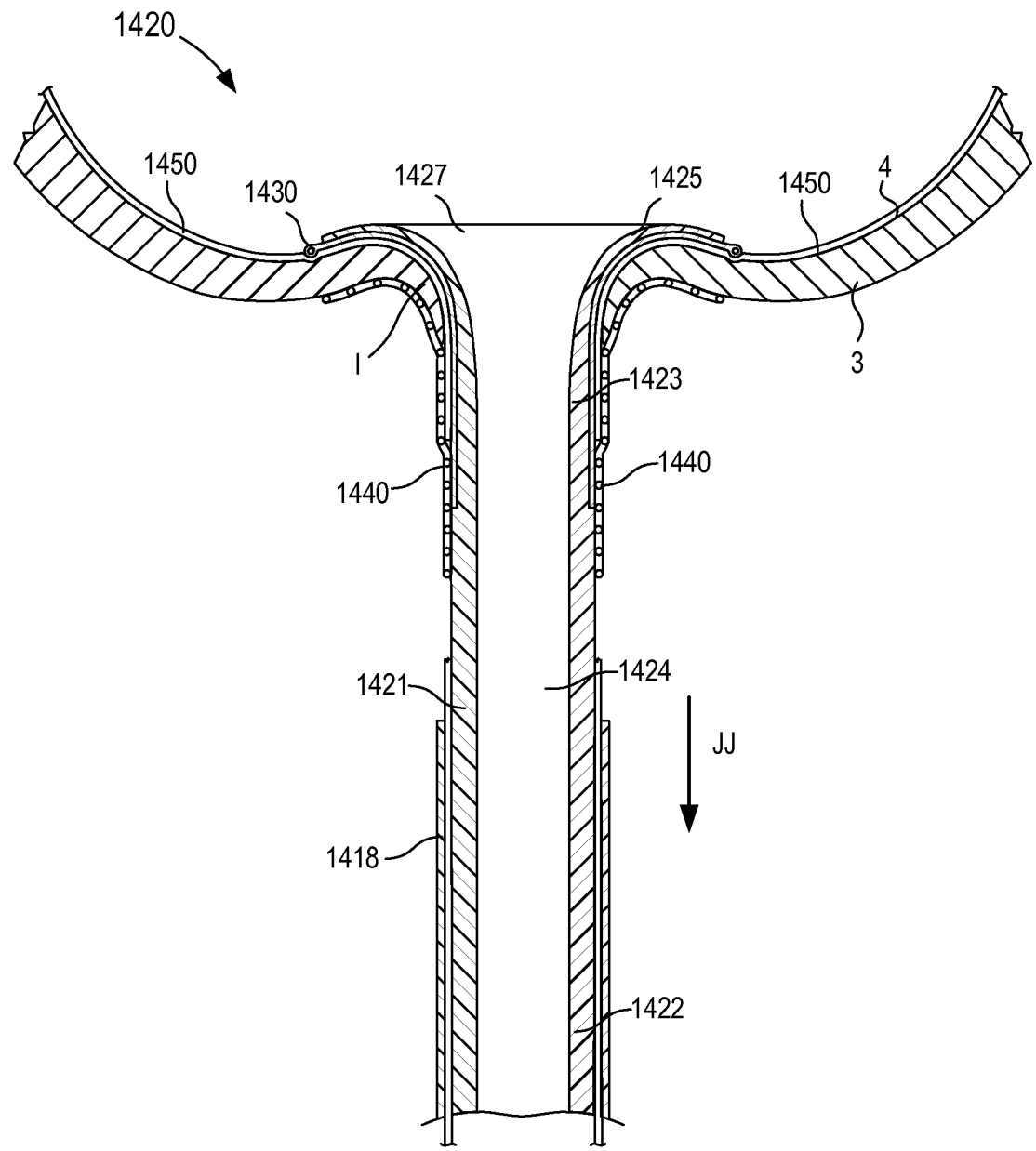
FIG. 28 is a cross-sectional illustration of the portion of the inlet flow cannula assembly of FIG. 21 taken along the line $Z_3$-$Z_3$ in FIG. 26, being transitioned from the third configuration to a fourth configuration.

With the retention members 1430 and 1440 in contact with the wall 3 and acting to couple the tubular member 1421 thereto, the introducer 1418, the guide wire 1445, and the obturator 1448 can be moved in the distal direction, as indicated by the arrow II in FIG. 27. Moreover, as the introducer 1418 is moved in the II direction, the outer retention member 1440 can be configured to conform to an outer surface of the tubular member 1421. For example, in some embodiments, with the introducer 1418 in a proximal position, a portion of the outer retention member 1440 can be in a deformed configuration such. Therefore, when the introducer 1418 is moved in the distal direction, the outer retention member 1440 exerts a force to transition the outer retention member 1440 towards its undeformed configuration (e.g., towards the tubular member 1421). In some embodiments, the movement of the introducer 1418 can, for example, expose an inner surface of the outer retention member 1440 that can include an adhesive or the like that can couple the a portion of the outer retention member 1440 to the tubular member 1421. In other embodiments, the inner surface of the outer retention member 1440 can include a set of anchors or the like that can couple the portion of the outer retention member 1440 to the tubular member 1421. Thus, the tubular member 1421 is secured to the wall 3. As shown in FIG. 28, with the tubular member 1421 coupled to the wall 3, the support member 1450 can be trimmed and/or a portion of the support member 1450 can be detached. In this manner, the introducer 1418 and the portion of the support members 1450 can be retracted relative to the tubular member 1421 and removed from the patient, as indicated by the arrow JJ in FIG. 28.

The arrangement of the support member 1450, the tubular member 1421, and the wall 3 can be such that the support member 1450 substantially limits movement and/or deformation of the wall relative to the tubular member 1421 when the tubular member 1421 is coupled thereto. In other words, the support member 1450 can support at least a portion of the wall 3 to limit and/or prevent deformation of the wall 3 that can otherwise result in a suction event (e.g., an obstruction of the opening 1427 and thus, the lumen 1424) and/or a kinking or obstruction of peripheral vascular structure such as, for example, the pulmonary vein or the like. Moreover, the support member 1450 can engage the inner surface 4 in such a way that the inner retention member 1430 and/or an outer edge of the tubular member 1421 is not pried away from the inner surface 4. In other words, the support member 1450 can exert a relatively uniform force on the inner surface 4 such that the support member 1450 does not act as a lever that would otherwise result in a force exerted on the inner retention member 1430 that would resist the force exerted by the inner retention member 1430. Thus, the likelihood of clot formation, the formation of dead spots in a flow of fluid within the left atrium, and/or the formation of eddy currents in a flow of fluid within the left atrium can be reduced or substantially prevented.

Figure 29:
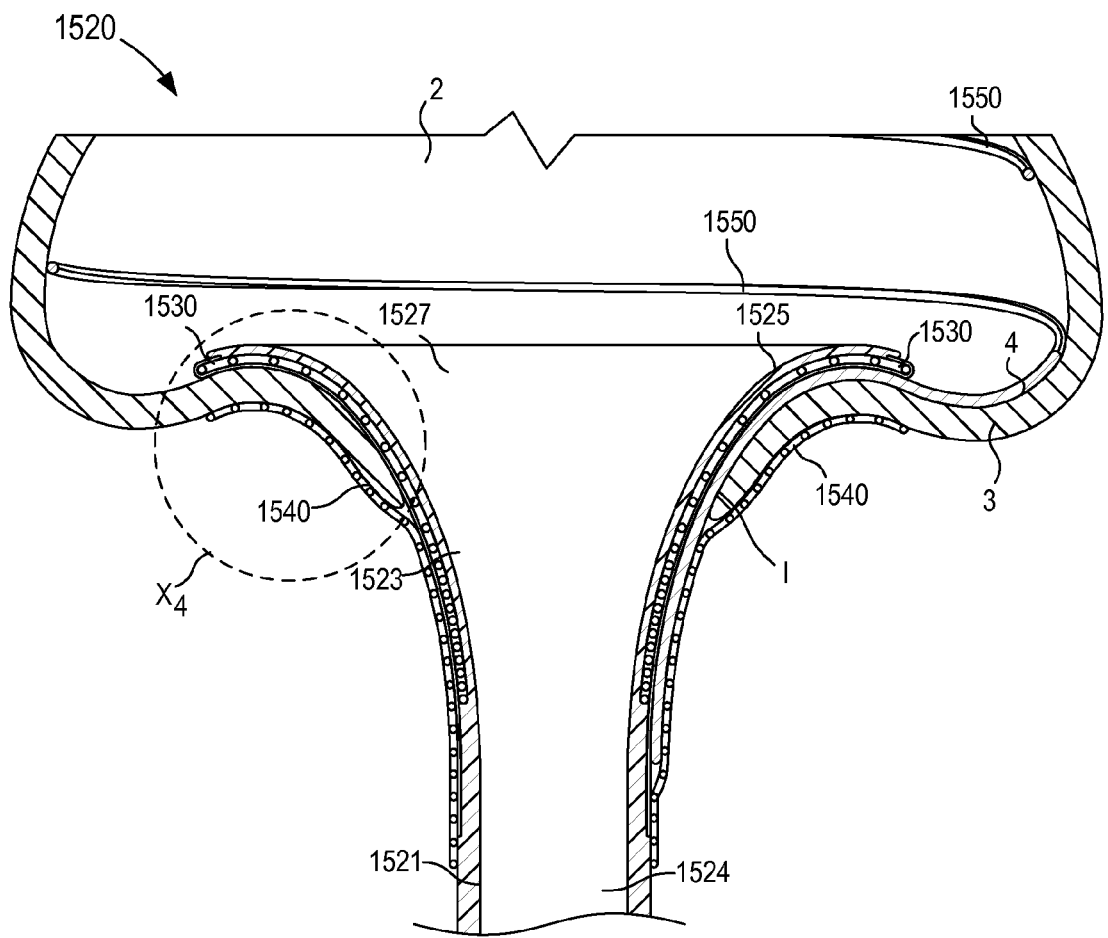
FIG. 29 is a cross-sectional illustration of a portion of an inlet flow cannula assembly according to an embodiment.
Figure 30:
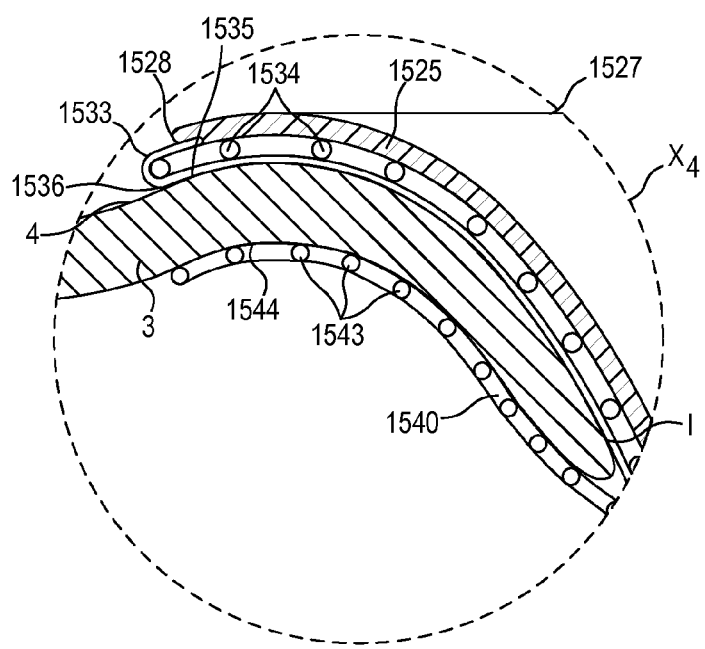
FIG. 30 is an enlarged view of a portion of the inlet flow cannula assembly of FIG. 29 identified by the region $X_4$.
Figure 31:
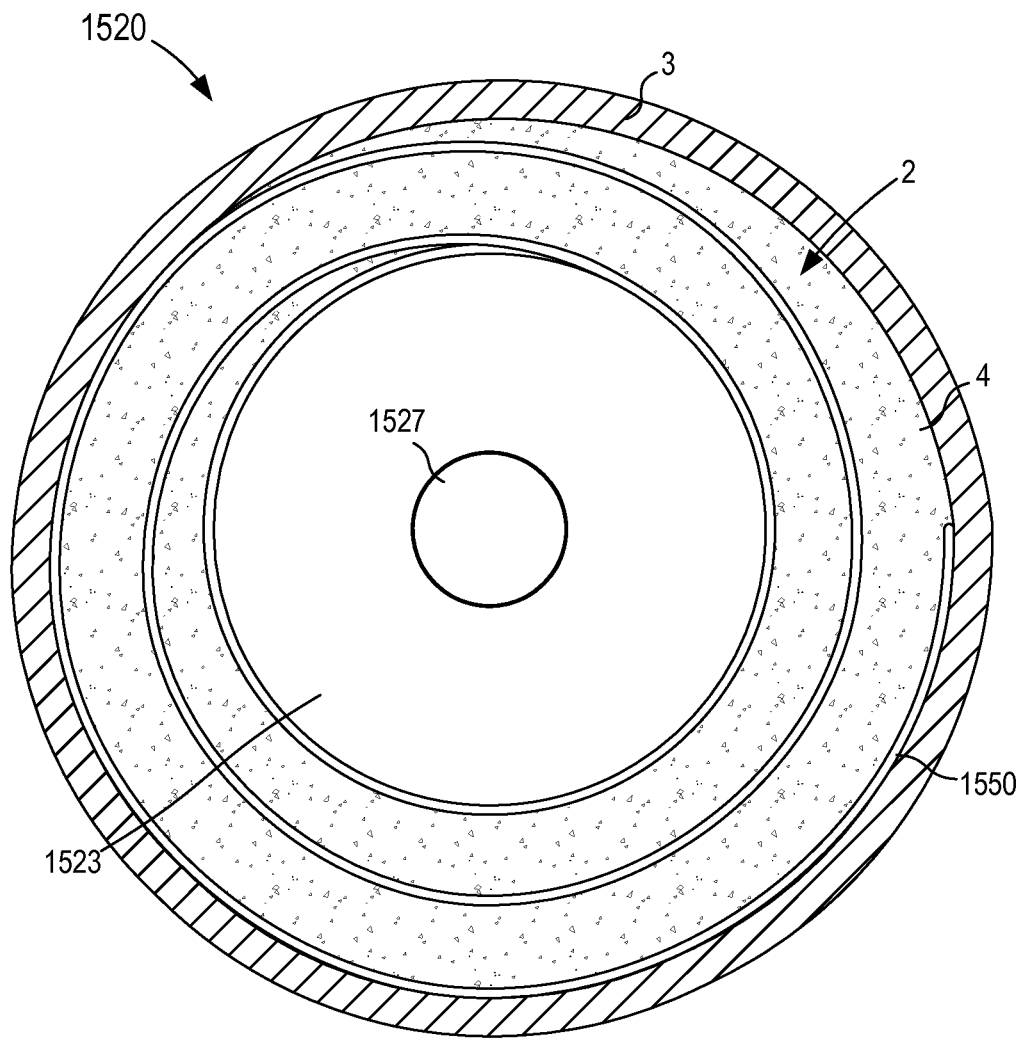
FIG. 31 is a top view of a portion of the inlet flow cannula assembly of FIG. 29 coupled to a wall of an atrium of a heart.

The support member 1450 and any of the support members shown and described herein can be any suitable member configured to stabilize the shape and/or size of the target organ and/or that can limit deformation and/or collapse thereof. For example, FIGS. 29-31 illustrate an inlet flow cannula assembly 1520 coupled to the wall 3 of the left atrium 2 of the heart 1 according to an embodiment. The inlet flow cannula assembly 1520 (also referred to herein as "cannula assembly") can be included in any of the VADs described herein. As such, the cannula assembly 1520 can be placed in contact with the wall 3 to place the left atrium 2 in fluid communication with, for example, a pump included in the device, as described in further detail herein.

The cannula assembly 1520 includes a tubular member 1521 and a support member 1550. The tubular member 1521 includes a proximal end portion (not shown in FIGS. 29-31) and a distal end portion 1523 and defines a lumen 1524 therethrough. The proximal end portion can be physically and fluidically coupled to an inlet port and/or the like of a pump included in a VAD. As described in further detail herein, the distal end portion 1523 of the tubular member 1521 defines an opening 1527 such that when the distal end portion 1523 is coupled to the wall 3 of the left atrium 2, the opening 1527 places the lumen 1524 in fluid communication with an inner volume (e.g., a chamber) of the left atrium 2. In some embodiments, portions of the tubular member 1521 can be substantially similar to portions of the tubular member 1421 described in detail above with reference to FIGS. 21-28. Thus, some aspects of the tubular member 1521 are not described herein and should be considered substantially similar in form and/or function to corresponding aspects of the tubular member 1421.

While the cannula assembly 1520 is shown in FIGS. 29-31 as being coupled to the wall 3, the cannula assembly 1520 can be positioned relative to the wall 3 and transitioned through a set of configurations in a similar manner as described in detail above with reference to the cannula assembly 1420. For example, as shown in FIGS. 29 and 30, the tubular member 1521 includes and/or is otherwise coupled to an inner retention member 1530 and an outer retention member 1540 that can collectively exert a compression force on the wall 3 to couple the distal end portion 1523 of the tubular member 1521 to the wall 3 of the left atrium 2, as described in detail above with reference to the retention members 1430 and 1440, respectively, of FIGS. 26-28. More specifically, inner retention member 1530 and the outer retention member 1540 include a bias member 1534 and 1543, respectively, that can exert a force that resists deflection and/or deformation of the retention members 1530 and 1540, respectively, as a result of the wall 3 being disposed therebetween, as shown in FIG. 30.

In some embodiments, the inner retention member 1530 and the outer retention member 1540 can include a set of anchors or the like (not shown in FIGS. 29-30) that can retain an inner surface 1535 of the inner retention member 1530 and an inner surface 1544 of the outer retention member 1540 in continuous contact with the wall 3. In other embodiments, the inner surfaces 1535 and 1544 can include, for example, an adhesive or the like that can couple the retention members 1530 to the wall 3. In other embodiments, the retention members 1530 and 1540 can be sutured to the wall 3. Thus, the inner surface 1535 of the inner retention member 1530 and the inner surface 1544 of the outer retention member 1540 can be retained in continuous contact with the wall 3, thereby reducing the likelihood of clot formation. Furthermore, the retention members 1530 and 1540 can aid in preventing the entry of fluid leak/air entry, and can ensure that the margin (e.g., an outer edge) of the distal end portion 1523 of the tubular member 1521 is securely pressed against and/or maintained in contact with the atrial wall 3.

The inner retention member 1530 includes a fabric 1533 and/or other cover or coating that can encourage healing into the heart tissue (as described as tissue ingrowth), as described in detail above. For example, in some embodiments, the fabric 1533 can be formed from Dacron® or the like. As shown in FIG. 30, a distal edge 1536 of the inner retention member 1530 extends beyond an outer edge (e.g., a margin or perimeter) of an inner portion 1525 of the tubular member 1521 to define a step 1528 or discontinuity between the inner retention member 1530 and the margin of the distal end portion 1523 of the tubular member 1521. In this manner, the fabric 1533 can substantially surround an exposed portion of the inner retention member 1530 and, in turn, can promote tissue growth from the inner surface 4 of the wall 3 to substantially surround the fabric 1533. The arrangement of the step 1528 can, for example, define a boundary and/or the like that can substantially limit the ingrowth of tissue about the tubular member 1521 such that the inner portion 1525 remains substantially free from tissue ingrowth. Moreover, in some embodiments, the inner portion 1525 can have a substantially smooth surface that can promote, for example, a laminar flow through the opening 1527 of the tubular member 1521 that would otherwise be disturbed (e.g., non-laminar or turbulent) by tissue ingrowth.

In some instances, prior to the distal end portion 1523 of the tubular member 1521 being coupled to the wall 3, the support member 1550 can be moved in the distal direction to be disposed within the left atrium. The support member 1550 can be any suitable structure configured to provide, for example, mechanical support to at least a portion of the wall 3. For example, as shown in FIGS. 29 and 31, the support member 1550 can be a wire that can extend from the distal end portion 1523 of the tubular member 1521. The support member 1550 can be formed from any suitable material such as, for example, a metal (e.g., Nitinol®, stainless steel, etc.), a biocompatible polymer (e.g., any of those described above), and/or the like. For example, in some embodiments, the support member 1550 can be formed from a shape memory alloy such as Nitinol® and can be configured to transition from a first configuration (e.g., during insertion into the left atrium 2) to a second configuration (e.g., an expanded configuration in which the surface is in substantially continuous contact with the inner surface 4 of the wall 3, as shown in FIGS. 29-31). In some embodiments, the support member 1550 can extend in a helical orientation such that the surface of the support member 1550 remains in substantially continuous contact with the inner surface 4 of the wall 3. In some embodiments, the pitch of the helix can be decreased or increased such that the number of times the support member 1550 is coiled along the inner surface 4 is increased or decreased, respectively.

The arrangement of the support member 1550 can be such that a desired amount of force is exerted by support member 1550 on the inner surface 4 of the wall 3 of the left atrium 2 that is sufficient to limit movement of the wall 3 relative to the tubular member 1521. In other words, the support member 1550 can support at least a portion of the wall 3 to limit and/or prevent deformation of the wall 3 that can otherwise result in a suction event (e.g., an obstruction of the opening 1527 and thus, the lumen 1524) and/or a kinking or obstruction of peripheral vascular structure such as, for example, the pulmonary vein or the like. For example, the support member 1550 can have a stiffness that can be sufficiently small to allow the support member 1550 to transition between the first configuration (not shown) and the second configuration (see e.g., FIGS. 29 and 31), yet sufficiently large to limit movement of the wall 3. As such, in some embodiments, the support member 1550 can for example, have a diameter that is associated with the desired stiffness. In other embodiments, the support member 1550 can be formed from one or more materials that can have a modulus of elasticity that can be associated with the desired stiffness. The support member 1550 is configured to engage the inner surface 4 such that the inner retention member 1530 and/or an outer edge of the tubular member 1521 is not pried away from the inner surface 4. In other words, the support member 1550 can exert a relatively uniform force on the inner surface 4 such that the support member 1550 does not act as a lever that would otherwise result in a force exerted on the inner retention member 1530 that would resist the force exerted by the inner retention member 1530. Thus, the likelihood of clot formation, the formation of dead spots in a flow of fluid within the left atrium, and/or the formation of eddy currents in a flow of fluid within the left atrium can be reduced or substantially prevented. In other embodiments, the force exerted by the support member 1550 can be asymmetrical (e.g., non-uniform) such that target areas of the wall 3 are exposed to a larger force than other areas of the wall 3.

In some embodiments, the overall size of the support member 1550 when in the second configuration can be based, at least in part, on a size of the left atrium 2 (as determined via an imaging technique or the like) such that the support member 1550 exerts the desired amount of force on the inner surface 4 of the wall 3 of the left atrium 3 to substantially limit and/or prevent movement of the wall 3 relative to the tubular member 1521. In some embodiments, the overall size of the support member 1550 in the second configuration can be, for example, about three times a diameter associated with the perimeter of the distal end portion 1523 of the tubular member 1521. Thus, the surface area of the cannula assembly 1520 that is in contact with the inner surface 4 of the wall 3 is increased and the support member 1550 can exert the desired amount of force on the inner surface 4 to limit movement of the wall 3 relative to the tubular member 1521.

In some embodiments, the support member 1550 can include a covering or the like that can improve strength or biocompatibility such as, for example, polyester (e.g., Dacron®), Teflon®, Gore-Tex®, PTFE, and/or the like. In other embodiments, the support member 1550 can include a covering or the like that can be, for example, a fabric or the like that can facilitate tissue ingrowth and/or the like. In some embodiments, an outer surface of the support member 1550 can be roughened or textured to encourage tissue coverage. Although not shown in FIGS. 29-31, the support member 1550 can include a loop, a hoop, a rounded corner, etc. that can limit and/or prevent damage to the inner surface 4 of the wall 3.

Although the support member 1550 is shown in FIG. 29 as being disposed between the inner retention member 1530 and the inner surface 4 of the wall 3, in other embodiments, a cannula assembly can include a support member that can, for example, extend through a surface defining the perimeter of a tubular member. For example, in some embodiments, the retention member 1530 can be in contact with the inner surface 4 of the wall 3 and the support member can be disposed between the retention member 1530 and the inner portion 1525 of the tubular member 1521. More specifically, in some embodiments, the support member 1550 can extend from or through the step 1528 or discontinuity (see e.g., FIG. 30) defined by the retention member 1530 and the tubular member 1521. Although not shown in FIGS. 29-31, in some embodiments, a portion of the fabric 1533 can include a surface that is substantially non-linear (e.g., a wave or zig-zag pattern) to allow, for example, the support member 1550 to pass through an inset of the surface of the fabric 1533. In some embodiments, the fabric 1533 can define an opening and/or the like through which the support member 1550 can extend.

Although the cannula assembly 1520 is shown and described as including a single support member 1550, in other embodiments, a cannula assembly can include more than one support member. For example, while the cannula assembly 1520 is shown in FIG. 29 as including the support member 1550 that extends from one side or one portion of the tubular member 1521, in other embodiments, a second support member, substantially similar to the support member 1550, can extend from an opposite side of portion of the tubular member 1521. In such embodiments, the support members 1550 can extend in substantially parallel helices along the inner surface 4 of the wall 3. In other embodiments, the cannula assembly 1520 can include a second support member that is, for example, concentric with a portion of the support member 1550. For example, a second support member can extend in a substantially parallel path, relative to the support member 1550, through a portion of the tubular member 1521. In such embodiments, the second support member can be, for example, disposed between the inner surface 1525 of the tubular member 1521 and the inner retention member 1530. In other embodiments, the second support member can be in a stacked configuration with the support member 1550 with, for example, a layer of fabric disposed therebetween. In still other embodiments, the support member 1550 and the second support member can be in an adjacent, non-stacked, configuration with or without a fabric therebetween. In some embodiments, the second support member can extend from the perimeter of the tubular member 1521 in a substantially curvilinear path towards the inner surface 4 of the wall 3. In such embodiments, the second support member can be configured to limit or prevent a force exerted by the support member 1550 from prying the inner retention member 1530 from contact with the inner surface 4 of the wall 3.

Figure 32:
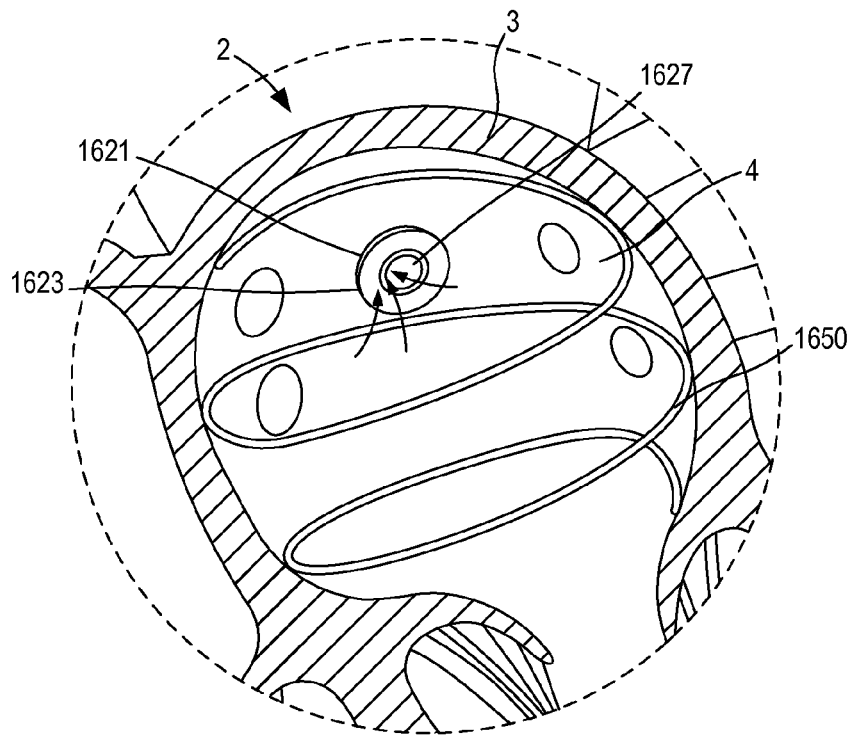
FIGS. 32-35 are illustrations of a portion of an inlet flow cannula assembly coupled to a wall of an atrium of a heart, each according to an embodiment.

Although the support member 1550 is shown and described as extending from the tubular member 1521 (i.e., coupled to the tubular member 1521), in other embodiments, a support member can be delivered to, for example, the left atrium to support a wall of the atrium relative to an inflow cannula without being coupled to the inflow cannula. For example, FIG. 32 is an illustration of a tubular member 1621 and a support member 1650 coupled to and/or otherwise engaging a wall 3 of the left atrium 2, according to an embodiment. The tubular member 1621 can be included in, for example, an inlet flow cannula such as those described above. The tubular member 1621 has a distal end portion 1623 that is in contact with an inner surface 4 of the wall 3, as described above. Moreover, the distal end portion 1623 defines an opening 1627 that can be configured to place the left atrium 2 in fluid communication with a lumen (not shown) defined by the tubular member 1621. Thus, blood can flow from the left atrium 2 to, for example, a pump included in a VAD (not shown), as described in detail above.

The support member 1650 can be substantially similar in at least function as the support member 1550 described above with reference to the cannula assembly 1520. In some embodiments, the support member 1650 can be in a first configuration (e.g., a relatively linear configuration) and advanced through, for example, the lumen defined by the tubular member 1621 to be delivered to the left atrium 2, wherein the support member 1650 can be transitioned to a second configuration (e.g., a helical configuration). In some embodiments, the support member 1650 can be formed from a wire or the like and arranged in a helical configuration such that a surface of the support member 1650 is maintained in substantially continuous contact with the inner surface 4 of the wall 3, as described in detail above. Furthermore, the support member 1650 can have an overall size that is associated with a size of the left atrium 2 (e.g., as determined via an imaging technique). Thus, the support member 1650 can be configured to exert a desired amount of force on the inner surface 4 of the wall 3 of the left atrium 2 to substantially limit movement of the wall 3 relative to the tubular member 1621 that can otherwise result in a suction event (e.g., an obstruction of the opening 1627) and/or a kinking or obstruction of peripheral vascular structure such as, for example, the pulmonary vein or the like.

As shown in FIG. 32, the support member 1650 can be deployed in the left atrium 2 such that the region of the mitral valve is substantially open such that a flow of blood into the left ventricle is substantially unobstructed. Similarly, the support member 1650 can be deployed in the left atrium 2 such that the openings defined in the wall 3 that are associated with the pulmonary veins and/or other vascular structures are substantially unobstructed. In other embodiments, the support member 1650 can cover the mitral valve orifice and/or one or more openings defined by the wall 3. Although the support member 1650 is shown as supporting substantially the entire left atrium 2, in other embodiments, the support member 1650 can be configured to support only a portion of the wall 3 of the left atrium 2. For example, in some instances, strutting open the pulmonary veins and the dome of the left atrium 2 can be sufficient to prevent atrial collapse. In other instances, the dome of the left atrium 2 need not be supported. In some instances, a support member 1650 can stent or support just a portion of the left atrium 2 so that the tubular member 1621 maintains a fluid connection with the pulmonary veins (left and right) when the left atrium 2 is placed under suction. In some embodiments, the support member 1650 can join the pulmonary veins and the tubular member 1621.

In some instances, a support member 1650 can extend across the dome of the left atrium 2 and the pulmonary veins would remain splayed open when suction was applied. Thus a support member 1650 supporting the dome left atrium 2 can provide an unobstructed inflow to the tubular member 1621 from the pulmonary veins even when suction occurs that would ordinarily collapse the atrium 2.

In some embodiments, the support member 1650 can include a covering or the like that can improve strength or biocompatibility such as, for example, polyester (e.g., Dacron®), Teflon®, Gore-Tex®, PTFE, and/or the like. In other embodiments, the support member 1650 can include a covering or the like that can be, for example, a fabric or the like that can facilitate tissue ingrowth and/or the like. In some embodiments, an outer surface of the support member 1650 can be roughened or textured to encourage tissue coverage. Although not shown in FIG. 32, the support member 1650 can include end portions that form, for example, a loop, a hoop, a rounded corner, etc. that can limit and/or prevent damage to the inner surface 4 of the wall 3, as described in detail above.

Figure 33:
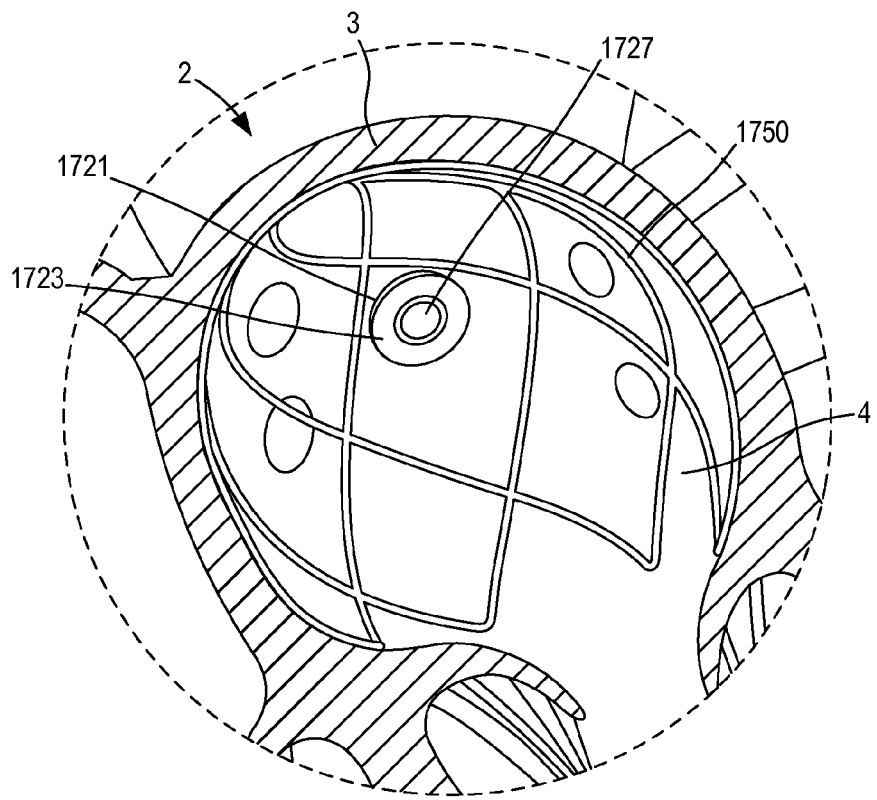

Although the support members 1550 and 1650 are shown as being arranged in a helical configuration, in other embodiments, a cannula assembly can include a support member in any suitable configuration. For example, FIG. 33 is an illustration of a tubular member 1721 and a support member 1750 coupled to and/or otherwise engaging a wall 3 of the left atrium 2, according to an embodiment. The tubular member 1721 can be included in, for example, an inlet flow cannula such as those described above. The tubular member 1721 has a distal end portion 1723 that is in contact with an inner surface 4 of the wall 3, as described above. Moreover, the distal end portion 1723 defines an opening 1727 that can be configured to place the left atrium 2 in fluid communication with a lumen (not shown) defined by the tubular member 1721. Thus, blood can flow from the left atrium 2 to, for example, a pump included in a VAD (not shown), as described in detail above.

The support member 1750 can be substantially similar in function as the support members 1550 and 1650 described above. In some embodiments, the support member 1750 can be in a first configuration (e.g., a relatively collapsed configuration) and advanced through, for example, the lumen defined by the tubular member 1721 to be delivered to the left atrium 2, wherein the support member 1750 can be transitioned to a second configuration (e.g., a mesh or grid configuration). In some embodiments, the support member 1750 can be formed from a wire or the like and arranged in a mesh configuration such that a surface of the support member 1750 is maintained in substantially continuous contact with the inner surface 4 of the wall 3, as described in detail above. In some embodiments, the wire mesh forming the support structure 1750 can be substantially continuous. In other embodiments, the wire mesh forming the support structure 1750 can be segmented. Although shown as being distinct from the tubular member 1721, in some embodiments, the support member 1750 can be coupled to the distal end portion 1723 of the tubular member 1721.

Furthermore, the support member 1750 can have an overall size that is associated with a size of the left atrium 2 (e.g., as determined via an imaging technique). Thus, the support member 1750 can be configured to exert a desired amount of force on the inner surface 4 of the wall 3 of the left atrium 2 to substantially limit movement of the wall 3 relative to the tubular member 1721 that can otherwise result in a suction event (e.g., an obstruction of the opening 1727) and/or a kinking or obstruction of peripheral vascular structure such as, for example, the pulmonary vein or the like, as described in detail above.

As shown in FIG. 33, the support member 1750 can be deployed in the left atrium 2 such that the region of the mitral valve is substantially open such that a flow of blood into the left ventricle is substantially unobstructed. Similarly, the support member 1750 can be deployed in the left atrium 2 such that the openings defined in the wall 3 that are associated with the pulmonary veins and/or other vascular structures are substantially unobstructed. In other embodiments, the support member 1750 can cover the mitral valve orifice and/or one or more openings defined by the wall 3. Although the support member 1750 is shown as supporting substantially the entire left atrium 2, in other embodiments, the support member 1750 can be configured to support only a portion of the wall 3 of the left atrium 2, as described above.

In some embodiments, the support member 1750 can include a covering or the like that can improve strength or biocompatibility such as, for example, polyester (e.g., Dacron®), Teflon®, Gore-Tex®, PTFE, and/or the like. In other embodiments, the support member 1750 can include a covering or the like that can be, for example, a fabric or the like that can facilitate tissue ingrowth and/or the like. In some embodiments, an outer surface of the support member 1750 can be roughened or textured to encourage tissue coverage. Although not shown in FIG. 33, the support member 1750 can include end portions that form, for example, a loop, a hoop, a rounded corner, etc. that can limit and/or prevent damage to the inner surface 4 of the wall 3, as described in detail above.

Figure 34:
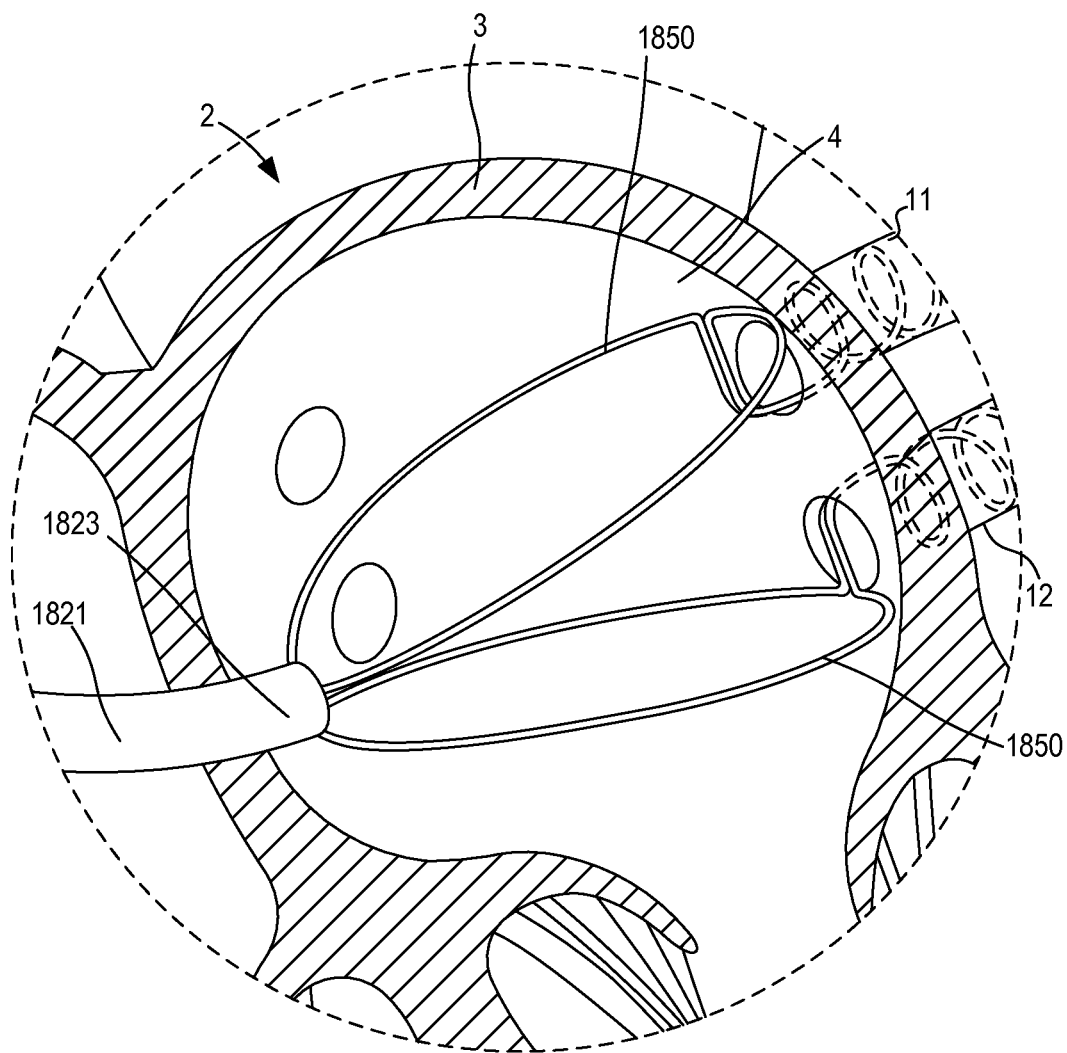

Although the support members 1650 and 1750 are shown as being distinct from the tubular members 1621 and 1721, respectively, a support structure can be disposed within and/or coupled to a portion of a tubular member. Moreover, in some embodiments, a tubular member can be coupled to more than one support member. For example, FIG. 34 is an illustration of a tubular member 1821 and a set of support members 1850 coupled to a wall 3 of the left atrium 2. The tubular member 1821 can be included in, for example, an inlet flow cannula such as those described above. The tubular member 1821 has a distal end portion 1823 that is in contact with an inner surface 4 of the wall 3, as described above. Moreover, the distal end portion 1823 can define an opening (not shown) that can be configured to place the left atrium 2 in fluid communication with a lumen (not shown) defined by the tubular member 1821. Thus, blood can flow from the left atrium 2 to, for example, a pump included in a VAD (not shown), as described in detail above.

The support members 1850 can be substantially similar in function as the support members 1550, 1650, and/or 1750 described above. In some embodiments, the support members 1850 can be in a first configuration (e.g., a relatively collapsed configuration) and advanced through, for example, the lumen defined by the tubular member 1821 to be delivered to the left atrium 2, wherein the support member 1850 can be transitioned to a second configuration (e.g., a looped or expanded configuration). In some embodiments, the support member 1850 can be formed from a wire or the like and arranged in a loop configuration such that a surface of the support member 1850 is maintained in substantially continuous contact with the inner surface 4 of the wall 3, as described in detail above. Moreover, as shown in FIG. 34, the support members 1850 can include a portion that can be inserted into one or more pulmonary veins 11 and 12. In this manner, the support members 1850 can be anchored such that their position within the left atrium 2 is substantially fixed. The support members 1850 can have an overall size that is associated with a size of the left atrium 2 (e.g., as determined via an imaging technique). Thus, the support members 1850 can be configured to exert a desired amount of force on the inner surface 4 of the wall 3 of the left atrium 2 to substantially limit movement of the wall 3 relative to the tubular member 1821 that can otherwise result in a suction event (e.g., an obstruction of the opening defined by the tubular member 1821) and/or a kinking or obstruction of peripheral vascular structure such as, for example, the pulmonary veins 11 and 12 shown in FIG. 34.

In some embodiments, the support members 1850 can include a covering or the like that can improve strength or biocompatibility such as, for example, polyester (e.g., Dacron®), Teflon®, Gore-Tex®, PTFE, and/or the like. In other embodiments, the support members 1850 can include a covering or the like that can be, for example, a fabric or the like that can facilitate tissue ingrowth and/or the like. In some embodiments, an outer surface of the support members 1850 can be roughened or textured to encourage tissue coverage. Although not shown in FIG. 34, the support members 1850 can include end portions that form, for example, a loop, a hoop, a rounded corner, etc. that can limit and/or prevent damage to the inner surface 4 of the wall 3, as described in detail above.

Although the support members 1850 are shown in FIG. 34 as each being formed from a single wire, in other embodiments, the supports members 1850 can form a mesh or the like that can include a portion that is configured to be inserted into and/or otherwise engage the pulmonary veins 11 and 12.

Figure 35:
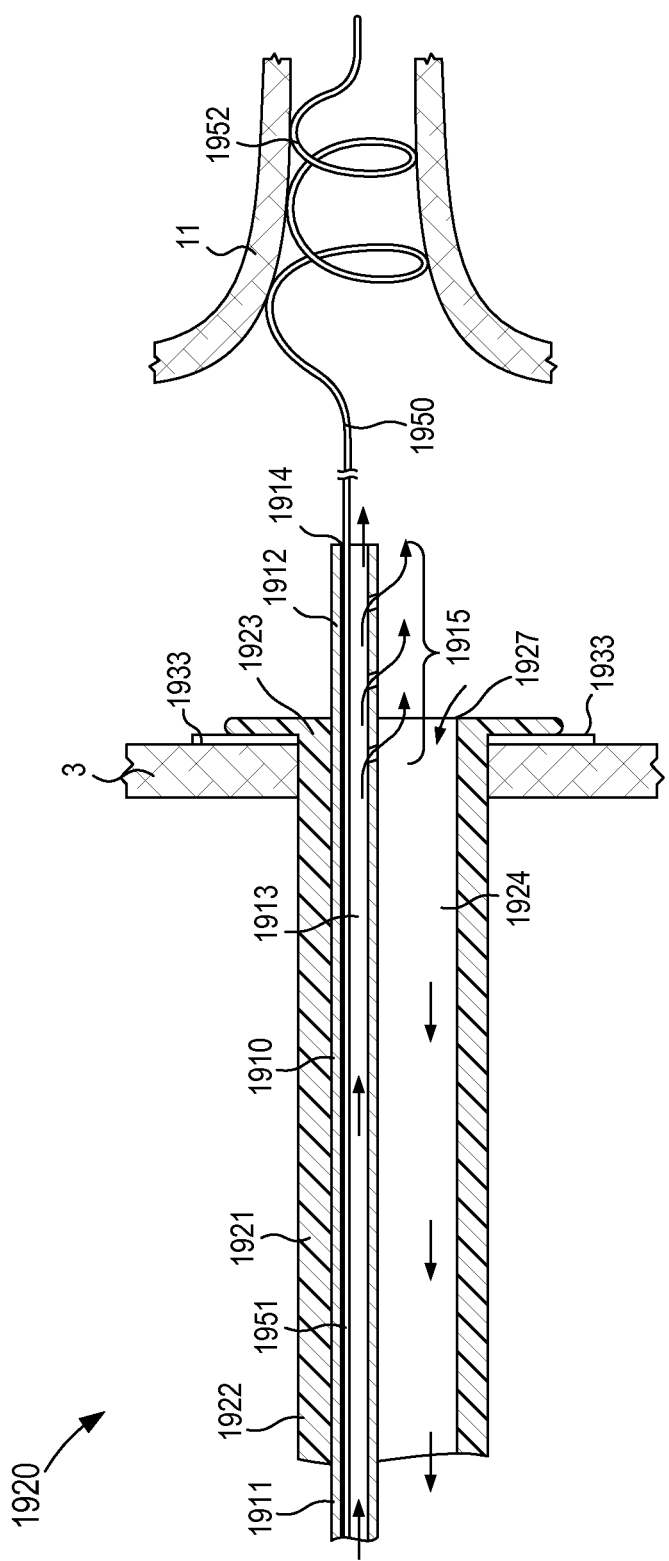

While the embodiments shown and described above include either a recirculation system or a support member, in some embodiments, a cannula assembly can include both a recirculation system and a support member that can be used in concurrently to support a wall of, for example, the left atrium and increase an inlet flow rate into, for example, a pump included in a VAD. For example, FIG. 35 is an illustration of a cannula assembly 1920 coupled to a wall 3 of, for example, the left atrium and a pulmonary vein 11, according to an embodiment. As shown, the cannula assembly 1920 includes a tubular member 1921, a recirculation cannula 1910, and a support member 1950. The tubular member 1921 includes a proximal end portion 1922 and a distal end portion 1923 and defines a lumen 1924 therethrough. The proximal end portion 1922 of the tubular member 1921 can be physically and fluidically coupled to an inlet port of a pump included in a VAD such as those described above. The distal end portion 1923 is configured to be coupled to the wall 3 and can define an opening 1927 that can place an inner volume of the left atrium in fluid communication with the lumen 1924. Moreover, the distal end portion 1923 can include a fabric 1933 that can be placed in contact a surface of the wall 3 to, for example, encourage tissue ingrowth about the fabric. The lumen 1924 defined by the tubular member 1921 is in fluid communication with, for example, the left atrium and defines a flow path through which blood can flow from the left atrium to, for example, a pump of an assist device, as described above. In some embodiments, the tubular member 1921 can be substantially similar the tubular member 721 of FIG. 11. Thus, the tubular member 1921 is not described in further detail herein.

As shown in FIG. 35, the recirculation cannula 1910 is at least partially disposed within the lumen 1924 defined by the tubular member 1921. The recirculation cannula 1910 includes a proximal end portion 1911 and a distal end portion 1912, and defines a lumen 1913 therethrough. The proximal end portion 1911 of the recirculation cannula 1910 can be coupled to, for example, a recirculation port of a pump of an assist device such as those described above. The distal end portion 1912 of the recirculation cannula 1910 can be configured to extend through the opening 1927 defined by the distal end portion 1923 of the tubular member 1921. The distal end portion 1912 of the recirculation cannula 1910 defines an opening 1914 at the distal end and a set of openings 1915 arranged along the circumference of the recirculation cannula 1910. The lumen 1913 of the recirculation cannula 1910 is in fluid communication with, for example, the left atrium and defines a flow path through with blood can flow from the pump to the left atrium (i.e., a recirculation flow). In this manner, the recirculation flow can, for example, reduce a negative pressure differential between the pump and the left atrium as well as increase a total volume of inflow into the left atrium that can limit a collapsing of the wall 3 which could lead to an obstruction of the lumen 1924 and/or of any vascular structure in fluid communication with the left atrium, as described in detail above.

The support member 1950 includes a proximal end portion 1951 and a distal end portion 1952. The proximal end portion 1951 of the support member 1950 is disposed within the lumen 1913 defined by the recirculation cannula 1910. The distal end portion 1952 can include a helix and/or the like that can be inserted into, for example, the pulmonary vein 11 to couple the distal end portion 1952 of the support member 1950 thereto. As shown in FIG. 35, the arrangement of the recirculation cannula 1910 and the support member 1950 can be such that at least a portion of the support member 1950 is disposed within an outlet flow path of the recirculation cannula 1910. In this manner, the outlet flow of the recirculation cannula 1910 can wash at least a portion of the support member 1950 which can, for example, reduce the likelihood of clot formation. For example, in some instances, it may be desirable to strut directly from the tubular member 1921 to the pulmonary vein 11 or other part of the heart such that part of the support member 1950 is not in contact with the atrial wall and "floating" inside the atrium. As described above, the portion of the support member 1950 not in contact with the wall 3 can lead to clot formation. Thus, washing the portion of the support member 1950 with the outlet flow of the recirculation cannula 1910 can substantially reduce and/or prevent clot formation along the portion of the support member 1950 not in contact with the wall 3.

In some embodiments, the distal end portion 1912 of the recirculation cannula 1910 can be placed in any suitable position within the heart to, for example, increase flow through the heart as well as washing any structure (e.g., biologic and/or mechanical) that can lead to clot formation. In this case clot may tend to form on the strut. In some embodiments, any portion of the tubular member 1921, the recirculation member 1910 and/or the support member 1950 can include a coating or the like that can promote tissue ingrowth and/or the like that can reduce the likelihood of clot formation.

Figure 36:
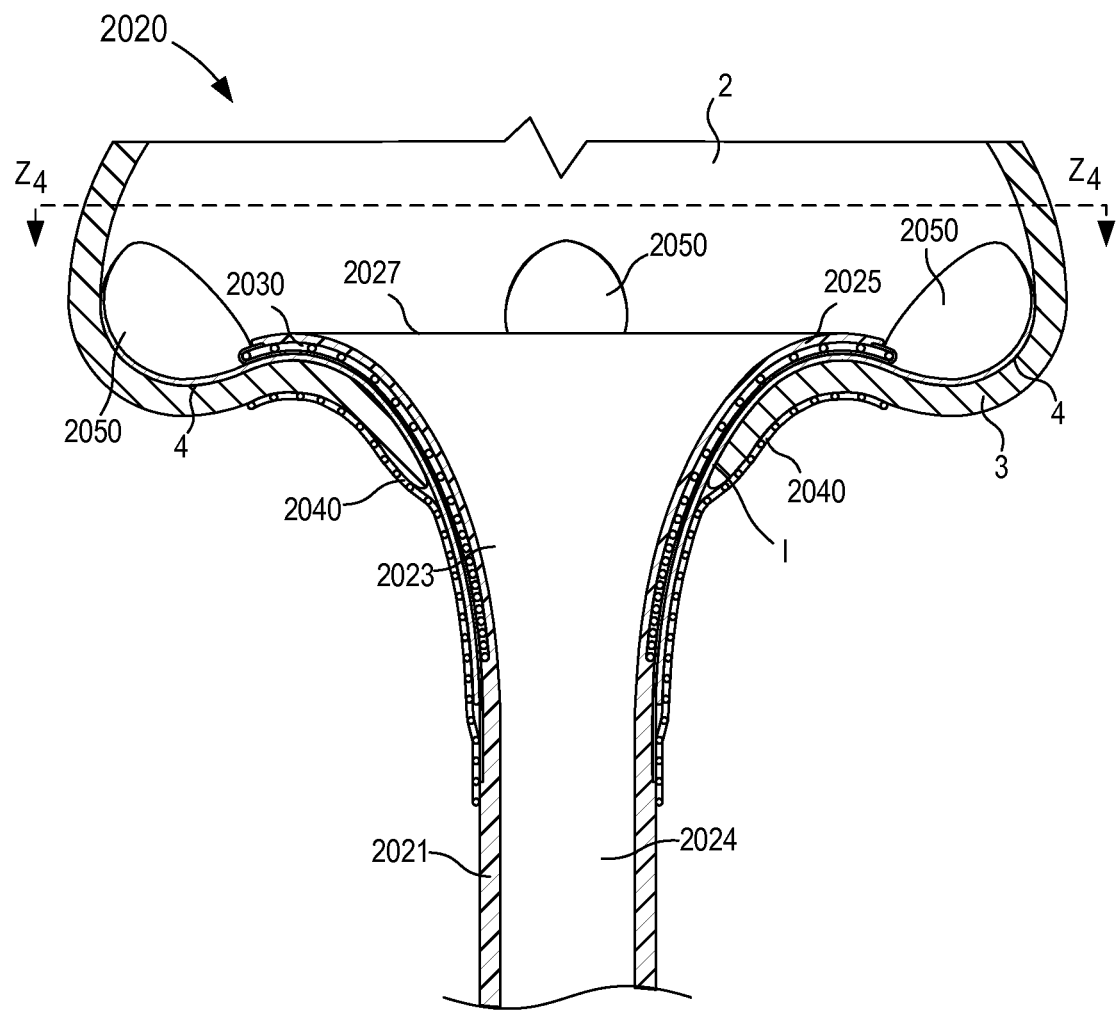
FIG. 36 is a cross-sectional illustration of a portion of an inlet flow cannula assembly according to an embodiment.
Figure 37:
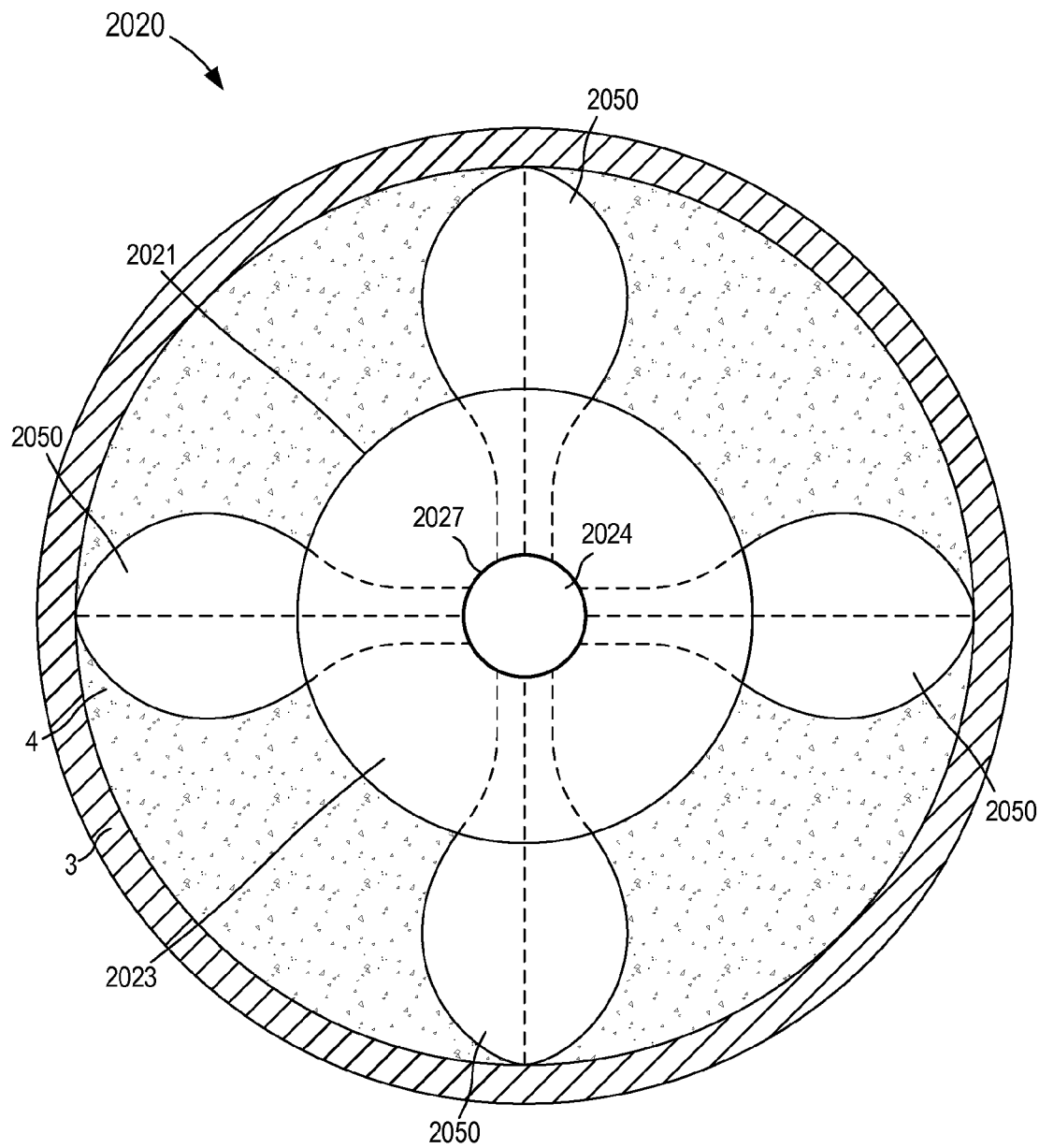
FIG. 37 is a cross-sectional illustration of a portion of the inlet flow cannula assembly taken along the line $Z_4$-$Z_4$ in FIG. 36, coupled to a wall of an atrium of a heart.

Although the support members 1550, 1650, 1750, 1850, and 1950 are shown and described above as being formed from a wire that is configured to support the wall 3 of the left atrium 2, in other embodiments, a cannula assembly can include a support member in a suitable configuration. For example, FIGS. 36 and 37 illustrate an inlet flow cannula assembly 2020 coupled to the wall 3 of the left atrium 2 of the heart according to an embodiment. The inlet flow cannula assembly 2020 (also referred to herein as "cannula assembly") can be included in any of the VADs described herein. As such, the cannula assembly 2020 can be placed in contact with the wall 3 to place the left atrium 2 in fluid communication with, for example, a pump included in the device, as described in further detail herein.

The cannula assembly 2020 includes a tubular member 2021 and a set of support members 2050. The tubular member 2021 includes a proximal end portion (not shown in FIGS. 36 and 37) and a distal end portion 2023, and defines a lumen 2024 therethrough. The proximal end portion can be physically and fluidically coupled to an inlet port and/or the like of a pump included in a VAD. As described in further detail herein, the distal end portion 2023 of the tubular member 2021 defines an opening 2027 such that when the distal end portion 2023 is coupled to the wall 3 of the left atrium 2, the opening 2027 places the lumen 2024 in fluid communication with an inner volume (e.g., a chamber) of the left atrium 2. In some embodiments, portions of the tubular member 2021 can be substantially similar to portions of the tubular member 1521 described in detail above with reference to FIGS. 29-31. Thus, some aspects of the tubular member 2021 are not described herein and should be considered substantially similar in form and/or function to corresponding aspects of the tubular member 1521.

While the cannula assembly 2020 is shown in FIGS. 36 and 37 as being coupled to the wall 3, the cannula assembly 2020 can be positioned relative to the wall 3 and transitioned through a set of configurations in a similar manner as described in detail above with reference to the cannula assembly 1420 of FIGS. 21-28. For example, as shown in FIGS. 36 and 37, the tubular member 2021 includes and/or is otherwise coupled to an inner retention member 2030 and an outer retention member 2040 that can collectively exert a compression force on the wall 3 to couple the distal end portion 2023 of the tubular member 2021 to the wall 3 of the left atrium 2, as described in detail above with reference to the retention members 1530 and 1540, respectively, of FIG. 30. Thus, the inner retention member 2030 and the outer retention member 2040 can be retained in continuous contact with the wall 3, thereby reducing the likelihood of clot formation. Furthermore, the retention members 2030 and 2040 can aid in preventing the entry of fluid leak/air entry, and can ensure that the margin (e.g., an outer edge) of the distal end portion 2023 of the tubular member 2021 is securely pressed against the atrial wall 3. Moreover, the inner retention member 2030 can include a fabric and/or other cover or coating that can encourage healing into the heart tissue, as described in detail above with reference to the fabric 1533 of FIG. 30. In some embodiments, a step or discontinuity between the inner retention member 2030 and the margin of the distal end portion 2023 of the tubular member 2021 which can define a boundary and/or the like that can substantially limit the ingrowth of tissue about the tubular member 2021 such that an inner portion 2025 remains substantially free from tissue ingrowth, as described above.

In some instances, prior to the distal end portion 2023 of the tubular member 2021 being coupled to the wall 3, the support member 2050 can be moved from a first configuration (e.g., a collapsed configuration) to a second configuration (e.g., an expanded configuration). For example, in some embodiments, the cannula assembly 2020 can be moved along a guide wire (not shown in FIGS. 36 and 37) to be inserted into an incision I made in the wall 3 of the left atrium 2, as described above with reference to the tubular member 1421 of FIGS. 21-28. In such embodiments, the distal end portion 2023 of the tubular member 2021 can be maintained in a first configuration (e.g., a collapsed configuration), as described above. Once a desired portion of the cannula assembly 2020 is inserted through the incision I in the atrial wall 3, the tubular member 2021 can be transitioned from its first configuration to its second configuration (e.g., an expanded or open configuration), as shown in FIGS. 36 and 37. In some embodiments, the transition of the distal end portion 2023 of the tubular member 2021 from its first configuration to its second configuration can, for example, urge the support members 2050 to transition from a first configuration to a second configuration, as described in further detail herein.

The support members 2050 of the cannula assembly 2020 can be coupled to and/or otherwise included in the distal end portion 2023 of the tubular member 2021. For example, the support members 2050 can be disposed between the inner retention member 2030 and the inner surface 4 of the wall 3, as shown in FIG. 36. In other embodiments, a cannula assembly can include a set of support members that can, for example, extend through a surface defining the perimeter of a tubular member. For example, in some embodiments, the retention member 2030 can be in contact with the inner surface 4 of the wall 3 and each support member 2050 can be disposed between the retention member 2030 and the inner portion 2025 of the tubular member 2021. More specifically, in some embodiments, the support members 2050 can extend from or through the step or discontinuity defined by the retention member 2030 and the tubular member 2021, as described above. Although not shown in FIGS. 36 and 37, in some embodiments, a portion of the fabric disposed about the inner retention member 2030 can include a surface that is substantially non-linear (e.g., a wave or zig-zag pattern) to allow, for example, the support members 2050 to pass through an inset and/or opening of the surface of the fabric.

The support members 2050 can be any suitable shape, size, or configuration. For example, as shown in FIGS. 36 and 37, the support members 2050 can form lobes or petals that extend from the distal end portion 2023 of the tubular member 2021 to be placed in continuous contact with the inner surface 4 of the wall 3. The support member 2050 can be formed from any suitable material such as, for example, metal (e.g., Nitinol®, stainless steel, etc.), biocompatible polymer (e.g., those described above), and/or the like. In some embodiments, the support members 2050 can include a covering or the like that can improve strength or biocompatibility such as, for example, polyester (e.g., Dacron®), Teflon®, Gore-Tex®, PTFE, and/or the like. In other embodiments, the support members 2050 can include a covering or the like that can be, for example, a fabric or the like that can facilitate tissue ingrowth and/or the like. In some embodiments, an outer surface of the support members 2050 can be roughened or textured to encourage tissue coverage. The support members 2050 can be configured to, for example, increase a surface area of the cannula assembly 2020 in contact with an inner surface 4 of the wall 3 such that movement of the wall 3 relative to the tubular member 2021 is limited, as described in further detail herein.

As described above, the support members 2050 can be configured to transition between their first configuration and their second configuration. For example, in some embodiments, the support members 2050 can be substantially collapsed or folded when in their first configuration. In some embodiments, the support members 2050 can be retained in their first configuration while the distal end portion 2023 of the tubular member 2021 is retained in its first configuration. For example, in some embodiments, the cannula assembly 2020 can include a cap or sheath (not shown in FIGS. 36 and 37) that can maintain the distal end portion 2023 of the tubular member 2021 and the support members 2050 in the first configuration. Thus, when the cap or sheath is removed, the distal end portion 2023 can transition towards its second configuration, which in turn, can urge the support members 2050 to transition towards their second configuration.

As shown in FIGS. 36 and 37, with the distal end portion 2023 of the tubular member 2021 and the support members 2050 in the second configuration, the cannula assembly 2020 can be coupled to the wall 3 in a similar manner as described above with reference to the cannula assembly 1420 and/or the cannula assembly 1520 described above. The arrangement of the support members 2050 can be such that a desired amount of force is exerted by support members 2050 on the inner surface 4 of the wall 3 of the left atrium 2 that is sufficient to limit movement of the wall 3 relative to the tubular member 2021. For example, the support members 2050 can have a stiffness that can be sufficiently small to allow the support members 2050 to transition between the first configuration (not shown) and the second configuration (see e.g., FIGS. 36 and 37) while being sufficiently large to limit movement of the wall 3. As such, in some embodiments, the support members 2050 can, for example, have a thickness and/or size that is associated with the desired stiffness. In other embodiments, the support members 2050 can be formed from one or more materials that can have a modulus of elasticity that can be associated with the desired stiffness.

As shown in FIG. 36 and as described above, the support members 2050 engage the inner surface 4 such that the inner retention member 2030 and/or an outer edge of the tubular member 2021 is not pried away from the inner surface 4. In other words, a force exerted by each of the support members 2050 on the inner surface 4 can be relatively uniform such that the each of the support members 2050 do not act as a lever that would otherwise result in a force exerted on the inner retention member 2030 that would resist the force exerted by the inner retention member 2030. Thus, the likelihood of clot formation, the formation of dead spots in a flow of fluid within the left atrium, and/or the formation of eddy currents in a flow of fluid within the left atrium can be reduced or substantially prevented. In other embodiments, the force exerted by the support members 2050 can be asymmetrical (e.g., non-uniform) such that target areas of the wall 3 are exposed to a larger force than other areas of the wall 3. Although not shown in FIGS. 36 and 37, in some embodiments, the support members 2050 can include one or more anchors and/or the like that retain the support members 2050 in continuous contact with the inner surface 4, thereby reducing the likelihood of clot formation along the support members 2050.

In some embodiments, the overall size of the support members 2050 can be based at least in part on a size of the left atrium 2 (as determined via an imaging technique or the like) such that the support members 2050. In some embodiments, a diameter defined by a collective circumferential size of the support members 2050 can be, for example, about three times a diameter associated with the perimeter of the distal end portion 2023 of the tubular member 2021. Thus, the surface area of the cannula assembly 2020 that is in contact with the inner surface 4 of the wall 3 is increased and the support members 2050 can exert the desired amount of force on the inner surface 4 to limit movement of the wall 3 relative to the tubular member 2021. In other words, the support members 2050 can support at least a portion of the wall 3 to limit and/or prevent deformation of the wall 3 that can otherwise result in a suction event (e.g., an obstruction of the opening 2027 and thus, the lumen 2024) and/or a kinking or obstruction of peripheral vascular structure such as, for example, the pulmonary vein or the like. Moreover, the support members 2050 can engage the inner surface 4 in such a way that the inner retention members 2030 and/or an outer edge of the tubular member 2021 is not pried away from the inner surface 4. Thus, the likelihood of clot formation, the formation of dead spots in a flow of fluid within the left atrium, and/or the formation of eddy currents in a flow of fluid within the left atrium can be reduced or substantially prevented.

Figure 38:
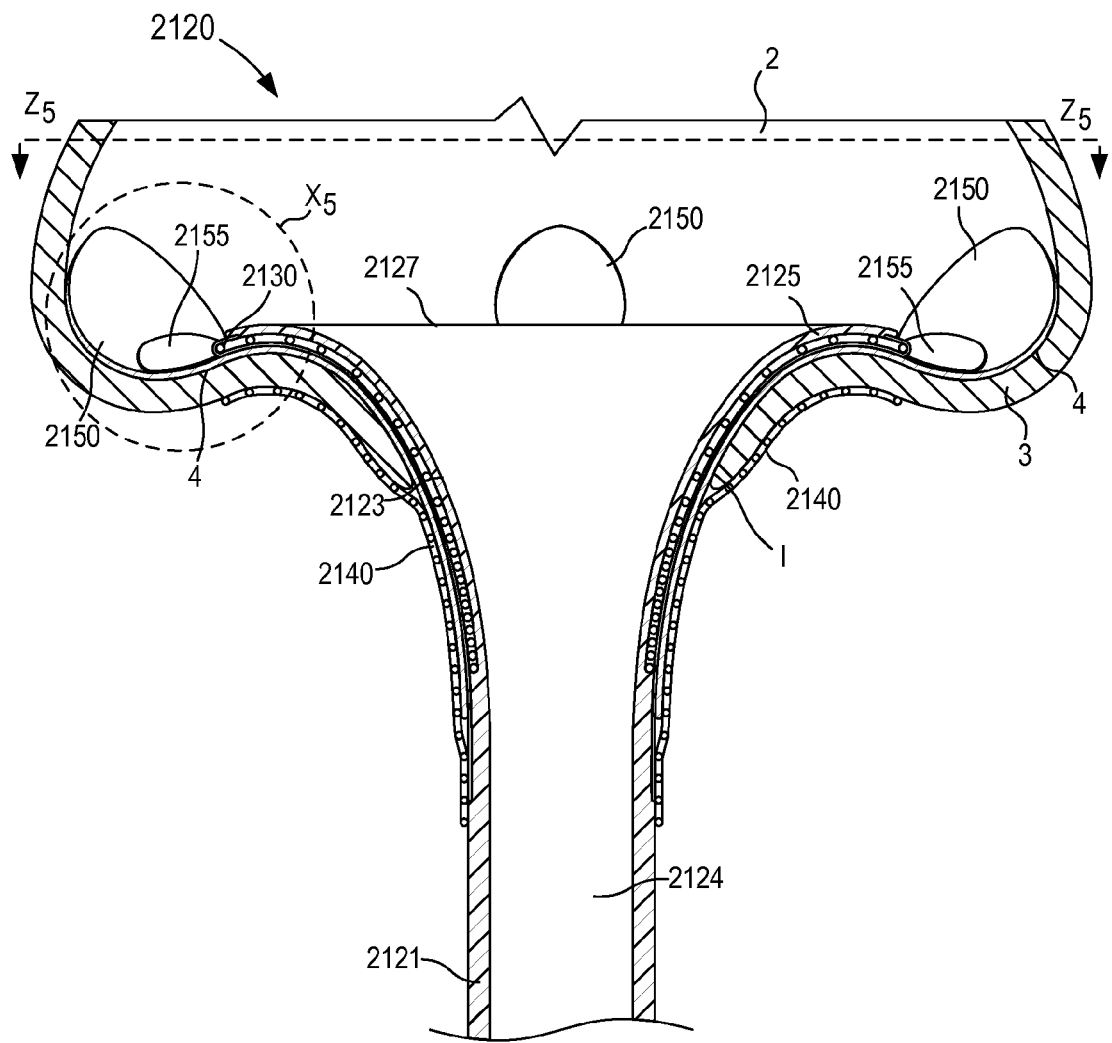
FIG. 38 is a cross-sectional illustration of a portion of an inlet flow cannula assembly according to an embodiment.
Figure 39:
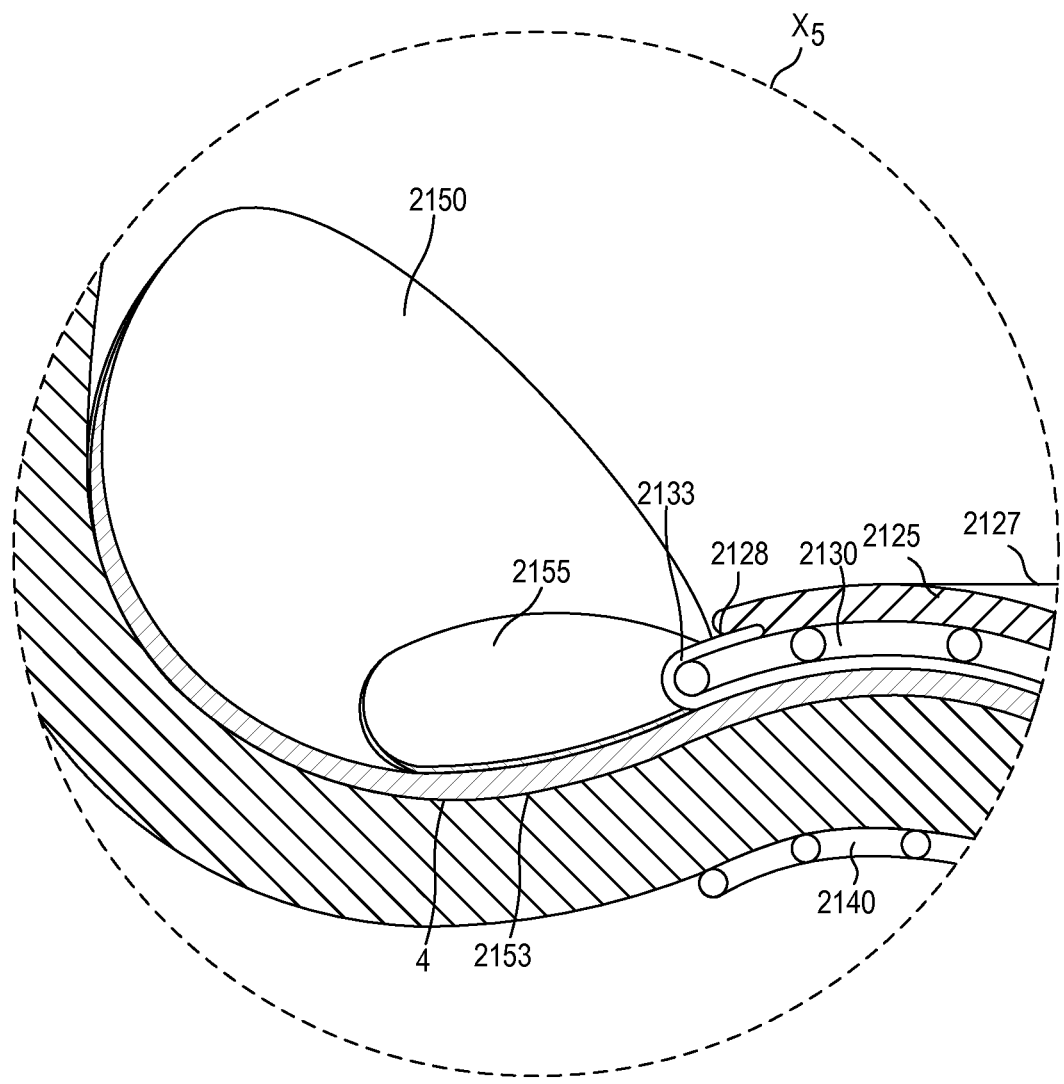
FIG. 39 is an enlarged view of a portion of the inlet flow cannula assembly of FIG. 38 identified by the region $X_5$.
Figure 40:
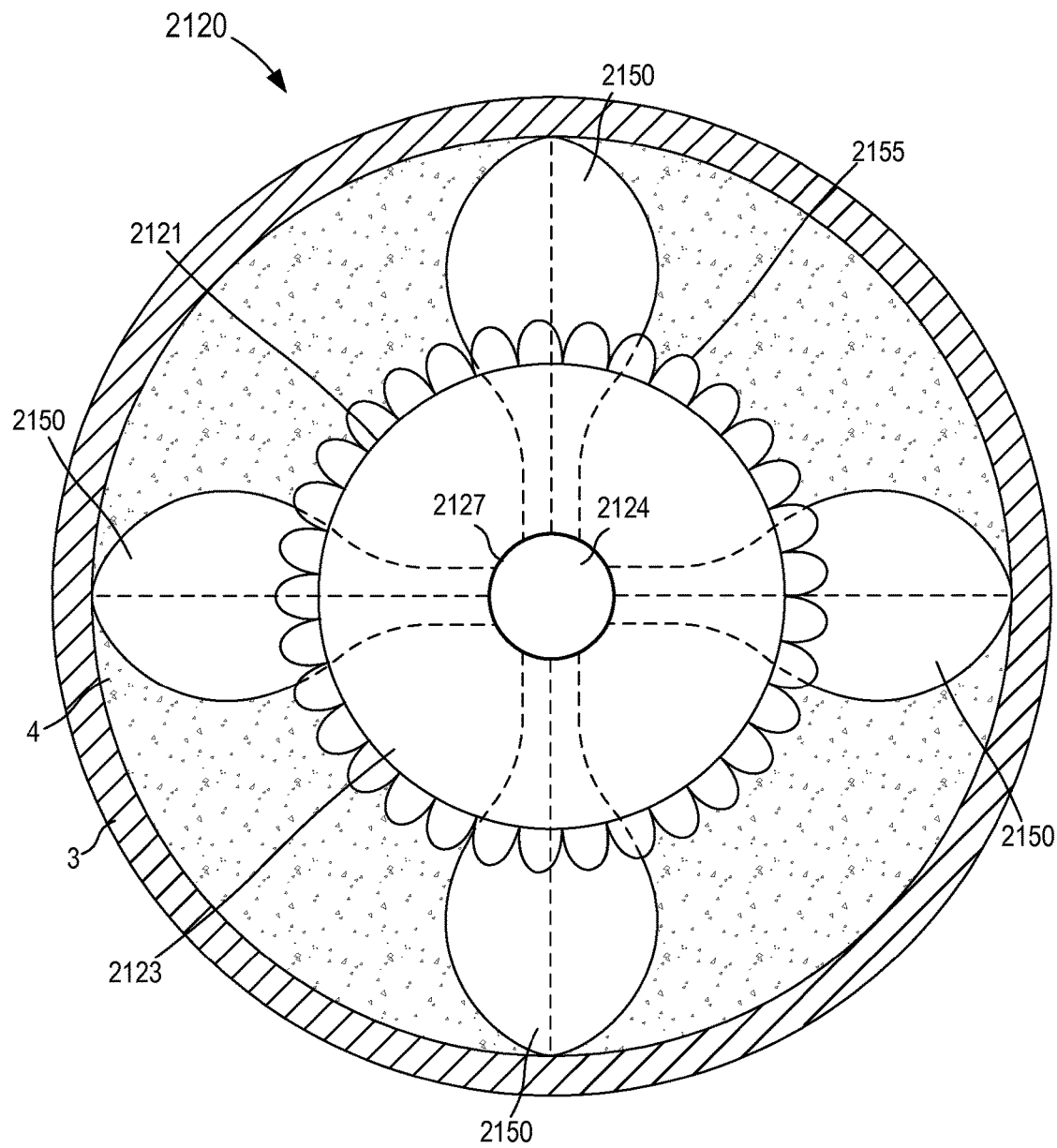
FIG. 40 is a cross-sectional illustration of a portion of the inlet flow cannula assembly taken along the line $Z_5$-$Z_5$ in FIG. 38, coupled to a wall of an atrium of a heart.

While the support members 2050 included in the cannula assembly 2020 are shown as having a substantially uniform size, in other embodiments, a cannula assembly can include one or more support members of different sizes. In some embodiments, a cannula assembly can include two sets of support members with a first set of support members having a first size and a second set of support members having a second size. For example, FIGS. 38-40 illustrate an inlet flow cannula assembly 2120 coupled to the wall 3 of the left atrium 2 of the heart according to an embodiment. The inlet flow cannula assembly 2120 (also referred to herein as "cannula assembly") can be included in any of the VADs described herein. As such, the cannula assembly 2120 can be placed in contact with the wall 3 to place the left atrium 2 in fluid communication with, for example, a pump included in the device, as described in further detail herein.

The cannula assembly 2120 includes a tubular member 2121, a first set of support members 2150, and a second set of support members 2155. The tubular member 2121 includes a proximal end portion (not shown in FIGS. 38-40) and a distal end portion 2123, and defines a lumen 2124 therethrough. The proximal end portion can be physically and fluidically coupled to an inlet port and/or the like of a pump included in a VAD. As described in further detail herein, the distal end portion 2123 of the tubular member 2121 defines an opening 2127 such that when the distal end portion 2123 is coupled to the wall 3 of the left atrium 2, the opening 2127 places the lumen 2124 in fluid communication with an inner volume (e.g., a chamber) of the left atrium 2. In some embodiments, portions of the tubular member 2121 can be substantially similar to portions of the tubular member 1521 described in detail above with reference to FIGS. 29-31. Thus, some aspects of the tubular member 2121 are not described herein and should be considered substantially similar in form and/or function to corresponding aspects of the tubular member 1521.

While the cannula assembly 2120 is shown in FIGS. 38 and 39 as being coupled to the wall 3, the cannula assembly 2120 can be positioned relative to the wall 3 and transitioned through a set of configurations in a similar manner as described in detail above with reference to the cannula assembly 1420 of FIGS. 21-28. For example, as shown in FIGS. 38 and 39, the tubular member 2121 includes and/or is otherwise coupled to an inner retention member 2130 and an outer retention member 2140 that can collectively exert a compression force on the wall 3 to couple the distal end portion 2123 of the tubular member 2121 to the wall 3 of the left atrium 2, as described in detail above with reference to the retention members 1530 and 1540, respectively, of FIG. 30. Thus, the inner retention member 2130 and the outer retention member 2140 can be retained in continuous contact with the wall 3, thereby reducing the likelihood of clot formation. Furthermore, the retention members 2130 and 2140 can aid in preventing the entry of fluid leak/air entry, and can ensure that the margin (e.g., an outer edge) of the distal end portion 2123 of the tubular member 2121 is securely pressed against the atrial wall 3. Moreover, the inner retention member 2130 can include a fabric 2133 and/or other cover or coating that can encourage healing into the heart tissue, as described in detail above with reference to the fabric 1533 of FIG. 30. In some embodiments, a step 2128 or discontinuity between the inner retention member 2130 and the margin of the distal end portion 2123 of the tubular member 2121 which can define a boundary and/or the like that can substantially limit the ingrowth of tissue about the tubular member 2121 such that an inner portion 2125 remains substantially free from tissue ingrowth, as described above.

Although not shown in FIGS. 38-40, in some instances, the cannula assembly 2120 can be moved along a guide wire (not shown in FIGS. 38-40) to be inserted into an incision I made in the wall 3 of the left atrium 2, as described above with reference to the tubular member 1421 of FIGS. 21-28. In such embodiments, the distal end portion 2123 of the tubular member 2121 can be maintained in a first configuration (e.g., a collapsed configuration) and once a desired portion of the cannula assembly 2120 is inserted through the incision I in the atrial wall 3, the tubular member 2121 can be transitioned from its first configuration to its second configuration (e.g., an expanded or open configuration), as shown in FIGS. 38-40. In some embodiments, the transition of the distal end portion 2123 of the tubular member 2121 from its first configuration to its second configuration can, for example, urge the first set of support members 2150 and or the second set of support members 2155 to transition from their first configuration to their second configuration, as described in further detail herein.

The first set of support members 2150 and the second set of support members 2155 of the cannula assembly 2120 can be coupled to and/or otherwise included in the distal end portion 2123 of the tubular member 2121. The first set of support members 2150 and the second set of support members 2155 can be any suitable shape, size, or configuration. For example, as shown in FIGS. 38-40, the support members 2150 and 2155 can form lobes or petals that extend from the distal end portion 2123 of the tubular member 2121. More particularly, each support member 2150 included in the first set of support members 2150 can have a first size and each member 2155 included in the second set of support members 2155 can have a second size, smaller than the first size, as shown in FIG. 39. As described in further detail herein, the first set of support members 2150 can include an outer surface 2153 that is configured to be placed in substantially continuous contact with the inner surface 4 of the wall 3 to limit movement of the wall 3 relative to the tubular member 2121 and the second set of support members 2155 can be placed in contact with a portion of the first set of support members 2150 and/or the inner surface 4 of the wall 3 to limit, for example, an undesirable force at or near the perimeter of the distal end portion 2123 of the tubular member 2121.

The support members 2150 and 2155 can be formed from any suitable material such as, for example, metal (e.g., Nitinol®, stainless steel, etc.), biocompatible polymer (e.g., those described above), and/or the like. In some embodiments, the support members 2150 and 2155 can include a covering or the like that can improve strength or biocompatibility such as, for example, polyester (e.g., Dacron®), Teflon®, Gore-Tex®, PTFE, and/or the like. In other embodiments, the support members 2150 and 2155 can include a covering or the like that can be, for example, substantially similar to the fabric 2133 or the like that can facilitate tissue ingrowth and/or the like. In some embodiments, an outer surface of the support members 2150 and 2155 can be roughened or textured to encourage tissue coverage.

The support members 2150 and 2155 can be disposed between the inner retention member 2130 and the inner surface 4 of the wall 3, as shown in FIGS. 38 and 39. In other embodiments, a cannula assembly can include one or more sets of support members that can, for example, extend through a surface defining the perimeter of a tubular member. For example, in some embodiments, the retention member 2130 can be in contact with the inner surface 4 of the wall 3 and the first set of support members 2150 and/or the second set of support members 2155 can be disposed between the retention member 2130 and the inner portion 2125 of the tubular member 2121. More specifically, in some embodiments, the first set of support members 2150 and/or the second set of support members 2155 can extend from or through the step 2128 or discontinuity defined by the retention member 2130 and the tubular member 2121, as described above.

While the cannula assembly 2120 is shown in FIG. 39 as including the first set of support members 2150 and the second set of support members 2155 in a substantially stacked configuration, in other embodiments, the first set of support members 2150 and the second set of support members 2155 can be disposed in any suitable arrangement or orientation relative to one another. For example, in some embodiments, the second set of support members 2155 can be in a stacked configuration with the first set of support member 2150 with, for example, a layer of fabric 2133 disposed therebetween. In other embodiments, the support member 2150 and the second support member can be in a non-stacked configuration. For example, in some embodiments, each support member included in the second set of support members 2155 can be at least partially disposed between the inner surface 2125 of the tubular member 2121 and the inner retention member 2130. In such embodiments, each support member in the second set of support members 2155 can extend from the perimeter of the tubular member 1521 in a substantially curvilinear path towards the inner surface 4 of the wall 3.

As described above, the first set of support members 2150 and the second set of support members 2155 can be configured to transition between their first configuration and their second configuration. For example, in some embodiments, the support members 2150 and 2155 can be substantially collapsed or folded when in their first configuration. In some embodiments, the support members 2150 and 2155 can be retained in their first configuration while the distal end portion 2123 of the tubular member 2121 is retained in its first configuration and when the distal end portion 2123 is transitioned towards its second configuration the first set of support members 2150 and/or the second set of support members 2155 can be transitioned towards their second configuration.

With the distal end portion 2123 of the tubular member 2121 and the support members 2150 and 2155 in the second configuration, the cannula assembly 2120 can be coupled to the wall 3 in a similar manner as described above with reference to the cannula assembly 1420 and/or the cannula assembly 1520 described above. The arrangement of the first set of support members 2150 can be such that a desired amount of force is exerted by each support member 2150 included in the first set of support members 2150 on the inner surface 4 of the wall 3 of the left atrium 2 that is sufficient to limit movement of the wall 3 relative to the tubular member 2121, as described above.

As shown in FIG. 39, the first set of support members 2150 can engage the inner surface 4 such that the inner retention member 2130 and/or an outer edge of the tubular member 2121 is not pried away from the inner surface 4. In some embodiments, the second set of support members 2155 can engage a portion of the first set of support members 2150 to, for example, exert a force that can be configured to resist a force exerted by the first set of support members 2150 to pry the inner retention member 2130 and/or an outer edge of the tubular member 2121 from the inner surface 4. Thus, the likelihood of clot formation, the formation of dead spots in a flow of fluid within the left atrium, and/or the formation of eddy currents in a flow of fluid within the left atrium can be reduced or substantially prevented. Although not shown in FIGS. 38-40, in some embodiments, any of the support members 2150 included in the first set of support members 2150 and/or any of the support members 2155 included in the second set of support members 2155 can include one or more anchors and/or the like that retain the support members 2150 and/or 2155, respectively, in continuous contact with the inner surface 4 and/or the support members included in the other set of support members, thereby reducing the likelihood of clot formation along the support members 2150.

In this manner, the first set of support members 2150 and the second set of support members 2155 can support at least a portion of the wall 3 to limit and/or prevent deformation of the wall 3 that can otherwise result in a suction event (e.g., an obstruction of the opening 2127 and thus, the lumen 2124) and/or a kinking or obstruction of peripheral vascular structure such as, for example, the pulmonary vein or the like. Moreover, the support members 2150 can engage the inner surface 4 in such a way that the inner retention members 2130 and/or an outer edge of the tubular member 2121 is not pried away from the inner surface 4. Thus, the likelihood of clot formation, the formation of dead spots in a flow of fluid within the left atrium, and/or the formation of eddy currents in a flow of fluid within the left atrium can be reduced or substantially prevented.

Figure 41:
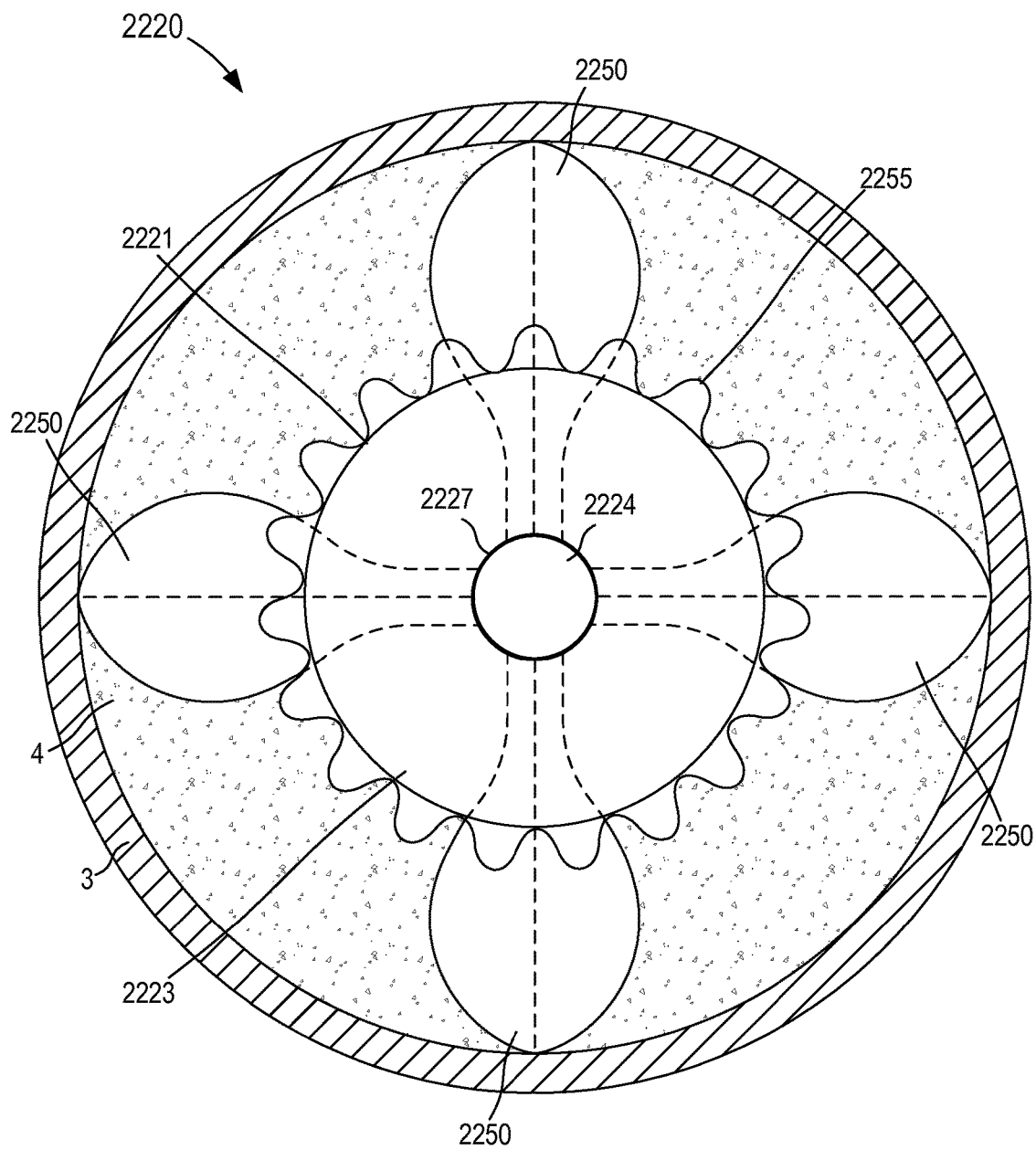
FIG. 41 is a top view of a portion of an inlet flow cannula assembly coupled to a wall of an atrium of a heart, according to an embodiment.

In some embodiments, each support member 2155 included in the second set of support members 2155 can be distinct, as shown in FIG. 40. In other embodiments, a cannula assembly can include a second set of support members that are linked and/or continuous. For example, FIG. 41 is an illustration of a cannula assembly 2220 coupled to a wall 3 of, for example, a left atrium of a heart, according to an embodiment. The cannula assembly 2220 includes a tubular member 2221, a first set of support members 2250, and a second set of support members 2255. The tubular member 2221 includes a distal end portion 2223 that can be placed in contact with an inner surface 4 of the wall 3 to couple the cannula assembly 2220 to the wall 3. Moreover, the distal end portion 2223 of the tubular member 2221 defines an opening 2227 that is configured to place a lumen 2224 defined by the tubular member 2221 in fluid communication with an inner volume of, for example, a left atrium. In some embodiments, the tubular member 2221 can be substantially similar to the tubular member 1521 described above with reference to FIGS. 29-31. Thus, aspects of the tubular member 2221 are not described in further detail herein.

The first set of support members 2250 and the second set of support members 2255 can be substantially similar in form and function to the first set of support members 2150 and the second set of support members 2155 described above with reference to FIGS. 38-40. Therefore, aspects of the first set of support members 2250 and the second set of support members 2255 are not described in further detail herein. The second set of support members 2255 can differ from the second set of support members 2155, however, in that the second set of support members 2255 includes support members that are linked or otherwise continuous. In this manner, the second set of support members 2255 can include a set of bends and/or folds that can, for example, allow the second set of support members 2255 to be continuous and/or that can reduce stress concentration risers that can introduce, for example, failure points and/or points at which the second set of support members 2255 can deform.

In this manner, the first set of support members 2250 and the second set of support members 2255 can support at least a portion of the wall 3 to limit and/or prevent deformation of the wall 3 that can otherwise result in a suction event (e.g., an obstruction of the opening 2227 and thus, the lumen 2224) and/or a kinking or obstruction of peripheral vascular structure such as, for example, the pulmonary vein or the like. In some embodiments, the second set of support members 2255 can engage a portion of the first set of support members 2250 to, for example, exert a force that can be configured to resist a force exerted by the first set of support members 2250 that can otherwise pry the inner retention member 2230 and/or an outer edge of the tubular member 2221 from the inner surface 4. Thus, the likelihood of clot formation, the formation of dead spots in a flow of fluid within the left atrium, and/or the formation of eddy currents in a flow of fluid within the left atrium can be reduced or substantially prevented.

Figure 42:
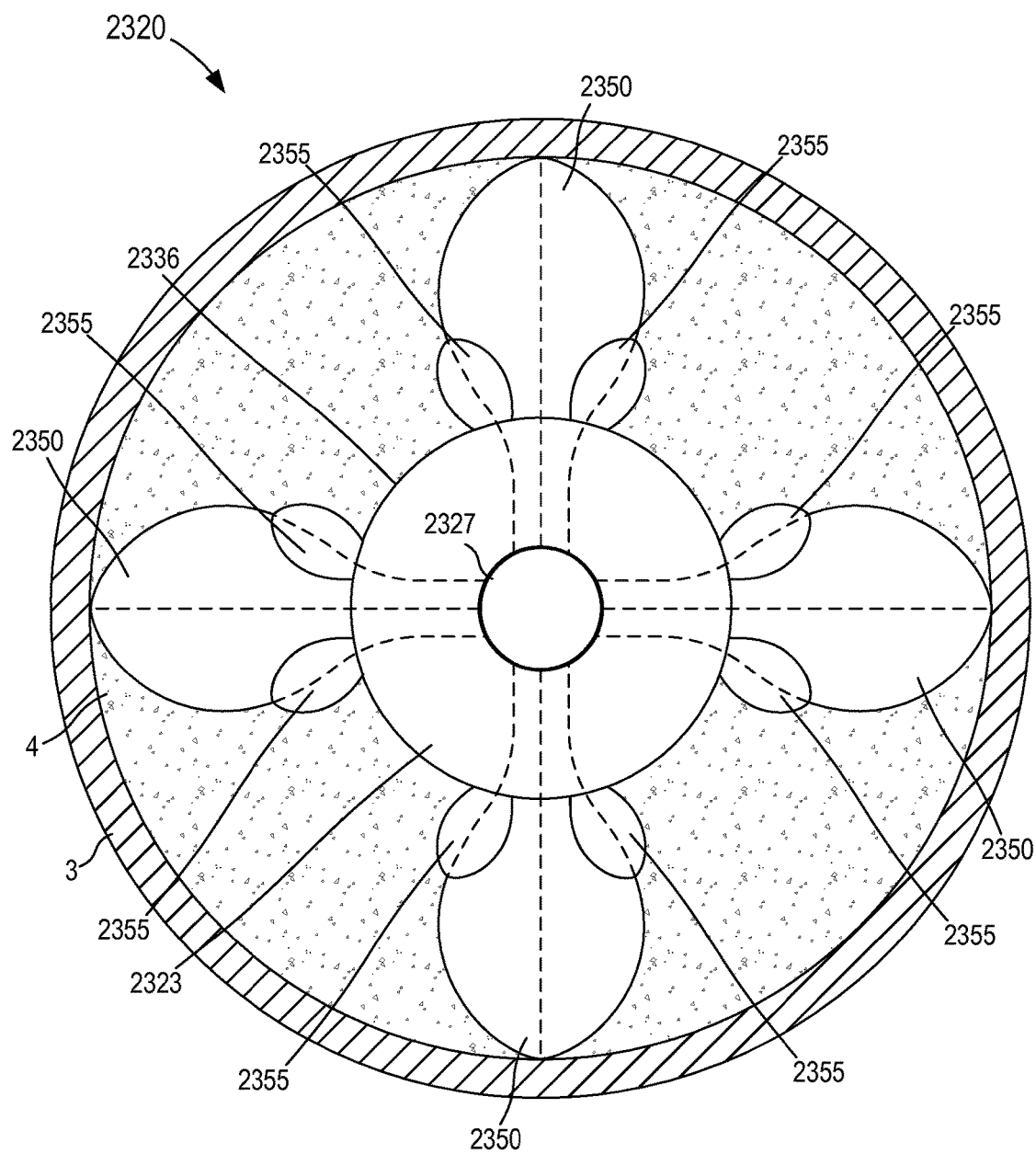
FIG. 42 is a top view of a portion of an inlet flow cannula assembly coupled to a wall of an atrium of a heart, according to an embodiment.

Although the second set of support members 2155 of the cannula assembly 2120 and the second set of support members 2255 of the cannula assembly 2220 are shown as substantially circumscribing the tubular members 2121 and 2221, respectively, in other embodiments, a cannula assembly can include a first set of support members and a second set of support members that are disposed at distinct positions along a perimeter of a tubular member. For example, FIG. 42 is an illustration of a cannula assembly 2320 coupled to a wall 3 of, for example, a left atrium, according to an embodiment. The cannula assembly 2320 includes a tubular member 2321, a first set of support members 2350, and a second set of support members 2355. The tubular member 2321 includes a distal end portion 2323 that can be placed in contact with an inner surface 4 of the wall 3 to couple the cannula assembly 2320 to the wall 3. Moreover, the distal end portion 2323 of the tubular member 2321 defines an opening 2327 that is configured to place a lumen 2324 defined by the tubular member 2321 in fluid communication with an inner volume of, for example, a left atrium. In some embodiments, the tubular member 2321 can be substantially similar to the tubular member 1521 described above with reference to FIGS. 29-31. Thus, aspects of the tubular member 2321 are not described in further detail herein.

The first set of support members 2350 and the second set of support members 2355 can be substantially similar in form and function to the first set of support members 2150 and the second set of support members 2155 described above with reference to FIGS. 38-40. Therefore, aspects of the first set of support members 2350 and the second set of support members 2355 are not described in further detail herein. The second set of support members 2355 can differ from the second set of support members 2155, however, in that each support member 2355 in the second set of support members 2355 is disposed at a distinct position (e.g., a different and unconnected position) along the perimeter of the distal end portion 2323 of the tubular member 2321. For example, as shown in FIG. 42, the second set of support members 2355 can be arranged to include a support member 2355 that substantially covers and/or engages each side portion of each support member 2350 included in the first set of support members 2350 (i.e., two support members 2355 per one support member 2350).

In this manner, the first set of support members 2350 and the second set of support members 2355 can support at least a portion of the wall 3 to limit and/or prevent deformation of the wall 3 that can otherwise result in a suction event (e.g., an obstruction of the opening 2327 and thus, the lumen 2324) and/or a kinking or obstruction of peripheral vascular structure such as, for example, the pulmonary vein or the like. In some embodiments, the second set of support members 2355 can engage a portion of the first set of support members 2350 to, for example, exert a force that can be configured to resist a force exerted by the first set of support members 2350 that can otherwise pry the inner retention member 2330 and/or an outer edge of the tubular member 2321 from the inner surface 4. Thus, the likelihood of clot formation, the formation of dead spots in a flow of fluid within the left atrium, and/or the formation of eddy currents in a flow of fluid within the left atrium can be reduced or substantially prevented.

Figure 43:
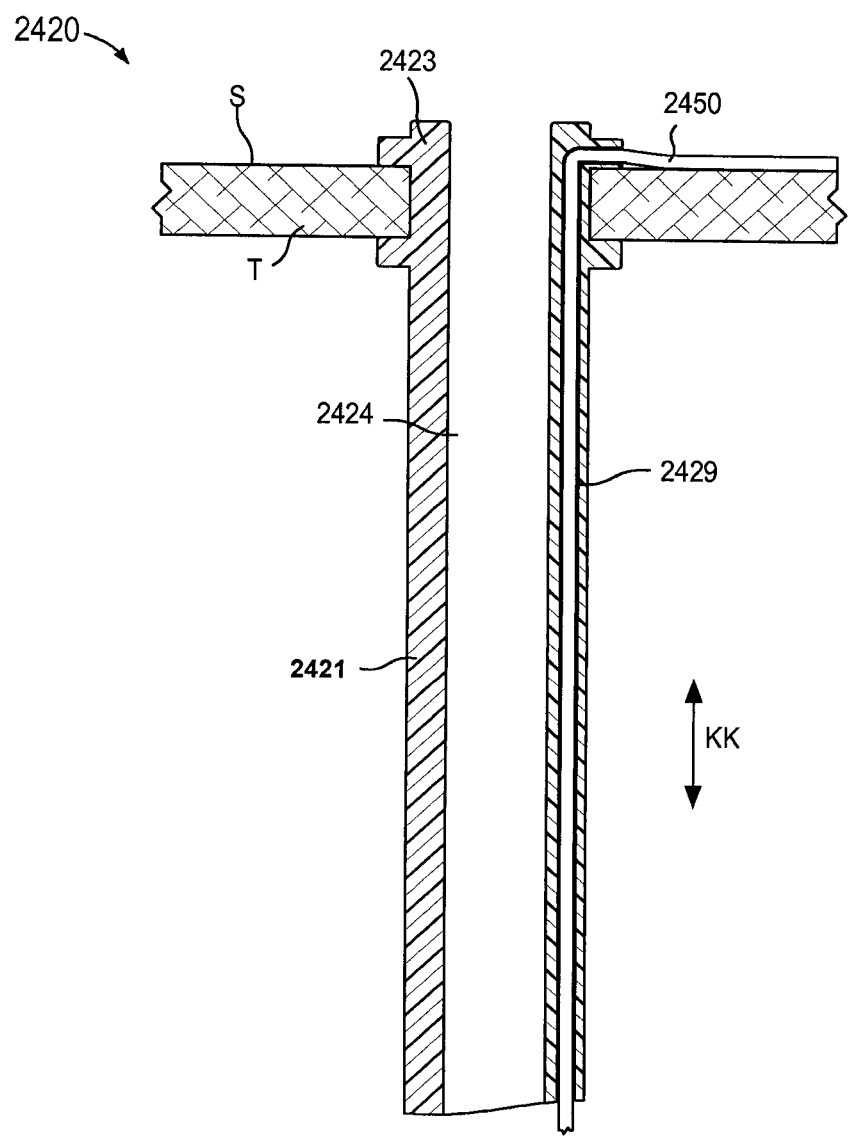
FIG. 43 is a schematic illustration of a portion of an inlet flow cannula assembly according to an embodiment.

FIG. 43 is an illustration of an inlet flow cannula assembly 2420 coupled to a target tissue T according to an embodiment. The target tissue T can be any suitable bodily tissue such as, for example, a wall or other structure of the heart, a wall of a vascular structure, and/or the like. For example, in some instances, the target tissue T can be a wall of a left atrium of a heart. The wall of the left atrium can define at least a portion of an interior volume such that an exterior surface of the wall is fluidically isolated from an interior surface of the wall.

The cannula assembly 2420 includes a tubular member 2421 and a support member 2450. The tubular member 2421 can be, for example, a cannula or catheter that defines a lumen 2424 and a channel 2429. The lumen 2424 extends substantially through a distal surface and a proximal surface of the tubular member 2421 such that, when the cannula assembly 2420 is coupled to the target tissue T, the lumen 2424 is placed in fluid communication with an interior volume (not shown in FIG. 43) defined by the target tissue T (e.g., an interior volume of an organ and/or vascular structure). In some embodiments, the tubular member 2421 can include a distal end portion 2423 (e.g., a connection portion) that is configured to be coupled to the target tissue T. For example, a portion of the target tissue T can be disposed within a recess defined by the distal end portion 2423. In some embodiments, the distal end portion 2423 of the tubular member 2421 can be sutured to the target tissue T to coupled the tubular member 2421 thereto. In some embodiments, the distal end portion 2423 of the tubular member 2421 can be in contact with a first portion of and inner surface S of the target tissue T when coupled thereto.

The channel 2429 is configured to receive the support member 2450 as the support member is moved from a first configuration to a second configuration, as described in further detail herein. The channel 2429 can be, for example, a lumen defined by the tubular member 2421. In some embodiments, the channel 2429 can be in an orthogonal configuration in which a first portion is substantially parallel to a longitudinal centerline (not shown) defined by the tubular member 2421 and a second portion is substantially perpendicular to the longitudinal centerline. In other embodiments, the tubular member 2421 can define the channel 2429 in any suitable orientation and/or configuration. For example, in some embodiments, the tubular member 2421 can define a channel that defines a substantially helical path about the longitudinal centerline of the tubular member 2421. Although the tubular member 2421 is shown in FIG. 43 as defining a single channel 2429, in other embodiments, a tubular member 2421 can include any number of channels that can be in any suitable arrangement.

The support member 2450 can be any suitable shape, size, or configuration. For example, in some embodiments, the support member 2450 can be a wire or the like that can be formed from any suitable material such as, for example, nickel-titanium alloy (Nitinol®), stainless steel, plastic, composite, and/or any other biocompatible material. The support member 2450 can be transitioned between a first configuration (e.g., a collapsed configuration) and a second configuration (e.g., an expanded configuration) to be placed in contact with a second portion of the inner surface S of the target tissue T, thereby limiting movement of the target tissue T relative to the tubular member 2421, as indicated by the arrow KK in FIG. 43. More specifically, the support member 2450 can include an end portion that can be disposed within the channel 2429 when the support member 2450 is in its first configuration (not shown in FIG. 43) and can be advanced through the channel 2429 toward the second configuration to dispose the end portion in the interior volume defined at least in part by the target tissue T. In this manner, the end portion of the support member 2450 can extend away from the tubular member 2450 to be substantially in continuous contact with the inner surface S. When in the second configuration, the end portion of the support member 2450 can be in contact with the second portion of the inner surface S of the target tissue T to limit movement of the target tissue T relative to the tubular member 2421. In some embodiments, the second portion of the inner surface S of the target tissue T can have and/or include a larger surface area than a surface area included in and/or defined by the first portion of the inner surface S. Similarly stated, the support member 2450 can be in substantially continuous contact with the second portion of the inner surface S to, for example, increase a footprint of the cannula assembly 2420 on the inner surface S of the target tissue T. Thus, the support member 2450 can limit movement of the target tissue T relative to the tubular member 2421 that can, for example, reduce the likelihood of a suction event (e.g., a portion of the target tissue T collapsing and obstructing the lumen 2424 or other vascular openings).

By maintaining the support structure 2450 and/or the tubular member 2421 in substantially continuous contact with the surface S, the likelihood of clot formation is reduced, as described in detail above. The arrangement of the support member 2450 and the tubular member 2421 can also reduce eddy currents near the surface S of the target tissue T that would otherwise limit flow of blood to portions of the surface S and thereby increase the risk of clot formation. In addition, any portion of the tubular member 2421 and/or the support member 2450 can include an outer surface and/or surface finish configured to reduce clot formation and/or increase tissue ingrowth. For example, in some embodiments, at least a portion of the tubular member 2421 and/or the support member 2451 can be substantially circumscribed by a fabric and/or outer surface such as Dacron®, polyester, polytetrafluoroethylene (PTFE), silicon, polypropylene, and/or the like. In some embodiments, at least a portion of the tubular member 2421 and/or the support member 2450 can be coated by a biological material such as human tissue cells and/or animal tissue cells. In some embodiments, the outer surface of at least a portion of the tubular member 2421 and/or the support member 2450 can include a rough texture configured to encourage tissue ingrowth. Thus, bodily tissue can form about at least a portion of the tubular member 2421 and/or the support member 2450 which can reduce the likelihood of clot formation.

FIG. 44 is a flow chart illustrating a method 2590 of coupling an inlet flow cannula assembly to a wall of an organ according to an embodiment. The method 2590 includes inserting a tubular member into a body such that a connection portion of the tubular member is at least partially within an interior volume of an organ, at 2591. In some embodiments, the tubular member can be included in an inlet flow cannula or the like that is physically and fluidically coupled to an inlet port of a pump included in a ventricular assist device such as those described herein. In some instances, the tubular member can be inserted via an at least partially interventional procedure. That is to say, at least a portion of tubular member can be introduced to the interior volume of the organ via a vein. For example, in some embodiments, the organ can be the heart and the tubular member can be inserted into the interior volume defined by the left atrium. In such embodiments, the tubular member can be inserted through, for example, the jugular vein, as shown in FIG. 5. In this manner, the tubular member can be passed through the jugular vein, the superior vena cava, the right atrium, and the septum to be partially within the interior volume defined by the left atrium.

Once within the interior volume, the connection portion is moved from a collapsed configuration to an expanded configuration such that an outer edge of the connection portion contacts a first portion of an inner surface of a wall of the organ, thereby placing the interior volume of the organ in fluid communication with a lumen defined by the tubular member and fluidically isolating the interior volume of the organ from a volume outside of the organ, at 2592. For example, in some embodiments, the connection portion of the tubular member can be disposed at and/or can form a distal end portion of the tubular member. In some embodiments, the connection portion can be transitioned from the first configuration to the second configuration in a similar manner as described above with reference to the tubular member 1421 of FIGS. 21-28. In some embodiments, the connection portion can include, for example, one or more retention members or elements that can configured to couple the connection portion to the wall of the organ. For example, in some embodiments, the connection portion can be coupled to the wall of the organ via retention members such as the retention members 1530 and 1540 described above with reference to FIGS. 29-31. In this manner, the retention members can exert a force on the wall of the organ that can be sufficient to couple the connection portion thereto.

A support member is moved within a channel defined by the tubular member from a first position to a second position to limit movement of the wall relative to the tubular member, at 2593. For example, in some embodiments, the support member can be moved from its first position in which an end portion of the support member is disposed within the channel to its second position in which the end portion of the support member is disposed outside of the channel and in contact with a second portion of the inner surface of the wall. In some embodiments, the tubular member can define a channel such as, for example, the channel 2429 defined by the tubular member 2421 of FIG. 43. In this manner, the support member can be advanced through the channel towards its second position.

As described above, the end portion of the support member can extend away from the tubular member to place a surface of the support member substantially in continuous contact with the inner surface. In some embodiments, the second portion of the inner surface of the wall can have and/or include a larger surface area than a surface area included in and/or defined by the first portion of the inner surface in contact with the tubular member. Similarly stated, the support member can be in substantially continuous contact with the second portion of the inner surface to, for example, increase a footprint of the cannula assembly on the inner surface of the wall. Thus, the support member can limit movement of the wall of the organ relative to the tubular member that can, for example, reduce the likelihood of a suction event (e.g., a portion of the wall collapsing and obstructing the lumen or other vascular openings).

By maintaining the support structure in substantially continuous contact with the inner surface, the likelihood of clot formation is reduced, as described in detail above. The arrangement of the support member and the tubular member can also reduce eddy currents near the surface of the wall that would otherwise limit flow of blood to portions of the surface and thereby increase the risk of clot formation. In addition, any portion of the tubular member and/or the support member can include an outer surface and/or surface finish configured to reduce clot formation and/or increase tissue ingrowth. For example, in some embodiments, at least a portion of the tubular member and/or the support member can be substantially circumscribed by a fabric and/or outer surface such as Dacron®, polyester, polytetrafluoroethylene (PTFE), silicon, polypropylene, and/or the like. Thus, bodily tissue can form about at least a portion of the tubular member and/or the support member which can reduce the likelihood of clot formation. In some instances, the arrangement of the support member and the tubular member can increase an inlet flow rate into a pump of a VAD without substantially increasing a negative pressure differential between the pump and the interior volume, thereby reducing suction events that can otherwise be associated with the increased flow rate.

FIG. 45 is a flow chart illustrating a method 2690 of coupling a flow cannula to a wall of an organ according to an embodiment. The method 2690 includes insert a flow member, defining a first channel and a second channel, into a body such that a first end portion of the flow member is at least partially within an interior volume of the organ, at 2691. In some embodiments, the flow member can be, for example, a flow cannula or the like that is physically and fluidically coupled to a ventricular assist device such as those described herein. In some embodiments, the flow member can be substantially similar to or the same as the cannula assemblies 720, 820, 920, 1020, and/or 1120 described above. In this manner, the arrangement of the flow member can be such that the first channel can form or define, for example, a recirculation cannula or lumen, and the second channel can form or define, for example, an tubular member or the like, as described in detail above.

In some instances, the flow member can be inserted via an at least partially interventional procedure. That is to say, at least a portion of flow member can be introduced to the interior volume of the organ via a vein. For example, in some embodiments, the organ can be the heart and the flow member can be inserted into the interior volume defined by the left atrium. In such embodiments, the flow member can be inserted through, for example, the jugular vein, as shown in FIG. 5. In this manner, the flow member can be passed through the jugular vein, the superior vena cava, the right atrium, and the septum to be partially within the interior volume defined by the left atrium.

Once within the interior volume, the first end portion of the flow member is moved from a collapsed configuration to an expanded configuration such that an outer edge of the first end portion contacts an inner surface of the wall of the organ, thereby placing the interior volume of the organ in fluid communication with the first channel and the second channel, at 2692. For example, in some embodiments, the first end portion can be transitioned from the collapsed configuration to the expanded configuration in a similar manner as described above with reference to the flow member 1421 of FIGS. 21-28. In some embodiments, the first end portion can include, for example, one or more retention members or elements that can configured to couple the first end portion to the wall of the organ. For example, in some embodiments, the first end portion can be coupled to the wall of the organ via retention members such as the retention members 1530 and 1540 described above with reference to FIGS. 29-31. In this manner, the retention members can exert a force on the wall of the organ that can be sufficient to couple the first end portion thereto. In other embodiments, the first end portion can be transitioned from the collapsed configuration to the expanded configuration in any suitable manner such as any of those described above. In some embodiments, the first end portion can be transitioned from the collapsed configuration to the expanded configuration in a manner substantially similar to or the same as those described in U.S. Patent Publication No. 20120259157, the disclosure of which in incorporated by reference above.

The second end portion of the flow member is coupled to a pump to place the first channel in fluid communication with an outlet of the pump, and to place the second channel in fluid communication with an inlet of the pump, at 2693. As described above, the pump can be included in, for example, a ventricular assist device such as those described above. More particularly, in some embodiments, the pump can be substantially similar to the pumps 301, 401, 501, and/or 601 described above with reference to FIG. 4, FIGS. 5-7, FIG. 8, and FIGS. 9 and 10, respectively. In this manner, the first channel can be physically and fluidically coupled to the outlet of the pump and can be arranged as, for example, a recirculation cannula that defines a flow path in which fluid (e.g., blood) can flow from the pump to the interior volume of the organ (e.g., the left atrium). Similarly, the second channel can be physically and fluidically coupled to the inlet of the pump and can be arranged as, for example, an inlet flow cannula that defines a flow path in which fluid (e.g., blood) can flow from the interior region of the organ (e.g., the left atrium) to the pump, as described in detail above. In some embodiments, the arrangement of the flow member can be such that an increased flow rate through the pump and/or through the organ can be produced while limiting, for example, a negative pressure differential between the pump and the interior volume, as described above.

In some embodiments, the arrangement of the first channel and/or the second channel can, for example, reduce the likelihood of a suction event (e.g., an obstruction of the second channel by a portion of the wall of the organ) and/or a kinking or obstruction of any vascular opening defined by the wall of the organ. In some embodiments, the arrangement of the flow member can reduce the likelihood of clot formation and/or can reduce eddy currents near the surface of the wall that would otherwise limit flow of fluid to portions of the wall and thereby increase the risk of clot formation, as described in detail above. Moreover, any portion of the flow member can include, for example, an outer surface and/or surface finish configured to reduce clot formation and/or increase tissue ingrowth, as described in detail above.

Although the methods and embodiments are described above as coupling an inlet flow cannula assembly of a device to a wall of the left atrium to place the inlet flow cannula assembly in fluid communication with the left atrium, the inlet flow cannula assembly of any of the devices described herein can be coupled to any portion of the heart such as, for example, the left ventricle, the right ventricle, the right atrium, the septum between the left atrium and the right atrium, and/or the septum between the left ventricle and the right ventricle. In other embodiments, the inlet flow cannula assembly of any of the devices described herein can be coupled to any suitable vasculature structure to place the inlet flow cannula assembly in fluid communication therewith. In such embodiments, any portion of the inlet flow cannula assemblies can be changed in size or configuration in accordance with restrictions associated with the anatomy. For example, in some embodiments, a support member can be disposed within a left ventricle to limit and/or prevent collapse a left ventricular wall. In such embodiments, a portion of the wall supported by the support member can be reduced, for example, to allow for the normal contraction of the heart to be unencumbered. Thus, a partial support member that is limited to a region of the heart, particularly near the inlet flow cannula connection to the heart may be employed. Moreover, the inlet flow cannula in the left ventricle is typically inserted at the apex, so such a support member structure near the apex can be, for example, funnel-shaped extending away from the inlet flow cannula and in continuous contact with the ventricle wall to reduce the likelihood of clot formation.

Although the embodiments described herein include inlet flow cannulas that are used with ventricular assist devices or the like, any of the embodiments can be used with any suitable device and/or can be used to facilitate any suitable procedure. For example, any of the embodiments described herein can be used with any blood flow circuits such as, for example, in a cardiopulmonary bypass circuit for open heart surgery.

While various embodiments have been described above, it should be understood that they have been presented by way of example only, and not limitation. Where schematics and/or embodiments described above indicate certain components arranged in certain orientations or positions, the arrangement of components may be modified. While the embodiments have been particularly shown and described, it will be understood that various changes in form and details may be made. For example, although the inlet flow cannulas 1220 and 1320 are shown and described with reference to FIGS. 17-18 and FIGS. 19-20, respectively, as being disposed within a portion of the flow regulators 1270 and 1370, respectively, in other embodiments, a flow regulator can be disposed within a lumen of a cannula to regulate a flow therethrough. For example, in some embodiments, a cannula can include a flow regulator that includes one or more balloons, valves, iris, dilators, obstructions, gates, and/or the like that can be transitioned between a series of configurations to regulate a flow through the cannula. In other embodiments, a flow regulator can be included in, for example, an inlet port, an outlet port, and/or a recirculation port of a pump, such as those described herein. In still other embodiments, a VAD can include more than one pump that can be collectively or individually used to regulate a flow of fluid through a cannula.

Although the recirculation members (e.g., recirculation members 710, 810, 910, 1010 and 1110) are shown and described as being in a fixed position relative to the tubular members (e.g., tubular members 721, 821, 921, 1021 and 1121), in other embodiments, any of the recirculation members described herein can be movable relative to the tubular (or inflow) member. For example, in some embodiments, any of the recirculation members described herein can deform (i.e., change configuration and/or shape) relative to the tubular (or inflow) member. In other embodiments, any of the recirculation members described herein can slide (i.e., change position) relative to the tubular (or inflow) member.

Although various embodiments have been described as having particular features and/or combinations of components, other embodiments are possible having a combination of any features and/or components from any of embodiments as discussed above.

For example, any of the cannula assemblies described herein can include a connection portion having a fabric member arranged similar to the fabric member 1533 shown and described above with respect to FIGS. 29-31.

Any of the systems and methods described herein can employ any of the pumps described herein. Moreover, any of the systems and methods described herein can be configured to operate under a "high flow" condition (i.e., the total pump flow is greater than about 2.5 L/min, 3 L/min, 3.5 L/min, 4 L/min and 5 L/min).

Where methods described above indicate certain events and/or procedures occurring in certain order, the ordering of certain events may be modified. Additionally, certain of the events may be performed concurrently in a parallel process when possible, as well as performed sequentially as described above.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Some embodiments and/or methods described herein can be performed by software (executed on hardware), hardware, or a combination thereof. Hardware modules may include, for example, a general-purpose processor, a field programmable gate array (FPGA), and/or an application specific integrated circuit (ASIC). Software modules (executed on hardware) can be expressed in a variety of software languages (e.g., computer code), including C, C++, Java®, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

What is claimed:

1. An apparatus, comprising:
   a tubular member defining a lumen therethrough, the tubular member including a connection portion configured to be coupled to a wall of a heart such that an interior volume of the heart is in fluid communication with the lumen; and
   a recirculation member disposed at least partially within the lumen of the tubular member, the recirculation member defining a flow pathway therethrough such that the interior volume of the heart is in fluid communication with the flow pathway, the flow pathway configured to convey a fluid into the volume of the heart to minimize movement of the wall relative to the tubular member, the recirculation member defining a plurality of apertures arranged along a distal portion of the recirculation member such that a portion of the fluid can exit each aperture from the plurality of apertures and into the interior volume of the heart, the plurality of apertures including a first aperture and a second aperture spaced apart longitudinally from the first aperture.

2. The apparatus of claim 1, wherein the connection portion of the tubular member is configured to move from a collapsed configuration to an expanded configuration, the connection portion configured to be coupled to the wall when in its expanded configuration, a distal end of the recirculation member extending beyond a distal end of the tubular member when the connection portion is in the expanded configuration.

3. The apparatus of claim 1, wherein the recirculation member is configured to be spaced apart from an inner surface of the wall of the heart when the recirculation member is disposed within the interior volume of the heart.

4. The apparatus of claim 1, wherein at least a portion of the recirculation member is movably disposed within the lumen, an end portion of the recirculation member configured to be disposed within the lumen when the recirculation member is in a first configuration, the end portion of the recirculation member configured to be disposed outside the lumen and inside the interior volume of the heart when the recirculation member is in a second configuration.

5. The apparatus of claim 1, wherein the recirculation member defines the plurality of apertures such that a portion of the fluid can exit each aperture from the plurality of apertures having a different direction of flow within the interior volume of the heart.

6. The apparatus of claim 1, wherein the interior volume of the heart is defined by a left atrium of the heart, the wall of the heart being within the left atrium.

7. The apparatus of claim 1, further comprising:
   a support member coupled to the tubular member, the support member configured to move between a first configuration and a second configuration, at least a first portion of the support member being disposed within a lumen of the recirculation member when the support member is in its second configuration, and at least a second portion of the support member extending distally from a distal end portion of the recirculation member when the support member is in its second configuration.

8. An apparatus, comprising:
   a tubular member defining a lumen therethrough, the tubular member including a connection portion configured to move from a collapsed configuration to an expanded configuration, an outer edge of the connection portion configured to contact a first portion of an inner surface of a wall of a heart when the connection portion is in its expanded configuration such that an interior volume of the heart is in fluid communication with the lumen and is fluidically isolated from a volume outside of the heart, the interior volume of the heart being defined by a left atrium of the heart; and
   a support member coupled to the tubular member, the support member configured to minimize movement of the wall relative to the tubular member, the support member configured to move between a first configuration and a second configuration, the support member configured to contact a second portion of the inner surface of the wall when the support member is in its second configuration, the inner surface of the wall defining in part the interior volume of the heart, the second portion of the inner surface being distal to the first portion, the first portion of the inner surface and the second portion of the inner surface each being within the left atrium.

9. The apparatus of claim 8, wherein the support member has a helical shape when in the second configuration.

10. The apparatus of claim 8, wherein the support member is a wire having a spiral shape when in the second configuration.

11. The apparatus of claim 8, wherein a portion of the support member is substantially linear when in the first configuration, the portion of the support member having a helical shape when in the second configuration.

12. The apparatus of claim 8, wherein the support member is at least partially constructed from a material formulated to promote tissue ingrowth into the support member.

13. The apparatus of claim 8, wherein:
   the tubular member has a distal end portion defining an opening in fluid communication with the lumen; and a portion of the support member is configured to contact the second portion of the inner surface of the wall when the support member is in its second configuration, the portion of the support member being disposed distal to the opening defined by the distal end portion of the tubular member when the connection portion is in its expanded configuration.

14. The apparatus of claim 8, wherein a distal end portion of the support member is configured to be inserted into a pulmonary vein.

15. The apparatus of claim 8, wherein at least a portion of the support member has a curvature corresponding to a curvature of the second portion of the inner surface of the wall.

16. The apparatus of claim 8, wherein the wall is an atrial wall.

* * * * *